US010987322B2

(12) United States Patent
Jaen et al.

(10) Patent No.: US 10,987,322 B2
(45) Date of Patent: Apr. 27, 2021

(54) IMMUNOREGULATORY AGENTS

(71) Applicant: FLEXUS BIOSCIENCES, INC., Princeton, NJ (US)

(72) Inventors: Juan Carlos Jaen, Burlingame, CA (US); Maksim Osipov, Belmont, CA (US); Jay Patrick Powers, Pacifica, CA (US); Hunter Paul Shunatona, San Francisco, CA (US); James Ross Walker, Menlo Park, CA (US); Mikhail Zibinsky, Lodi, CA (US)

(73) Assignee: Flexus Biosciences, Inc., Princeton, NJ (US)

( * ) Notice: Subject to any disclaimer, the term of this patent is extended or adjusted under 35 U.S.C. 154(b) by 0 days.

(21) Appl. No.: 15/315,071

(22) PCT Filed: Jun. 5, 2015

(86) PCT No.: PCT/US2015/034449
§ 371 (c)(1),
(2) Date: Nov. 30, 2016

(87) PCT Pub. No.: WO2015/188085
PCT Pub. Date: Dec. 10, 2015

(65) Prior Publication Data
US 2017/0112785 A1 Apr. 27, 2017

Related U.S. Application Data

(60) Provisional application No. 62/008,947, filed on Jun. 6, 2014.

(51) Int. Cl.
| | | |
|---|---|---|
| A61K 31/15 | (2006.01) |
| C07D 295/155 | (2006.01) |
| C07D 213/58 | (2006.01) |
| C07D 307/16 | (2006.01) |
| A61K 45/06 | (2006.01) |
| C07C 259/12 | (2006.01) |
| C07D 211/62 | (2006.01) |
| C07D 277/56 | (2006.01) |
| A61K 31/4409 | (2006.01) |
| A61K 31/167 | (2006.01) |
| A61K 31/196 | (2006.01) |
| A61K 31/24 | (2006.01) |
| A61K 31/27 | (2006.01) |
| A61K 31/341 | (2006.01) |
| A61K 31/40 | (2006.01) |
| A61K 31/426 | (2006.01) |
| A61K 31/4402 | (2006.01) |
| A61K 31/445 | (2006.01) |
| A61K 31/5375 | (2006.01) |
| C07C 259/14 | (2006.01) |
| C07C 271/28 | (2006.01) |
| C07D 207/09 | (2006.01) |
| C07D 211/34 | (2006.01) |
| C07D 277/30 | (2006.01) |

(52) U.S. Cl.
CPC ............ *A61K 31/15* (2013.01); *A61K 31/167* (2013.01); *A61K 31/196* (2013.01); *A61K 31/24* (2013.01); *A61K 31/27* (2013.01); *A61K 31/341* (2013.01); *A61K 31/40* (2013.01); *A61K 31/426* (2013.01); *A61K 31/4402* (2013.01); *A61K 31/445* (2013.01); *A61K 31/4409* (2013.01); *A61K 31/5375* (2013.01); *A61K 45/06* (2013.01); *C07C 259/12* (2013.01); *C07C 259/14* (2013.01); *C07C 271/28* (2013.01); *C07D 207/09* (2013.01); *C07D 211/34* (2013.01); *C07D 211/62* (2013.01); *C07D 213/58* (2013.01); *C07D 277/30* (2013.01); *C07D 277/56* (2013.01); *C07D 295/155* (2013.01); *C07D 307/16* (2013.01); *C07C 2601/02* (2017.05); *C07C 2601/08* (2017.05); *C07C 2601/14* (2017.05); *Y02A 50/30* (2018.01)

(58) Field of Classification Search
CPC ..................................................... A61K 31/15
See application file for complete search history.

(56) References Cited

U.S. PATENT DOCUMENTS

| | | | |
|---|---|---|---|
| 5,455,273 A | 10/1995 | Maier et al. |
| 5,712,294 A | 1/1998 | Robert et al. |
| 5,723,464 A | 3/1998 | Brightwell et al. |
| 7,645,771 B2 | 1/2010 | Kazmierski et al. |

(Continued)

FOREIGN PATENT DOCUMENTS

| | | | |
|---|---|---|---|
| EP | 0596298 B1 | 1/2002 |
| EP | 1781656 B1 | 12/2007 |

(Continued)

OTHER PUBLICATIONS

American Chemical Society. (c) 2005. STN Database. RN 866251-45-8.*

(Continued)

*Primary Examiner* — John S Kenyon
(74) *Attorney, Agent, or Firm* — BakerHostetler

(57) ABSTRACT

Compounds that modulate the oxidoreductase enzyme indoleamine 2,3-dioxygenase, and compositions containing the compounds, are described herein. The use of such compounds and compositions for the treatment and/or prevention of a diverse array of diseases, disorders and conditions, including cancer- and immune-related disorders, that are mediated by indoleamine 2,3-dioxygenase is also provided.

21 Claims, 9 Drawing Sheets

(56) References Cited

U.S. PATENT DOCUMENTS

| | | | |
|---|---|---|---|
| 8,088,803 | B2 | 1/2012 | Combs et al. |
| 2002/0016463 | A1 | 2/2002 | Zablocki et al. |
| 2003/0190298 | A1 | 10/2003 | Bradley et al. |
| 2004/0029887 | A1 | 2/2004 | Bhatia et al. |
| 2004/0234623 | A1 | 11/2004 | Munn et al. |
| 2006/0258719 | A1* | 11/2006 | Combs ............... C07D 271/08 514/362 |
| 2007/0129347 | A1 | 6/2007 | Hinze et al. |
| 2007/0197584 | A1 | 8/2007 | Schwink et al. |
| 2008/0039453 | A1 | 2/2008 | Putman |
| 2008/0146569 | A1 | 6/2008 | Blake et al. |
| 2009/0275523 | A1 | 11/2009 | Schudok et al. |
| 2010/0008866 | A1 | 1/2010 | Blum et al. |
| 2010/0233166 | A1 | 9/2010 | Prendergast et al. |
| 2011/0218183 | A1 | 9/2011 | Chen |
| 2011/0306644 | A1 | 12/2011 | Hoekstra et al. |
| 2013/0197095 | A1 | 8/2013 | Nolte et al. |
| 2013/0217706 | A1 | 8/2013 | Tran et al. |
| 2014/0212444 | A1 | 7/2014 | Holoshitz et al. |
| 2016/0137652 | A1 | 5/2016 | Beck et al. |
| 2016/0137653 | A1 | 5/2016 | Beck et al. |

FOREIGN PATENT DOCUMENTS

| | | |
|---|---|---|
| JP | 07-330764 | 12/1995 |
| JP | 2008-540548 | 11/2008 |
| JP | 2009-520817 | 5/2009 |
| JP | 2010-504347 | 2/2010 |
| WO | 96/34857 | 11/1996 |
| WO | WO 99/29310 | 6/1999 |
| WO | WO 2000/056727 | 9/2000 |
| WO | WO 2001/092204 | 12/2001 |
| WO | WO 2004/094409 | 11/2004 |
| WO | WO 2005/080317 | 9/2005 |
| WO | WO 2006/018279 | 2/2006 |
| WO | WO 2006/029879 | 3/2006 |
| WO | WO 2006/105021 | 10/2006 |
| WO | WO 2007/005874 | 1/2007 |
| WO | 20071075598 | 7/2007 |
| WO | 2008/036643 A2 | 3/2008 |
| WO | WO 2008/132601 | 11/2008 |
| WO | WO 2009/009116 | 1/2009 |
| WO | WO 2009/044273 | 4/2009 |
| WO | WO 2009/052320 | 4/2009 |
| WO | WO 2010/015655 | 2/2010 |
| WO | WO 2010/019570 | 2/2010 |
| WO | WO 2010/075376 | 7/2010 |
| WO | WO 2010/077634 | 7/2010 |
| WO | WO 2011/028683 | 3/2011 |
| WO | WO 2011/070024 | 6/2011 |
| WO | WO 2011/107553 | 9/2011 |
| WO | WO 2011/109400 | 9/2011 |
| WO | WO 2011/131407 | 10/2011 |
| WO | WO 2011/140249 | 11/2011 |
| WO | WO 2012/032433 | 3/2012 |
| WO | WO 2012/145493 | 10/2012 |
| WO | WO 2013/079174 | 6/2013 |
| WO | WO 2013/079425 | 6/2013 |
| WO | WO 2013/087699 | 6/2013 |
| WO | WO 2013/119716 | 8/2013 |
| WO | WO 2013/132044 | 9/2013 |
| WO | WO 2013/169264 | 11/2013 |
| WO | WO 2014/008218 | 1/2014 |
| WO | WO 2014/036357 | 3/2014 |
| WO | WO 2014/036412 | 3/2014 |
| WO | WO 2014/150677 | 9/2014 |
| WO | WO 2014/160967 | 10/2014 |
| WO | WO 2015/188085 | 12/2015 |
| WO | WO 2016/071283 | 5/2016 |
| WO | WO 2016/073738 | 5/2016 |
| WO | WO 2016/073770 | 5/2016 |
| WO | WO 2016/073774 | 5/2016 |

OTHER PUBLICATIONS

American Chemical Society. (c) 1984. STN Database. RN 1222-25-9.*

American Chemical Society. (c) 1984. STN Database. RN 19206-29-2.*

American Chemical Society. Chemical Abstract Service (CAS). RN 875214-90-7. First made available to public/entered into STN on Feb. 26, 2006. (Year: 2006).*

Fang, Fang, et al. "FeCl3*6H2O-mediated reaction of [60]fullerene with amidoximes." Tetrahedron. (2016), vol. 72, pp. 2476-2480. (Year: 2016).*

International Search Report dated Mar. 17, 2016 issued in PCT/US15/59311, 3 pages.

International Search Report dated May 17, 2016 issued in PCT/US15/59316, 2 pages.

International Search Report dated Dec. 10, 2015 issued in PCT/US15/34449, 1 page.

https://pubchem.ncbi.nlm.gov/compound/70339979#section=top; Pub Chem Open Chemistry Database: Compound Summary for CID 70339979; Dec. 20, 2015; 3 pages.

National Center for Biotechnology Information, Pubchem Compound Database; CID=24231423, https://pubchem.ncbi.nlm.nih.gov/compound/24231423 (accessed Jun. 23, 2016). 9 pages.

Pubchem SID=162741420, May 22, 2013, pp. 1-5 [online], [retrieved on Dec. 21, 2015], retrieved from the Internet <URL: https://pubchem.ncbi.nlm.nih.gov/substance/162741420>; p. 3. (accessed Jul. 11, 2016).

Serafini, P. et al., Myeloid suppressor cells in cancer: recruitment, phenotype, properties, and mechanisms of immune suppression. Seminars in Cancer Biology, 16(1):53-65 Feb. 2006.

Ball, H.J. et al., Characterization of an indoleamine 2, 3-dioxygenase-like protein found in humans and mice, Gene, 396(1):203-213 Jul. 2007.

Brandacher, G. et al., Prognostic value of indolemaine 2,3-dioxygenase expression in colorectal cancer: effect on tumor-infiltrasting T cells, Clin. Cancer Res., 12(4):1144-1151 Feb. 2006.

Berge, S. M. et al., Pharmaceutical Salts, J. Pharm. Sci., 66:1-19, Jan. 1977.

Munsen et al., Ligand a versatile computerized approach for characterization of ligand-binding systems, Analytical Biochemistry, 107(1), 220-239, Sep. 1980.

Platten, M. et al., Tryptophan catabolism in cancer: beyond IDO and tryptophan depletion, Cancer Research, 72(21):5435-5440, Nov. 2012.

Ishiyama, et al., Palladium (0)-catalyzed cross-coupling reaction of alkoxydiboron with halorenes: a direct procedure for arylboronic esters., J. Org. Chem., 60, 7508-7510, Nov. 1995.

El-Faham, et al., Peptide coupling reagents, more than a letter soup, Chemical Reviews, 111.11, 6557-6602, Aug. 2011.

Evans, et al., Asymmetric alkylation reactions of chiral imide enolates. A practical approach to the enantioselective synthesis of alpha-substituted carboxylic acid derivatives, Journal of the American Chemical Society, 104(6), pp. 1737-1739, Mar. 1982.

Chiang et al., An Fc Domain Protein-Small Molecule Conjugate as an Enhanced Immunomodular, Journal of the American Chemical Society, 136(9):3370-3373, Feb. 2014.

Li, W. et al., Current drug research on PEGylation with small molecular agents, Progress in Polymer Science, 38:421-444, Apr. 2013.

Ramirez-Montagut et al., Immunity to melanoma: unraveling the relation of tumor immunity and autoimmunity, Oncogene, 22(20):3180-3187, May 2003.

Sawaya et al., Risk of cervical cancer associated with extending the interval between cervical-cancer screenings, New England Journal of Medicine, 349(16): 1501-1509, Oct. 2003.

Pardoll, The blockade of immune checkpoints in cancer immunotherapy, Nature Reviews Cancer, 12(4):252-264, Apr. 2012.

(56) References Cited

OTHER PUBLICATIONS

Sarkar, et al., Induction of indoleamine 2, 3-dioxygenase by interferon-y in human islets, Diabetes, 56(1):72-79, Jan. 2007.
Littlejohn, et al., Expression and Purification of Recombinant Human Indoleamine 2,3-Dioxygenase, Protein Expression and Purification, 19(1):22-29, Jun. 2000.
Fox, et al., Discovery of 6-phenylpyrimido [4,5-b][1,4] oxazines as potent and selective acyl CoA: diacylglycerol acytransferase 1 (DGAT1) inhibitors with in vivo efficacy in rodents, Journal of Medical Chemistry, 57(8):3464-3483, Apr. 2014.
Yamamoto, et al., Additional reaction of arylboronic acid to aldehydes and α,β-unsaturated carbonyl compounds catalyzed by conventional palladium complexes in the presence of chloroform, J Organomet, Chem., 69(9)4:1325-1332, Apr. 2009.
Li, G. et al., Discovery of novel orally active ureido NPY Y5 receptor antagonists, Bioorganic & Medical Chemistry Letters, 18(3):1146-1150, Feb. 2008.
Kawamura et al., Iron-catalysed cross-coupling of halohydrins with aryl aluminum reagents: a protecting-group-free strategy attaining remarkable rate enhancement and diastereoinduction, Chemical Communications, 48(75):9376-9378, Aug. 2012.
Vilums, Design and synthesis of novel small molecule CCR2 antagonists: Evaluation of 4-aminopiperidine derivatives, Bioorganic Medical Chemistry Letters, 24(23):5377, Dec. 2014.
Qureshi et al., Indoleamine 2,3-dioxygenase; potential in cancer immunotherapy, Science Vision, 2013, vol. 19(1,2), pp. 33-40.
Kotha et al, Recent applications of Suzuki-Miyaura cross-coupling reaction in organic synthesis, Tetrahedron, Nov. 2002, 58:9633-9695.
Kinzel et al., A new palladium precatalyst allows for the fast Suzuki-Miyaura coupling reactions of unstable polyfluorophenyl and 2-heteroaryl boronic acids, Jouranl of the American Chemical Society, Sep. 2010, 132(40), 14073-14075.
Evans et al., Contrasteric carboximide hydrolysis with lithium hydroperoxide, Tetrahedron Letters, Dec. 1987, 28(49), 6141-6144.
Stocks et al., Evidence for a Common Non-Heme Chelatable-Iron-Dependent Activation Mechanism for Semisynthetic and Synthetic Endoperoxide Antimalarial Drugs, Angew. Chem. Int. Ed., Aug. 2007, 46(33), 6278-6283.
Barlind et al., Design and optimization of pyrazinecarboxamide-based inhibitors of diacylglycerol acyltransferase 1 (DGAT1) leading to a clinical candidate dimethylpyrazinecarboxamide phenylcyclohexylacetic acid (AZD7687), Journal of medicinal chemistry, Nov. 2012, 55(23), 10610-10629.
Corsello, et al. Endorine Side effects induced by immune checkpoint inhibitors, 98(4), Apr. 2013, 1361-1375.
Kohrt, et al., Anti-KIR antibody enhancement of anti-lymphoma activity of natural killer cells as monotherapy and in combinatin with anti-CD20 antibodies, Blood 123.5, Jan. 2014, 678-686.
Stucchi, et al., Multicomponent Synthesis and Biological Evaluation of a Piperazine-Based Dopamine Receptor Ligand Library, ACS medicinal chemistry letters 6(8), Jun. 2015, 882-887.
Pubchem CID 57911539, Aug. 19, 2012, pp. 1-11 [online], [retrieved on Dec. 17, 2015], Retrieved from the Internet <URL:https://pubchem.ncbi.nlm.nih.gov/compound/57911539#section=Top.>; p. 3.
Robinson et al., Kinetic resolution strategies using non-enzymatic catalysts, Tetrahedron, 14(1), 2003, 1407-1446.
International Search Report dated May 13, 2016 issued in PCT/US15/59271, 3 pages.
Uno H et al: "Studies on 3-Substituted 1,2-Benzisoxazole Derivatives. I", Chemical and Pharmaceutical Bulletin, Pharmaceutical Society of Japan, JP, vol. 24, No. 4, Apr. 1, 1976 (Apr. 1, 1976), pp. 632-643, XP000608775, ISSN: 0009-2363.
Sanguineti Gabriella et al: "Studies on the synthesis of amidoximes from nitroalkanes," Tetrahedron, Elsevier Science Publishers, Amsterdam, NL, vol. 67, No. 52, Oct. 6, 2011 (Oct. 6, 2011), pp. 10208-10211, XP028599480, ISSN: 0040-4020, DOI: 10.1016/J.TET.2011.09.147.
Oct Hurd: "Hydroximyl Chlorides from Nitrostyrenes", J. Am. Chem. Soc., 1950, 72 (10), pp. 4697-4699, Jan. 1, 1950 (Jan. 1, 1950), pp. 2487-1764, XP55411250, Retrieved from the Internet: URL:http://pubs.acs.org/doi/pdf/10.1021/ja01166a096 [retrieved on Sep. 29, 2017].
Grundmann C et al: "Nitrile Oxides. XII. Cycloaliphatic and Alipath IC Stable Nitrile Oxides", The Journal of Organic Chemistry, American Chemical Society, US, vol. 34, No. 6, Jan. 1, 1969 (Jan. 1, 1969), pp. 2016-2018, XP002024465, ISSN: 0022-3263, DOI: 10.1021/J001258A125.
Georgia Melagraki et al: "Predictive QSAR workflow for the in silico identification and screening of novel HDAC inhibitors", Molecular Diversity, Kluwer Academic Publishers, DO, vol. 13, No. 3, Feb. 10, 2009 (Feb. 10, 2009), pp. 301-311, XP019732283, ISSN: 1573-501X, DOI: 10.1007/S11030-009-9115-2.
George C. Prendergast et al: "Indoleamine 2,3-dioxygenase pathways of pathogenic inflammation and immune escape in cancer", Cancer Immunology, Immunotherapy, vol. 63, No. 7, Apr. 8, 2014 (Apr. 8, 2014), pp. 721-735, XP55411380, Berlin/Heidelberg ISSN: 0340-7004, DOI: 10.1007/S00262-014-1549-4.
Database CA [Online] Chemical Abstracts Service, Columbus, Ohio, US; Knunyants, I. L. et al: "Reaction of hydroxyl amine with pseudoolefins", XP002774276, retrieved from STN Database accession No. 1965:15020 & Knunyants, I. L. et al: "Reaction of hydroxyl amine with pseudoolefins", Zhurnal Vses0yuzn0g0 Khimichesk0g0 Obshchestva IM. D. I. Mendeleeva , 9(5), 598-9 C0den: ZVK0A6; ISSN: 0373-0247, 1964.
Boyer: "Dehydration of Amidoximes with and without Rearrangement", J . Org. Chem., vol. 35, No. 7, 1970, 2449-2450, Jan. 1, 1970 (Jan. 1, 1970), XP55411265, Retrieved from the Internet: URL:http://pubs.acs.org/doi/pdf/10.1021/jo00832a091 [retrieved on Sep. 29, 2017].
Baker K W J et al: "Synthesis of pyranosyl amidoximes by addition of amines to pyranosyl nitrile oxides", Tetrahedron Letters, Elsevier, Amsterdam, NL, vol. 45, No. 48, Nov. 22, 2004 (Nov. 22, 2004), pp. 8913-8916, XP027297837, ISSN: 0040-4039 [retrieved on Oct. 29, 2004].
Alan R. Katritzky et al: "Microwave-Assisted Preparations of Amidrazones and Amidoximes", The Journal of Organic Chemistry, vol. 71, No. 24, Nov. 1, 2006 (Nov. 1, 2006), pp. 9051-9056, XP55255367, US ISSN: 0022-3263, DOI: 10.1021/jo061410u.
Supplementary European search report dated Oct 20, 2017 for EP Application No. 15802353.

\* cited by examiner

IMMUNOREGULATORY AGENTS

CROSS-REFERENCES TO RELATED APPLICATIONS

This application is a National Stage Application filed under 35 U.S.C. 371 of International Application No. PCT/US2015/034449, filed Jun. 5, 2015, which claims the benefit of priority under 35 U.S.C. § 119(e) to U.S. Provisional Application Ser. No. 62/008,947, filed Jun. 6, 2014 the entireties of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formylkynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini P, et al., Semin Cancer Biol. 2006 February: 16(1):53-65 and Ball H J, et al., Gene. 2007 Jul. 1:396(1):203-13).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher G. et al., Clin Cancer Res. 2006 Feb. 15; 12(4):1144-51).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

BRIEF SUMMARY OF THE INVENTION

The present invention relates to compounds that modulate the oxidoreductase enzyme indoleamine 2,3-dioxygenase (IDO), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by IDO. Such diseases, disorders and conditions are described in detail elsewhere herein. Unless otherwise indicated, when uses of the compounds of the present invention are described herein, it is to be understood that such compounds may be in the form of a composition (e.g., a pharmaceutical composition).

As discussed hereafter, although the compounds of the present invention are believed to effect their activity by inhibition of IDO, a precise understanding of the compounds' underlying mechanism of action is not required to practice the invention. It is envisaged that the compounds may alternatively effect their activity through inhibition of tryptophan-2,3-dioxygenase (TDO) activity. It is also envisaged that the compounds may effect their activity through inhibition of both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

In one aspect, the present invention provides compounds represented by formula (I):

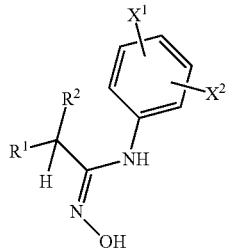

or a pharmaceutically acceptable salt, hydrate or solvate thereof.

In formula (I), $X^1$ and $X^2$ represent independently selected substituents selected from hydrogen, halogen, CN, $SO_2NH_2$, $NHSO_2CH_3$, $NHSO_2CF_3$, $OCF_3$, $SO_2CH_3$, $SO_2CF_3$, optionally substituted $C_1$-$C_4$ alkyl, optionally substituted $C_1$-$C_4$ alkoxy, $C_1$-$C_4$ haloalkyl, cyclopropyl and $CONH_2$. Additionally, when $X^1$ and $X^2$ are on adjacent vertices of the phenyl ring they are optionally joined together to form an optionally substituted 5- or 6-member aromatic or aliphatic ring containing 0, 1, or 2 heteroatoms.

$R^1$ and $R^2$ are independently selected from the group consisting of hydrogen, optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, hydroxyl, optionally substituted aryl, and optionally substituted heteroaryl; and $R^1$ and $R^2$ are optionally joined together to form an optionally substituted $C_3$-$C_8$ cycloalkyl or optionally substituted 3- to 7-membered cycloheteroalkyl with the proviso that $R^1$ and $R^2$ do not join together to form an unsubstituted cyclohexane ring, and at least one of $R^1$ and $R^2$ is other than hydrogen.

In another aspect, the present invention provides compounds represented by formula (II):

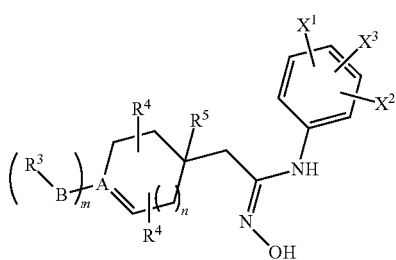

or a pharmaceutically acceptable salt, hydrate or solvate thereof.

In formula (II), the dashed line represents a single or double bond between ring vertices; $X^1$, $X^2$ and $X^3$ are substituents independently selected from hydrogen, halogen, CN, $SO_2NH_2$, $NHSO_2CH_3$, $NHSO_2CF_3$, $OCF_3$, $SO_2CH_3$, $SO_2CF_3$, optionally substituted $C_1$-$C_4$ alkyl, optionally substituted $C_1$-$C_4$ alkoxy, $C_1$-$C_4$ haloalkyl, cyclopropyl and $CONH_2$; and when $X^1$ and $X^2$ are on adjacent vertices of the phenyl ring they are optionally joined together to form an optionally substituted 5- or 6-member aromatic or aliphatic ring containing 0, 1, or 2 heteroatoms; $R^3$ is selected from hydrogen, optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, optionally substituted aryl, and optionally substituted heteroaryl; B is selected from a bond, C(O), optionally substituted $C_1$-$C_8$ alkyl and optionally substituted $C_2$-$C_8$ heteroalkyl; A is selected from O, C, $CR^4$, N and $NR^4$; each $R^4$ is independently selected from hydrogen, $C_1$-$C_4$ alkyl, $C_1$-$C_4$ alkoxy, $C_1$-$C_4$ haloalkyl and hydroxyl; $R^5$ is selected from hydrogen, hydroxyl, $CH_3$, and $CF_3$; the subscript m is 0, when A is O, and m is 1 when A is selected from N, $NR^4$ and $CR^4$; and the subscript n is 0 or 1, indicating the ring having A as a ring vertex is either a five-membered or six-membered ring.

In yet another aspect, the present invention provides compositions in which compounds of formula (I) or (II), or combinations thereof, are combined with one or more pharmaceutically acceptable excipients.

In some embodiments, the present invention contemplates methods for treating or preventing cancer in a subject (e.g., a human) comprising administering to the subject a therapeutically effective amount of at least one IDO inhibitor described herein. The present invention includes methods of treating or preventing a cancer in a subject by administering to the subject an IDO inhibitor in an amount effective to reverse or stop the progression of IDO-mediated immunosuppression. In some embodiments, the IDO-mediated immunosuppression is mediated by an antigen-presenting cell (APC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an IDO inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one IDO inhibitor (e.g., a novel inhibitor of the instant invention). In some embodiments, the infective disorder is a viral infection (e.g., a chronic viral infection), a bacterial infection, or a parasitic infection. In certain embodiments, the viral infection is human immunodeficiency virus or cytomegalovirus. In other embodiments, the bacterial infection is a *Mycobacterium* infection (e.g., *Mycobacterium leprae* or *Mycobacterium tuberculosis*). In still other embodiments, the parasitic infection is *Leishmania donovani, Leishmania tropica, Leishmania major, Leishmania aethiopica, Leishmania mexicana, Plasmodium falciparum, Plasmodium vivax, Plasmodium ovale,* or *Plasmodium malariae.* In further embodiments, the infective disorder is a fungal infection.

In still other embodiments, the present invention contemplates methods for treating or preventing an immune-related disease, disorder or condition in a subject (e.g., a human), comprising administering to the subject a therapeutically effective amount of at least one IDO inhibitor (e.g., preferably a novel inhibitor of the instant invention). Examples of immune-related diseases, disorders and conditions are described hereafter.

Other diseases, disorders and conditions that may be treated or prevented, in whole or in part, by modulation of IDO activity are candidate indications for the IDO inhibitor compounds that are described herein.

The present invention further contemplates the use of the IDO inhibitors described herein in combination with one or more additional agents. The one or more additional agents may have some IDO modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the IDO inhibitor(s) and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In some embodiments, the present invention further comprises the use of the IDO inhibitors described herein in combination with bone marrow transplantation, peripheral blood stem cell transplantation, or other types of transplantation therapy.

In particular embodiments, the present invention contemplates the use of the inhibitors of IDO function described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine Ata receptor A2aR); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one IDO inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the IDO inhibitors in combination with other agents known in the art (e.g., arsenic trioxide) and other chemotherapeutic agents developed in the future.

In some embodiments drawn to methods of treating cancer, the administration of a therapeutically effective amount of an IDO inhibitor in combination with at least one chemotherapeutic agent results in a cancer survival rate greater than the cancer survival rate observed by administering either alone. In further embodiments drawn to methods of treating cancer, the administration of a therapeutically effective amount of an IDO inhibitor in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one IDO inhibitor and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an IDO inhibitor in conjunction with at least one chemotherapeutic agent and/or radiation therapy, wherein the resulting rejection of tumor cells is greater than that obtained by administering either the IDO inhibitor, the chemotherapeutic agent or the radiation therapy alone.

In further embodiments, the present invention provides methods for treating cancer in a subject, comprising administering to the subject a therapeutically effective amount of at least one IDO inhibitor and at least one immunomodulator other than an IDO inhibitor. In particular embodiments, the at least one immunomodulator is selected from the group consisting of CD40L, B7, B7RP1, ant-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-α/-β, M-CSF, IL-3, GM-CSF, IL-13, and anti-IL-10. Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one IDO inhibitor and a therapeutically effective amount of an anti-infective agent(s)

In some embodiments of the present invention, the additional therapeutic agent is a cytokine, including, for example granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the IDO inhibitors described herein to treat (either alone or as a component of combination therapy) infection is discussed further hereafter.

In additional embodiments, treatment of an infective disorder is effected through the co-administration of a vaccine in combination with administration of a therapeutically effective amount of an IDO inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In some embodiments, the present invention contemplates methods of using the IDO inhibitors disclosed herein in combination with one or more antimicrobial agents.

In certain embodiments drawn to treatment of an infection by administering an IDO inhibitor and at least one additional therapeutic agent, a symptom of infection observed after administering both the IDO inhibitor and the additional therapeutic agent is improved over the same symptom of infection observed after administering either alone. In some embodiments, the symptom of infection observed may be reduction in viral load, increase in CD4$^+$ T cell count, decrease in opportunistic infections, increased survival time, eradication of chronic infection, or a combination thereof.

DETAILED DESCRIPTION OF THE INVENTION

Figure 1:
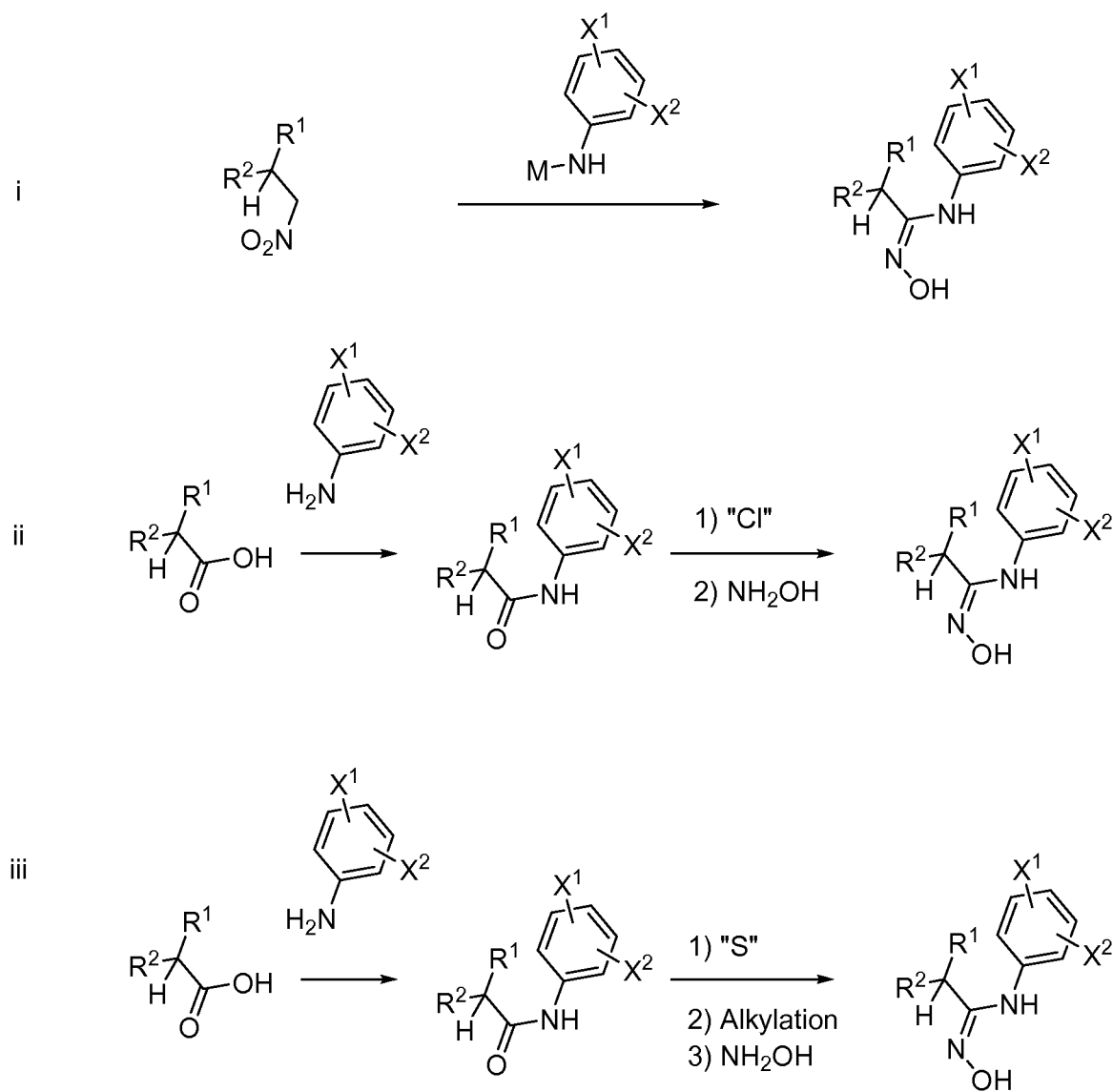
FIG. 1 provides a synthesis scheme for the preparation of compounds described herein.
Figure 2A:
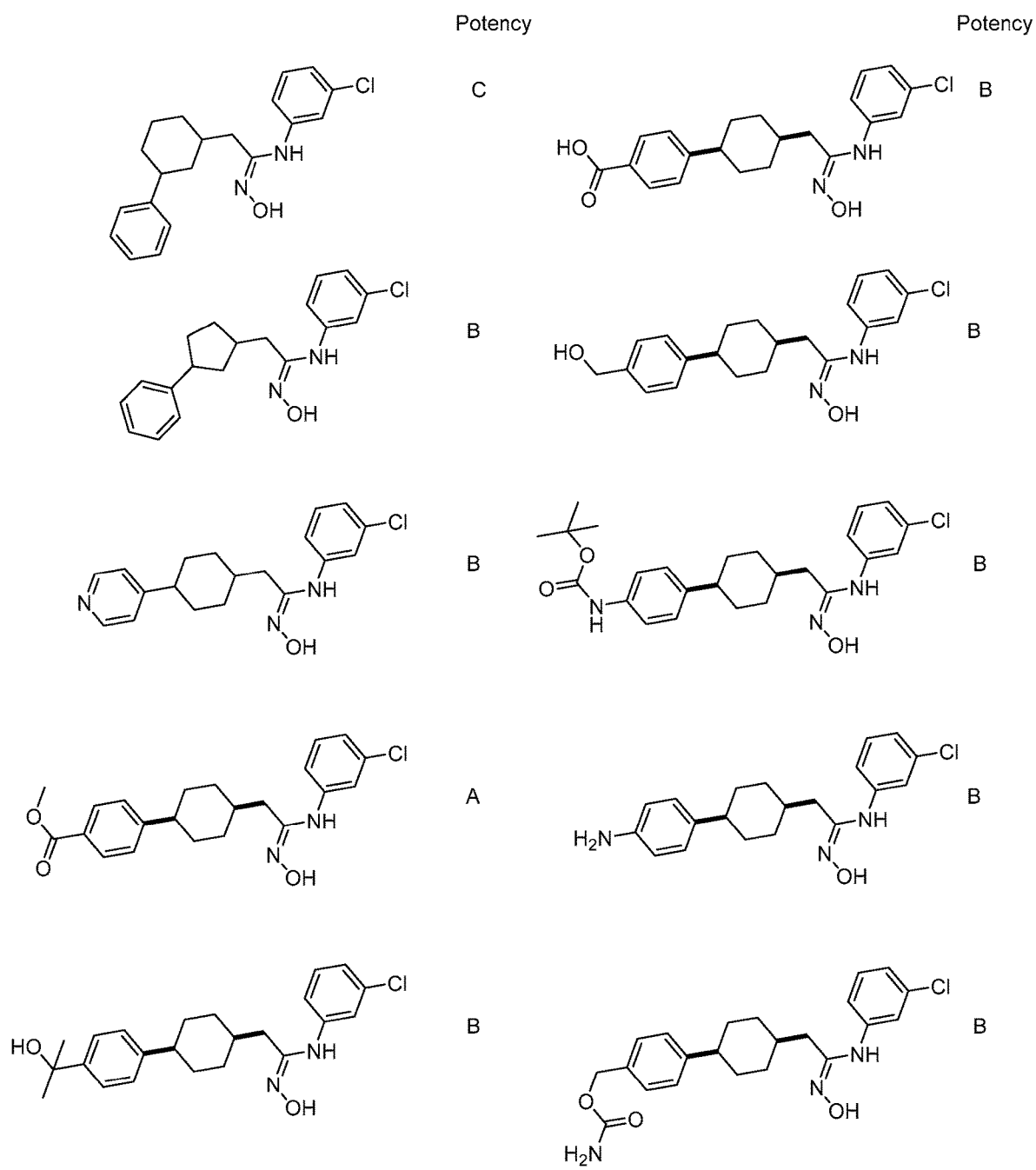
FIGS. 2A-2H provide structures and activity data for compounds provided herein.
Figure 2B:
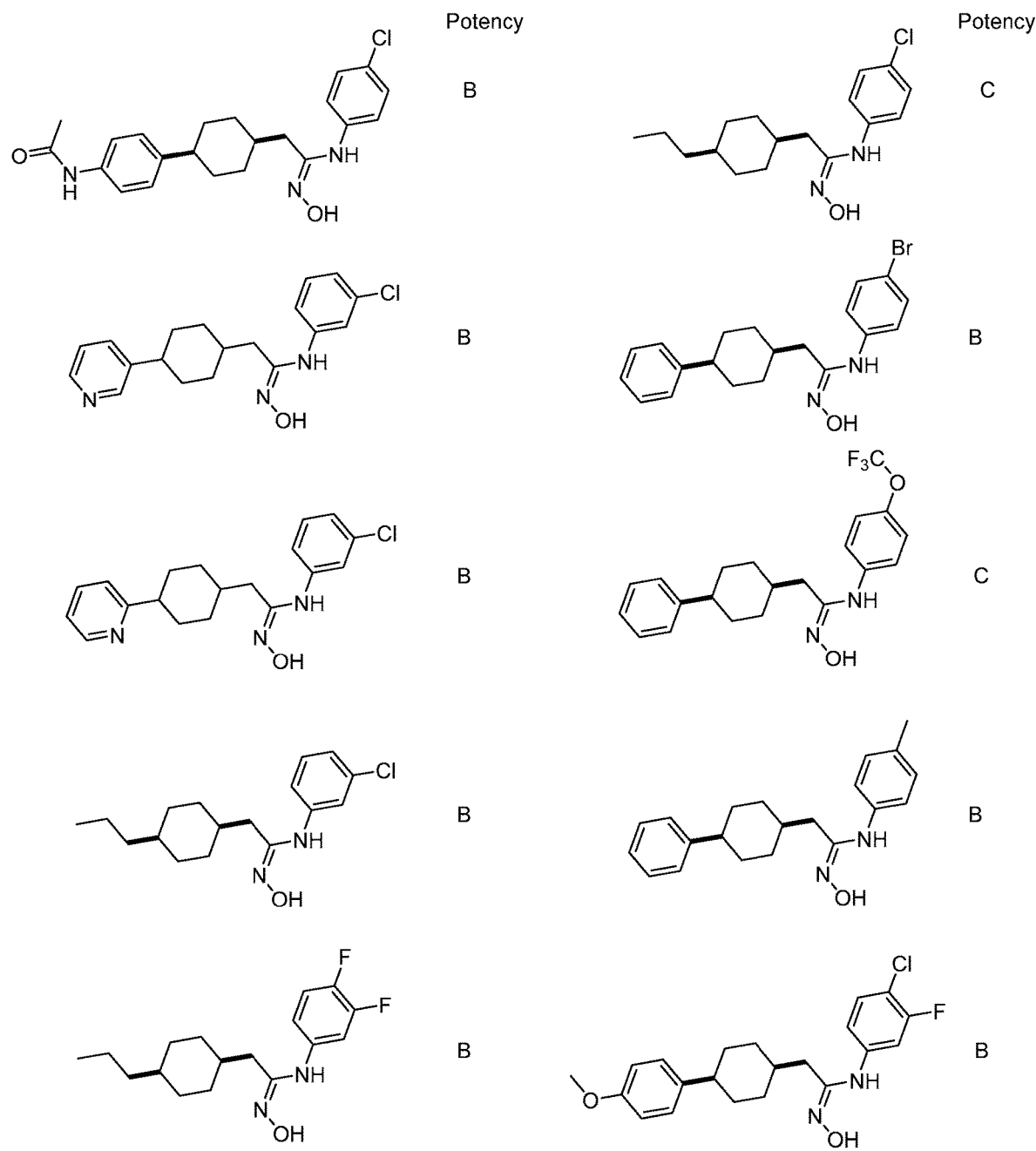
Figure 2C:
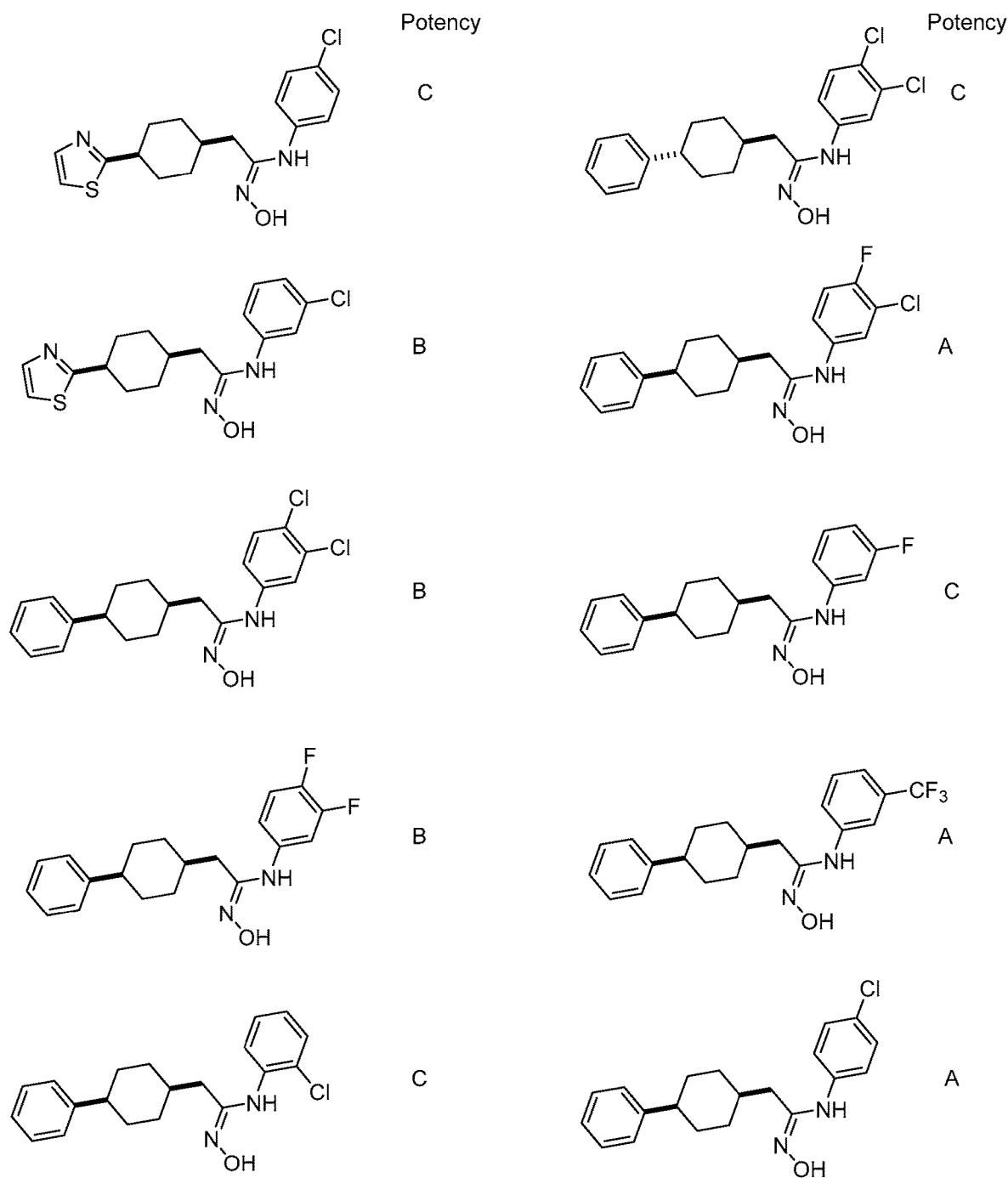
Figure 2D:
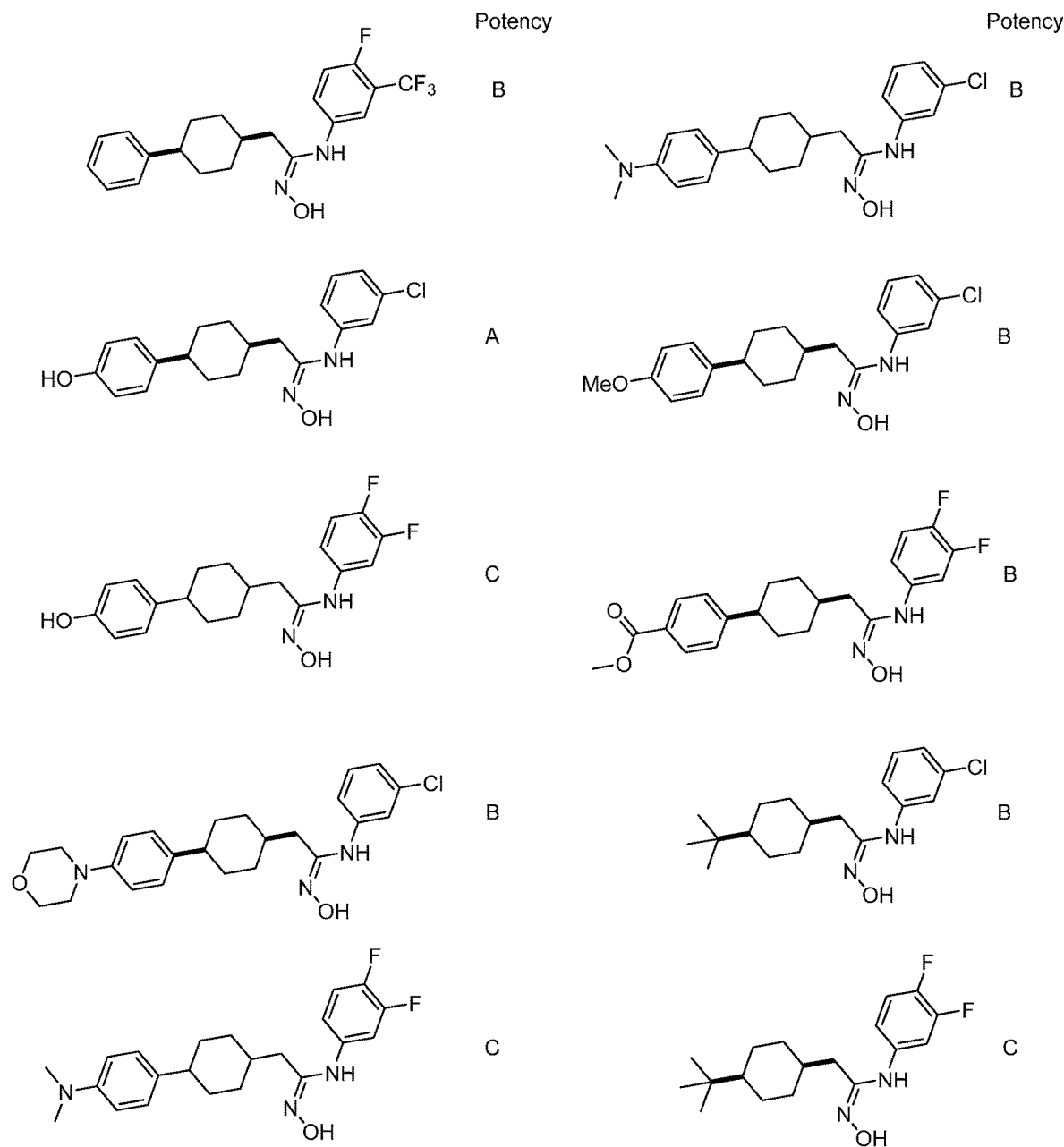
Figure 2E:
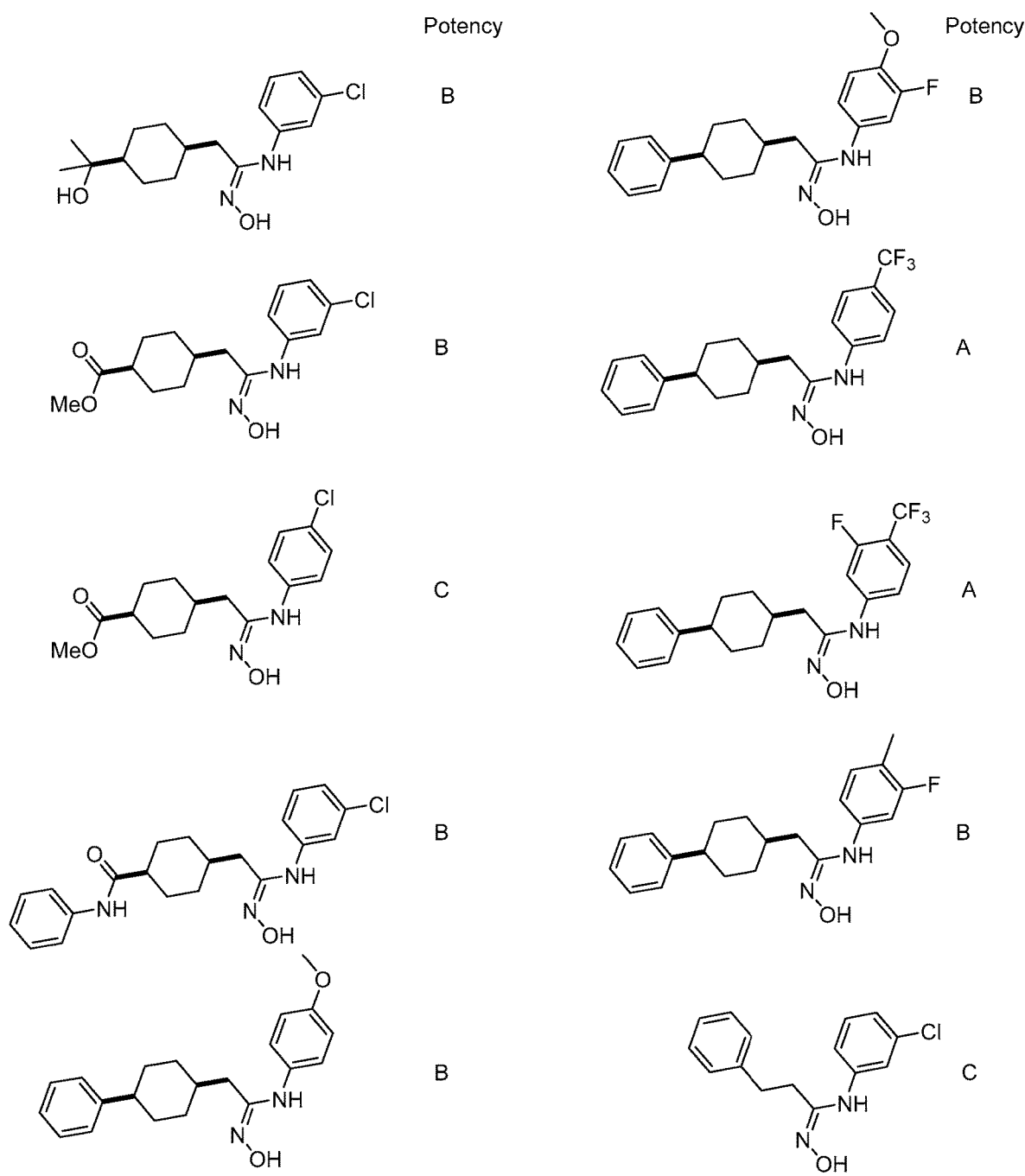
Figure 2F:
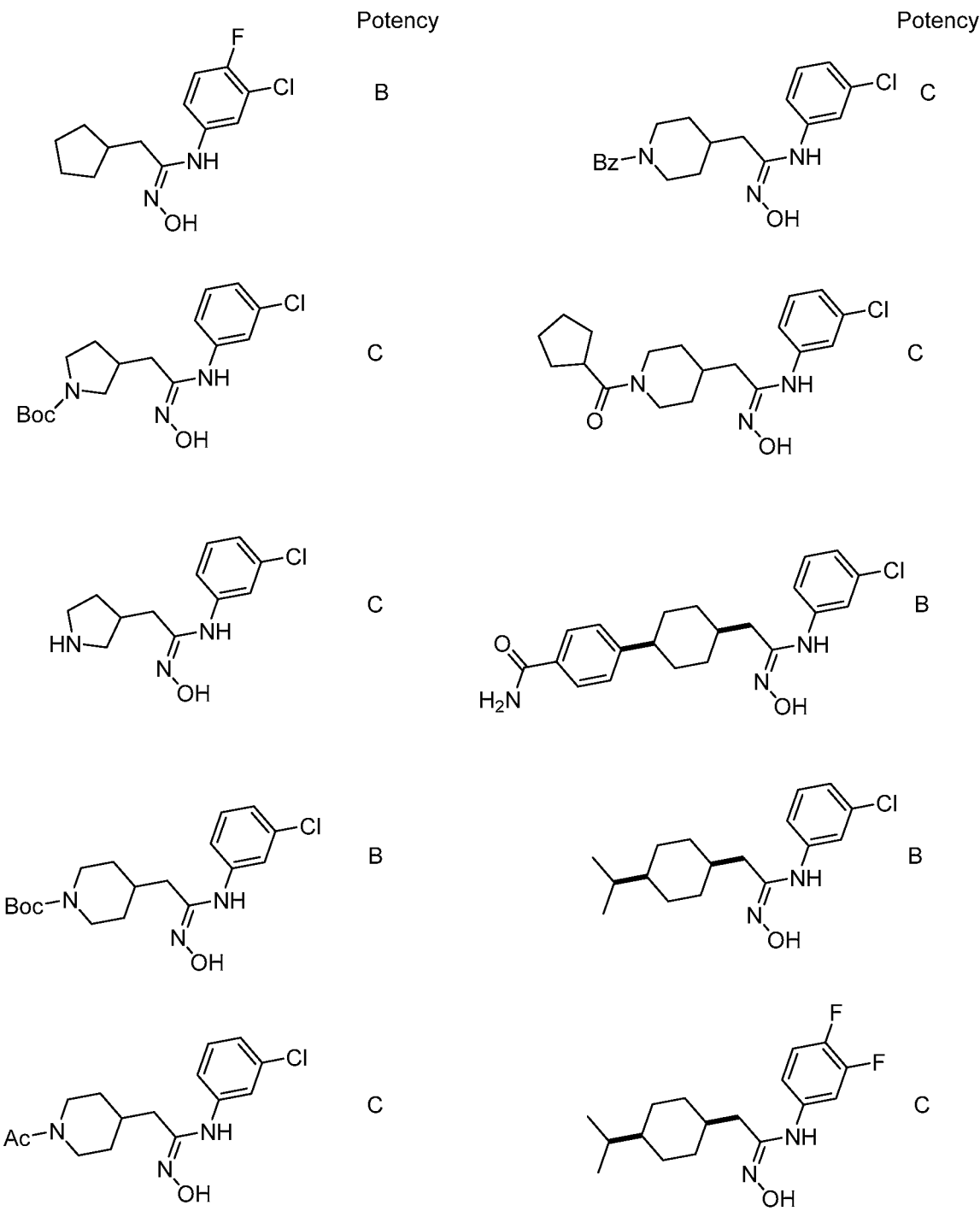
Figure 2G:
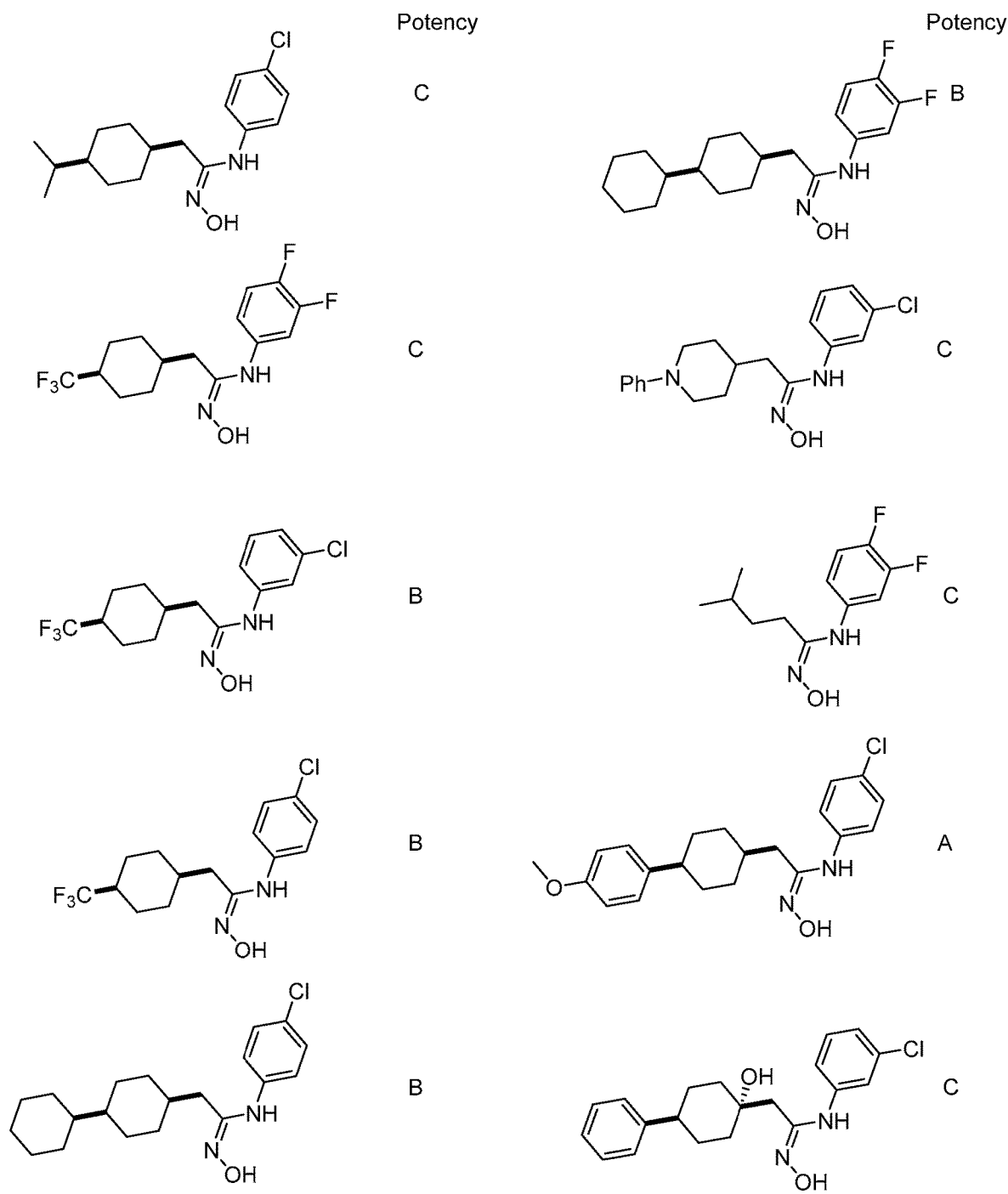
Figure 2H:
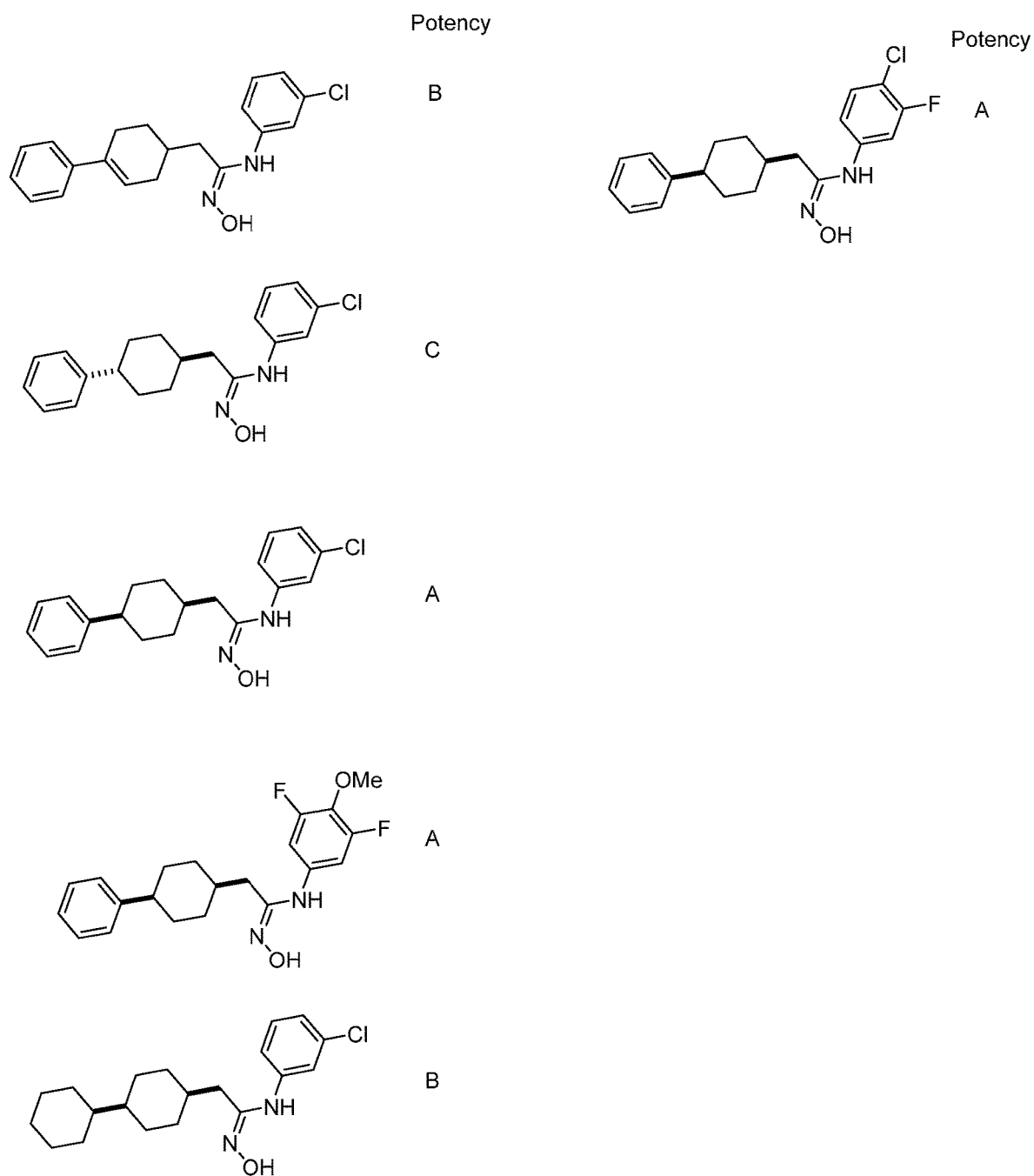

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the terth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Immune dysregulation is intimately associated with tumor evasion of the host immune system, resulting in tumor growth and progression. Traditional treatment approaches comprising chemotherapy and radiotherapy are generally difficult for the patient to tolerate and become less effective as tumors evolve to survive such treatments. By utilizing the patient's own immune system to identify and eliminate tumor cells, immunotherapy has the benefit of reduced toxicity. As upregulation of the immunoregulatory enzyme indoleamine 2,3-dioxygenase comprises one mechanism manipulated by tumors to promote growth, agents (e.g., small molecule compounds) that inhibit enzyme activity present a promising avenue for prophylaxis and/or treatment.

In addition, a large body of experimental data indicates a role for IDO inhibition in immunosuppression, tumor resistance and/or rejection, chronic infections, HIV-infection, and autoimmune diseases or disorders. Inhibition of IDO may also be an important treatment strategy for patients with neurological or neuropsychiatric diseases or disorders such as depression. The compounds, compositions and methods herein address the need for new classes of IDO modulators.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycylic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, a wavy line, "⌇⌇⌇", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C (NH$_2$)=NR', —S(O)R', —S(O)$_2$R', —S(O)$_2$NR' R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C (NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—

(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. For example, the structures of hydroxyamidines are shown as a single isomer. The depiction shown herein is meant to include both isomers, as well as forms of the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of IDO, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of IDO or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an IDO inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of and IDO inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

As used herein, the terms "IDO inhibitor", "IDO blocker" and terms similar thereto refer to agents capable of inhibiting the activity of IDO, thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site; "a noncompetitive IDO Inhibitor" is a compound that reversibly inhibits IDO enzyme activity at a non-catalytic site; and "an irreversible IDO inhibitor" is a compound that irreversibly eliminates IDO enzyme activity by forming a covalent bond (or other stable means of inhibiting enzyme function) with the enzyme. A number of IDO inhibitors are commercially available (e.g., 5-Br-4-Cl-indoxyl 1,3-diacetate and 1-methyl-DL-tryptophan (1 MT); both available from Sigma-Aldrich, St. Louis, Mo.) and may be used as, for example, "tool" or "reference" compounds The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of IDO, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Indoleamine 2,3-dioxygenase

As previously alluded to, IDO is an immune regulatory enzyme that is normally expressed in tumor cells and in activated immune cells. IDO is one of several immune response checkpoints that are involved in tumor immune escape; thus, IDO inhibitors disrupt mechanisms by which tumors evade the body's normal immune system.

IDO down-regulates the immune response mediated through oxidation of tryptophan. This results in inhibition of T-cell activation and induction of T-cell apoptosis, creating an environment in which tumor-specific cytotoxic T lymphocytes are rendered functionally inactive or are no longer able to attack a subject's cancer cells. Therefore, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

The expression of IDO is modulated by a complex array of signals, thus implicating a number of different mechanisms of actions. For example, IDO may be induced by inhibition of DNA methyl transferases or histone deacetylases. The NF-κB signaling pathway has also been implicated in IDO function. Inhibiting NF-kB activity blocks IDO expression and produces robust anti-tumor responses that are both T cell- and IDO-dependent; alternatively, NF-κB activation (which may be effected by various factors such as interferon-γR1/-γR2 signaling and toll-like-receptor activation) induces IDO gene expression.

Other mechanisms are involved with modulation of IDO function. By way of example, inhibitors of reactive oxidative species (ROS) may effect stabilization of IDO; IDO levels may be modulated by inhibition or activation of pathways that are both downstream and upstream of IDO; and activation of interferon-γ can activate an autocrine induction of IDO.

Studies indicate that the IDO pathway is active in many cancers, both within tumor cells as a direct defense against T cell attack, and also within antigen-presenting cells (APCs) in tumor-draining lymph nodes resulting in peripheral tolerance to tumor-associated antigens (TAAs). Cancers may use the IDO pathway to facilitate survival, growth, invasion, and metastasis of malignant cells expressing TAAs that might otherwise be recognized and attacked by the immune system.

As alluded to herein, tryptophan catabolism in tumor tissue by the rate-limiting enzyme IDO provides an opportunity for the use of IDO inhibitors as a therapeutic alternative to, or an additive with, conventional chemotherapy. However, certain cancers are capable of catabolizing tryptophan but are largely IDO-negative. Recent studies indicate that the alternative enzymatic pathway of tryptophan catabolism involving tryptophan-2,3-dioxygenase (TDO) is also relevant in cancer. TDO, which is considered responsible for regulating systemic tryptophan levels in the liver, is constitutively expressed in some cancers and is also capable of suppressing antitumor immune responses (See e.g., Platten, M. et al., Cancer Res 72(21):5435-40 (Nov. 1, 2012)).

IDO is expressed in a wide variety of human tumors and tumor cell lines as well as in host APCs, which correlates with a worse clinical prognosis. Therefore, inhibition of IDO may improve survival in cancer patients with IDO-mediated immunosuppression. In comparison, TDO is expressed in a wide variety of human tumors and tumor cell lines, and expression of TDO is evident in advanced human glioblastomas. The identification of tumors expressing high levels of IDO or TDO may allow more selective inhibition of the tryptophan-regulated immunosuppressive pathways. Alternatively, compounds inhibiting both IDO and TDO could provide the greatest coverage to prevent tumor escape by compensatory expression of the other tryptophan-degrading enzyme. Therefore, the use of dual IDO/TDO inhibitors or combinations of IDO- and TDO-specific inhibitors may prove to be a superior treatment alternative in immunotherapy of cancer to block immunosuppression mediated by tryptophan metabolism.

Although a precise understanding of the underlying mechanism of action by which the compounds of the present invention effect their activity is not required to practice the invention, the compounds (or a subset thereof) are believed to inhibit IDO function. Alternatively, the compounds (or a subset thereof) may inhibit TDO function. The compounds (or a subset thereof) may also have inhibitory activity on both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

Identification of IDO Inhibitors Possessing Desirable Characteristics

The present invention is drawn, in part, to the identification of inhibitors of IDO with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

Compounds of the Invention

As noted above, the present invention provides compounds represented by formula (I):

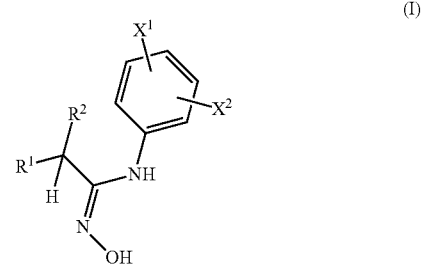

or a pharmaceutically acceptable salt, hydrate or solvate thereof.

In formula (I), $X^1$ and $X^2$ represent independently selected substituents selected from hydrogen, halogen, CN, $SO_2NH_2$, $NHSO_2CH_3$, $NHSO_2CF_3$, $OCF_3$, $SO_2CH_3$, $SO_2CF_3$, optionally substituted $C_1$-$C_4$ alkyl, optionally substituted $C_1$-$C_4$ alkoxy, $C_1$-$C_4$ haloalkyl, cyclopropyl and $CONH_2$. Additionally, when $X^1$ and $X^2$ are on adjacent vertices of the phenyl ring they are optionally joined together to form an optionally substituted 5- or 6-member aromatic or aliphatic ring containing 0, 1, or 2 heteroatoms.

$R^1$ and $R^2$ are independently selected from the group consisting of hydrogen, optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, hydroxyl, optionally substituted aryl, and optionally substituted heteroaryl; and $R^1$ and $R^2$ are optionally joined together to form an optionally substituted $C_3$-$C_8$ cycloalkyl or optionally substituted 3- to 7-membered cycloheteroalkyl with the proviso that $R^1$ and $R^2$ do not join together to form an unsubstituted cyclohexane ring, and at least one of $R^1$ and $R^2$ is other than hydrogen.

In one group of embodiments, a compound is provided having formula (Ia):

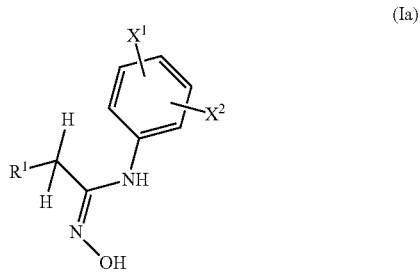

(Ia)

wherein, $X^1$ and $X^2$ are as provided for formula (I), and $R^1$ is selected from optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, optionally substituted aryl, and optionally substituted heteroaryl. In selected embodiments, $R^1$ is selected from optionally substituted $C_3$-$C_8$ cycloalkyl, optionally substituted $C_3$-$C_8$ cycloalkyl-$C_1$-$C_4$ alkyl, and optionally substituted 3- to 7-membered cycloheteroalkyl.

In another group of embodiments, a compound is provided having the formula (Ib):

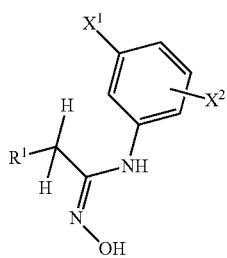

(Ib)

wherein, $X^1$ is selected from halogen, CN, $OCF_3$, $SO_2CH_3$, $SO_2CF_3$, optionally substituted $C_1$-$C_4$ alkyl, optionally substituted $C_1$-$C_4$ alkoxy, $C_1$-$C_4$ haloalkyl, and cyclopropyl; $X^2$ is selected from hydrogen, halogen, CN, $SO_2NH_2$, $NHSO_2CH_3$, $NHSO_2CF_3$, $OCF_3$, $SO_2CH_3$, $SO_2CF_3$, optionally substituted $C_1$-$C_4$ alkyl, optionally substituted $C_1$-$C_4$ alkoxy, $C_1$-$C_4$ haloalkyl, cyclopropyl and $CONH_2$; and $R^1$ is selected from optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, optionally substituted aryl, and optionally substituted heteroaryl. In certain selected embodiments of formula (Ib), $R^1$ is selected from optionally substituted $C_3$-$C_8$ cycloalkyl, optionally substituted $C_3$-$C_8$ cycloalkyl-$C_1$-$C_4$ alkyl, and optionally substituted 3- to 7-membered cycloheteroalkyl.

In one group of selected embodiments, a compound of any of the above embodiments referring to formulae (I), (Ia) and (Ib) is provided wherein $X^2$ is hydrogen.

In another group of selected embodiments, a compound of any of the above embodiments referring to formulae (I), (Ia) and (Ib) is provided wherein $R^1$ is selected from optionally substituted $C_3$-$C_6$ cycloalkyl and optionally substituted $C_3$-$C_6$ cycloalkyl-$C_1$-$C_4$ alkyl.

In yet another group of selected embodiments, a compound of any of the above embodiments referring to formulae (I), (Ia) and (Ib) is provided wherein $R^1$ is selected from optionally substituted 4- to 6-membered cycloheteroalkyl.

In still another group of selected embodiments, a compound of any of the above embodiments referring to formulae (I), (Ia) and (Ib) is provided wherein $R^1$ is selected from:

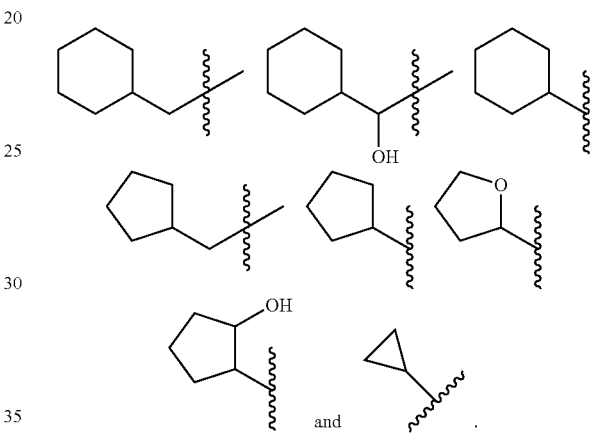

In another group of selected embodiments, a compound of any of the above embodiments referring to formulae (I) and (Ia) is provided wherein $R^1$ is selected from methyl, ethyl, 1-propyl, 2-propyl, 1-butyl, 2-methylpropyl, 3-hydroxypropyl, 1-pentyl and 1,1-dimethylethyl.

In another group of selected embodiments, a compound of formulae (I) is provided wherein $X^1$ is halogen or $C_1$-$C_4$ haloalkyl; $X^2$ is hydrogen or halogen; and $R^1$ is selected from optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, and optionally substituted 3- to 7-membered cycloheteroalkyl; or $R^1$ and $R^2$ are optionally joined together to form an optionally substituted cyclobutyl, cyclopentyl or cycloheptyl. Still further selected embodiments are those wherein $R^1$ is selected from optionally substituted $C_3$-$C_6$ cycloalkyl and optionally substituted $C_3$-$C_6$ cycloalkyl-$C_1$-$C_4$ alkyl. In other selected embodiments, $R^1$ is selected from the group consisting of optionally substituted 4- to 6-membered cycloheteroalkyl. In still other selected embodiments, $R^1$ is selected from the group consisting of

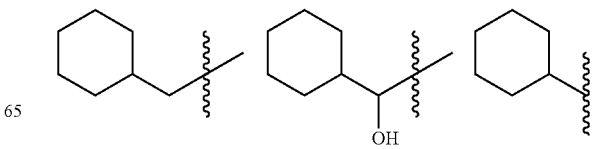

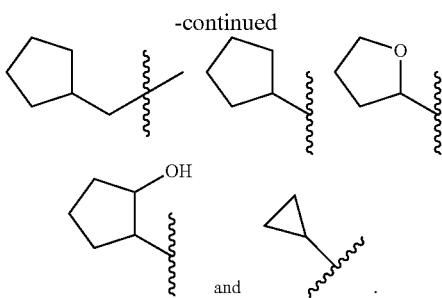

In yet other selected embodiments, $R^1$ is selected from the group consisting of methyl, ethyl, 1-propyl, 2-propyl, 1-butyl, 2-methylpropyl, 3-hydroxypropyl, 1-pentyl and 1,1-dimethylethyl.

In another aspect, the present invention provides compounds represented by formula (II):

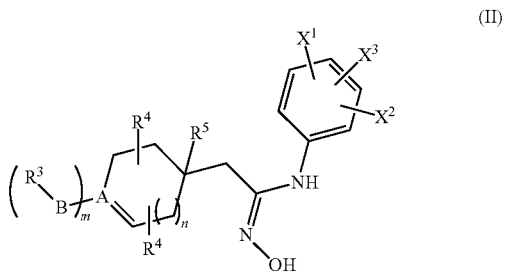

(II)

or a pharmaceutically acceptable salt, hydrate or solvate thereof.

In formula (II), the dashed line represents a single or double bond between ring vertices; $X^1$, $X^2$ and $X^3$ are substituents independently selected from hydrogen, halogen, CN, $SO_2NH_2$, $NHSO_2CH_3$, $NHSO_2CF_3$, $OCF_3$, $SO_2CH_3$, $SO_2CF_3$, optionally substituted $C_1$-$C_4$ alkyl, optionally substituted $C_1$-$C_4$ alkoxy, $C_1$-$C_4$ haloalkyl, cyclopropyl and $CONH_2$; and when $X^1$ and $X^2$ are on adjacent vertices of the phenyl ring they are optionally joined together to form an optionally substituted 5- or 6-member aromatic or aliphatic ring containing 0, 1, or 2 heteroatoms; $R^3$ is selected from hydrogen, optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, optionally substituted aryl, and optionally substituted heteroaryl; B is selected from a bond, C(O), optionally substituted $C_1$-$C_8$ alkyl and optionally substituted $C_2$-$C_8$ heteroalkyl; A is selected from O, C, $CR^4$, N and $NR^4$; each $R^4$ is independently selected from hydrogen, $C_1$-$C_4$ alkyl, $C_1$-$C_4$ alkoxy, $C_1$-$C_4$ haloalkyl and hydroxyl; $R^5$ is selected from hydrogen, hydroxyl, $CH_3$, and $CF_3$; the subscript m is 0, when A is O, and m is 1 when A is selected from N, $NR^4$ and $CR^4$; and the subscript n is 0 or 1, indicating the ring having A as a ring vertex is either a five-membered or six-membered ring.

In one group of embodiments, compounds are provided having formula (IIa):

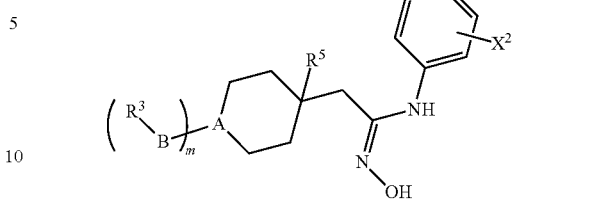

(IIa)

wherein, $X^1$ is selected from halogen, CN, $OCF_3$, $SO_2CH_3$, $SO_2CF_3$, cyclopropyl, optionally substituted $C_1$-$C_4$ alkyl, optionally substituted $C_1$-$C_4$ alkoxy and $C_1$-$C_4$ haloalkyl; $X^2$ is selected from hydrogen, halogen, CN, $OCF_3$, $SO_2NH_2$, $NHSO_2CH_3$, $NHSO_2CF_3$, $SO_2CH_3$, $SO_2CF_3$, cyclopropyl, optionally substituted $C_1$-$C_4$ alkyl, optionally substituted $C_1$-$C_4$ alkoxy, $C_1$-$C_4$ haloalkyl and $CONH_2$; $R^3$ is selected from hydrogen, optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, optionally substituted aryl, and optionally substituted heteroaryl; B is selected from a bond, optionally substituted $C_1$-$C_8$ alkyl and optionally substituted $C_2$-$C_8$ heteroalkyl; A is selected from O, $CR^4$, N and $NR^4$; $R^4$ is selected from hydrogen, $C_1$-$C_4$ alkyl, $C_1$-$C_4$ alkoxy, $C_1$-$C_4$ haloalkyl, or hydroxyl; and $R^5$ is selected from hydrogen, hydroxyl, $CH_3$, or $CF_3$; and the subscript m has the meaning provided with reference to formula (II).

In another group of embodiments, compounds are provided having formula (IIb):

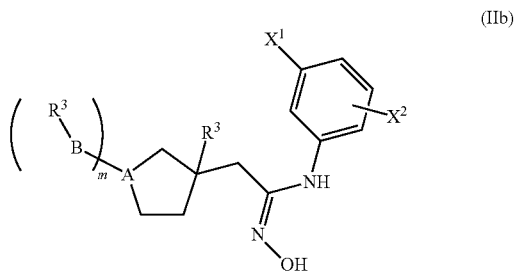

(IIb)

wherein, $X^1$ is selected from halogen, CN, $OCF_3$, $SO_2CH_3$, $SO_2CF_3$, cyclopropyl, optionally substituted $C_1$-$C_4$ alkyl, optionally substituted $C_1$-$C_4$ alkoxy and $C_1$-$C_4$ haloalkyl; $X^2$ is selected from hydrogen, halogen, CN, $OCF_3$, $SO_2NH_2$, $NHSO_2CH_3$, $NHSO_2CF_3$, $SO_2CH_3$, $SO_2CF_3$, cyclopropyl, optionally substituted $C_1$-$C_4$ alkyl, optionally substituted $C_1$-$C_4$ alkoxy, $C_1$-$C_4$ haloalkyl and $CONH_2$; $R^3$ is selected from hydrogen, optionally substituted $C_1$-$C_8$ alkyl, optionally substituted $C_3$-$C_8$ cycloalkyl, optionally substituted $C_3$-$C_8$ cycloalkyl-$C_1$-$C_4$ alkyl, optionally substituted 3- to 7-membered cycloheteroalkyl, optionally substituted $C_1$-$C_4$ haloalkyl, optionally substituted aryl, and optionally substituted heteroaryl; B is selected from a bond, optionally substituted $C_1$-$C_8$ alkyl and optionally substituted $C_2$-$C_8$ heteroalkyl; A is selected from O, $CR^4$, N and $NR^4$; $R^4$ is selected from the group consisting hydrogen, $C_1$-$C_3$ alkyl, $C_1$-$C_3$ alkoxy, $C_1$-$C_3$ haloalkyl and hydroxyl; $R^5$ is selected from the group consisting hydrogen, hydroxyl, $CH_3$, and $CF_3$.

In one group of selected embodiments, a compound of any of the above embodiments referring to formulae (II), (IIa) and (IIb) is provided wherein A is O.

In another group of selected embodiments, a compound of any of the above embodiments referring to formulae (II), (IIa) and (IIb) is provided wherein A is N.

In yet another group of selected embodiments, a compound of any of the above embodiments referring to formulae (II), (IIa) and (IIb) is provided wherein A is $CR^4$.

In still another group of selected embodiments, a compound of any of the above embodiments referring to formulae (II), (IIa) and (IIb) is provided wherein A is $NR^4$.

In another group of selected embodiments, a compound of any of the above embodiments referring to formulae (II), (IIa) and (IIb) is provided wherein $X^2$ is hydrogen.

In yet another group of selected embodiments, a compound of any of the above embodiments referring to formulae (II), (IIa) and (IIb) is provided wherein $X^1$ is halogen and $X^2$ is hydrogen.

In one group of selected embodiments, any one compound of Table 1 is provided.

In another group of selected embodiments, any one compound of Table 1 is provided having an activity level identified as "A" or "B".

In another group of selected embodiments, any one compound of Table 1 is provided having an activity level identified as "A".

Methods of Synthesis

The compounds described herein can be prepared by a variety of methods. One scheme illustrating a route to the compounds is provided in FIG. 1.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Therapeutic and Prophylactic Uses

The present invention contemplates the use of the IDO inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-Related Disorders.

In accordance with the present invention, an IDO inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In some embodiments, the present invention provides methods for treating a proliferative condition, cancer, tumor, or precancerous condition with an IDO inhibitor and at least one additional therapeutic or diagnostic agent, examples of which are set forth elsewhere herein.

Immune- and Inflammatory-Related Disorders.

As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of IDO function may also play a role in immunologic tolerance and prevention of fetal rejection in utero.

In some embodiments, an IDO inhibitor described herein can be combined with an immunosuppressive agent to reduce the number of immune effector cells.

Some of the aforementioned diseases, disorders and conditions for which an IDO inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Subjects suffering from multiple sclerosis (MS), a seriously debilitating autoimmune disease comprising multiple areas of inflammation and scarring of the myelin in the brain and spinal cord, may be particularly helped by the IDO inhibitors described herein, as current treatments only alleviate symptoms or delay the progression of disability.

Similarly, the IDO inhibitors may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Viral-Related Disorders.

The present invention contemplates the use of the IDO inhibitors in the treatment and/or prevention of any viral disease, disorder or condition for which treatment with an IDO inhibitor may be beneficial. In particular embodiments, the viral disorder is a chronic viral disorder. Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Bacterial- and Parasitic-Related Disorders.

Embodiments of the present invention contemplate the administration of the IDO inhibitors described herein to a subject for the treatment of a bacterial infection, for example, a *Mycobacterium* infection (e.g., *Mycobacterium leprae* or *Mycobacterium tuberculosis*) or an infection caused by *Listeria monocytogenes* or *Toxplasma gondii*. Other embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale*, or *Plasmodium malariae*. Frequently, anti-parasitic therapy is administered prophylactically (e.g., before a subject travels to an area with a high frequency of parasitic infection).

Pharmaceutical Compositions

The IDO inhibitors of the present invention may be in the form of compositions suitable for administration to a subject. In general, such compositions are "pharmaceutical compositions" comprising an IDO inhibitor(s) and one or more pharmaceutically acceptable or physiologically acceptable diluents, carriers or excipients. In certain embodiments, the IDO inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of IDO function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The pharmaceutical compositions typically comprise a therapeutically effective amount of an IDO inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver and IDO inhibitor, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein.

One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the IDO inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IDO inhibitors contemplated by the present invention may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present invention contemplates the administration of IDO inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), sublingual and inhalation. Depot injections, which are generally administered subcutaneously or intramuscularly, may also be utilized to release the IDO inhibitors disclosed herein over a defined period of time.

Particular embodiments of the present invention contemplate oral administration.

Combination Therapy

The present invention contemplates the use of IDO inhibitors in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IDO inhibitors are administered or applied sequentially, e.g., where one agent is administered prior to one or more other agents. In other embodiments, the IDO inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The IDO inhibitors of the present invention may be used in combination with at least one other (active) agent in any manner appropriate under the circumstances. In one embodiment, treatment with the at least one active agent and at least one IDO inhibitor of the present invention is maintained over a period of time. In another embodiment, treatment with the at least one active agent is reduced or discontinued (e.g., when the subject is stable), while treatment with an IDO inhibitor of the present invention is maintained at a constant dosing regimen. In a further embodiment, treatment with the at least one active agent is reduced or discontinued (e.g., when the subject is stable), while treatment with an IDO inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the IDO inhibitor of the present invention is increased (e.g., higher dose, more frequent dosing or longer treatment regimen). In yet another embodiment, treatment with the at least one active agent is maintained and treatment with the IDO inhibitor of the present invention is reduced or discontinued (e.g., lower dose, less frequent dosing or shorter treatment regimen). In yet another embodiment, treatment with the at least one active agent and treatment with the IDO inhibitor of the present invention are reduced or discontinued (e.g., lower dose, less frequent dosing or shorter treatment regimen).

Oncology-Related Disorders.

The present invention provides methods for treating and/or preventing a proliferative condition, cancer, tumor, or precancerous disease, disorder or condition with an IDO inhibitor and at least one additional therapeutic agent, such as radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Chemotherapeutic agents also include signal transduction inhibitors (STI). The term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors.

Additional treatment modalities that may be used in combination with an IDO inhibitor include a cytokine or cytokine antagonist, such as IL-12, IFN, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

Cardiovascular Diseases.

The present invention provides methods for treating and/or preventing certain cardiovascular- and/or metabolic-related diseases, disorders and conditions, as well as disorders associated therewith, with an IDO inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the IDO inhibitors described herein include various supplements and herbs (e.g., garlic, policosanol, and guggul). The present invention encompasses pharmaceutically acceptable salts, acids or derivatives of any of the above.

Immune- and Inflammatory-Related Disorders.

The present invention provides methods for treating and/or preventing immune- and/or inflammatory-related diseases, disorders and conditions, as well as disorders associated therewith, with an IDO inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-1β, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFα-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IDO inhibitors described herein include interferon-β1a (AVONEX); interferon-β1b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Immune Checkpoint Inhibitors.

The present invention contemplates the use of the inhibitors of IDO function described herein in combination with additional immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms. In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not overexpressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor—ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of IDO function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are also available for the treatment of cancer, including for example nivolumab (Bristol-Myers Squibb) and pembroluzimab (Merck), and anti-PDLL antibodies are also being evaluated (e.g., MPDL3280A (Roche)). Nivolumab (Opdivo®) has shown promise in patients with melanoma, lung and kidney cancer, as well as multiple other malignancies.

In one aspect of the present invention, the claimed IDO inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the claimed IDO inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the IDO inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, the claimed IDO inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Viral Diseases.

The present invention provides methods for treating and/or preventing viral diseases, disorders and conditions, as well as disorders associated therewith, with an IDO inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantadine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an IDO inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention encompasses pharmaceutically acceptable salts, acids or derivatives of any of the above.

Parasitic Disorders. The present invention contemplates the use of the inhibitors of IDO function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

The present invention encompasses pharmaceutically acceptable salts, acids or derivatives of any of the above.

Bacterial Infections.

Embodiments of the present invention contemplate the use of the IDO inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

The present invention encompasses pharmaceutically acceptable salts, acids or derivatives of the agents (and members of the classes of agents) set forth above.

Dosing

The IDO inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IDO inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired IDO inhibitor is contained in a "unit dosage form". The phrase "unit dosage form" refers to physically discrete units, each unit containing a predetermined amount of the IDO inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising an IDO inhibitor, and pharmaceutical compositions thereof. The kits are generally in the form of a physical structure housing various components, as described below, and may be utilized, for example, in practicing the methods described above.

A kit can include one or more of the IDO inhibitors disclosed herein (provided in, e.g., a sterile container), which may be in the form of a pharmaceutical composition suitable for administration to a subject. The IDO inhibitors can be provided in a form that is ready for use (e.g., a tablet or capsule) or in a form requiring, for example, reconstitution or dilution (e.g., a powder) prior to administration. When the IDO inhibitors are in a form that needs to be reconstituted or diluted by a user, the kit may also include diluents (e.g., sterile water), buffers, pharmaceutically acceptable excipients, and the like, packaged with or separately from the IDO inhibitors. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook and Russell (2001) Molecular Cloning, $3^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., Diabetes 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/l L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Western Blot Analyses.

Groups of 1,000-1,200 islets incubated for 24 h in Miami medium in the presence of cytokines can be harvested and sonicated in PBS as above, and 50 µg protein samples can be electrophoresed on 10% SDS-PAGE gels. COST cells ($0.6 \times 10^6$ cells/60 mm3 petri dish) transfected with human-IDO plasmid (3 µg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-$STAT_{1\alpha}$ p91, and $STAT_{1\alpha}$ p91 (1:500; Zymed, San Francisco, Calif.). Immunoreactive proteins can be visualized with ECL Plus Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO.

Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/1 Tris and 1 mmol/1 EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay.

cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K., et al. (2000) Prot. Exp. Purif. 19:22-29). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-Based Assay.

COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 µg/mL tryptophan can be added together with inhibitor. The reaction can be stopped at 5 hours and the supernatant removed and spectraphotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation.

A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

EXAMPLES

General Methods:

Those skilled in the art will recognize that there are a variety of methods available to synthesize molecules represented in the claims. Three examples of useful methods for synthesizing compounds represented in the claims are shown below (equations i, ii, and iii). In the first example an aniline is metalated (with butyllithium for example). Addition of the metal anilide to an alkylnitro compound then gives the hydroxyamidines of the invention. In a second example, amide formation using standard methods is followed by chlorination using POCl$_3$, PCl$_5$, SOCl$_2$ or the like, followed by addition of hydroxylamine to give the hydroxyamidines of the invention. A third method also passes through an initial amide, followed by thionation with a suitable thionating reagent (such as Lawesson's reagent) and then S-alkylation (representative alkylating agents include methyl iodide or dimethylsulfate) followed by addition of hydroxyl amine to give the compounds of the invention. Common synthetic strategies may be employed to further elaborate compounds of the invention. One skilled in the art will recognize that the timing of the introduction of the hydroxyamidine can vary, and may be the first, last, or intermediate transformation in the preparation of a given compound.

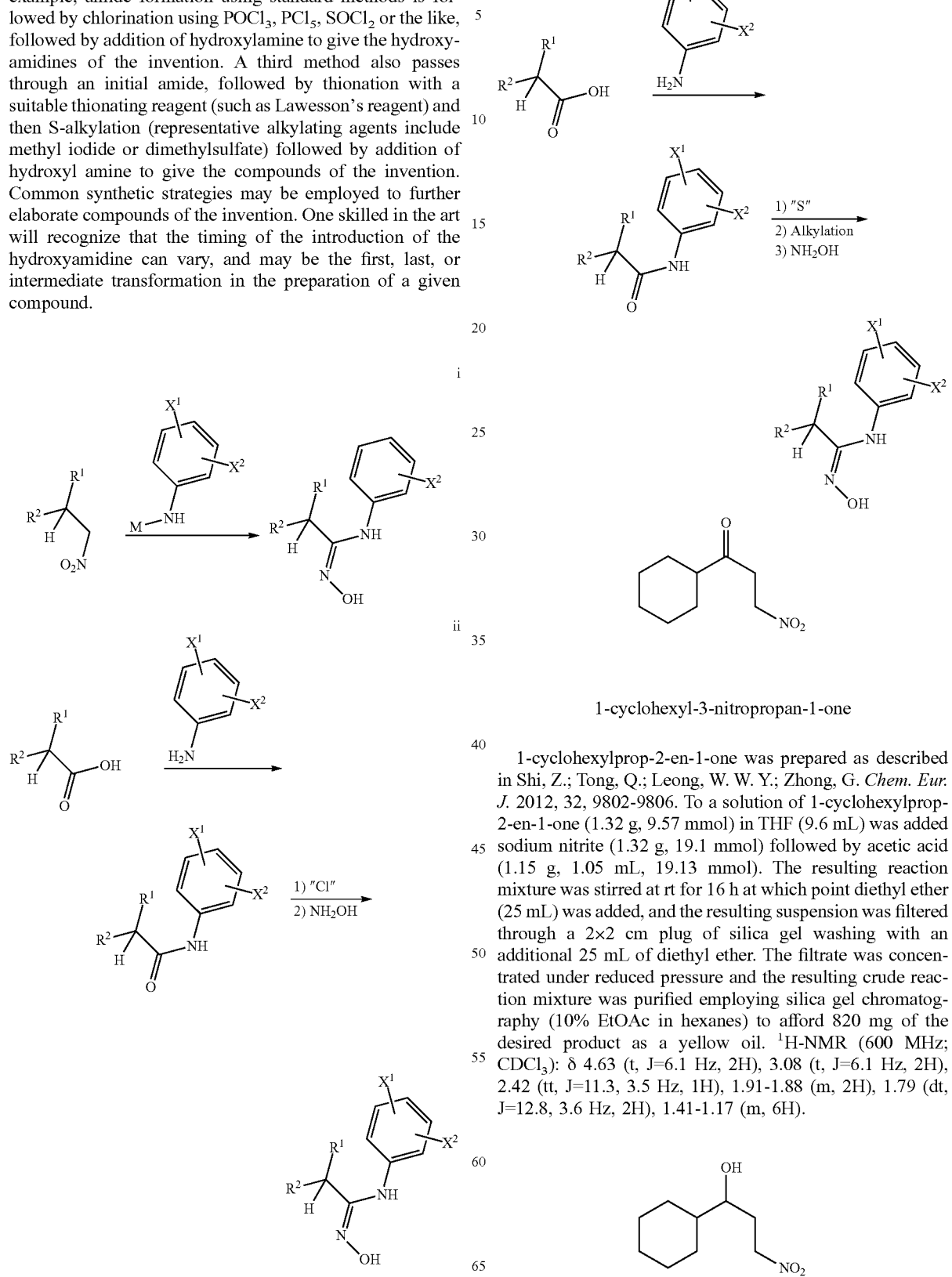

1-cyclohexyl-3-nitropropan-1-one 1-cyclohexylprop-2-en-1-one was prepared as described in Shi, Z.; Tong, Q.; Leong, W. W. Y.; Zhong, G. *Chem. Eur. J.* 2012, 32, 9802-9806. To a solution of 1-cyclohexylprop-2-en-1-one (1.32 g, 9.57 mmol) in THF (9.6 mL) was added sodium nitrite (1.32 g, 19.1 mmol) followed by acetic acid (1.15 g, 1.05 mL, 19.13 mmol). The resulting reaction mixture was stirred at rt for 16 h at which point diethyl ether (25 mL) was added, and the resulting suspension was filtered through a 2×2 cm plug of silica gel washing with an additional 25 mL of diethyl ether. The filtrate was concentrated under reduced pressure and the resulting crude reaction mixture was purified employing silica gel chromatography (10% EtOAc in hexanes) to afford 820 mg of the desired product as a yellow oil. $^1$H-NMR (600 MHz; CDCl$_3$): δ 4.63 (t, J=6.1 Hz, 2H), 3.08 (t, J=6.1 Hz, 2H), 2.42 (tt, J=11.3, 3.5 Hz, 1H), 1.91-1.88 (m, 2H), 1.79 (dt, J=12.8, 3.6 Hz, 2H), 1.41-1.17 (m, 6H).

1-cyclohexyl-3-nitropropan-1-ol

To a solution of 1-cyclohexyl-3-nitropropan-1-one (3.70 g, 20.0 mmol) in EtOH (100 mL) at 0° C. was added NaBH₄ portion-wise over 5 min. The resulting reaction mixture was stirred for 30 min at 0° C. at which point saturated NH₄Cl solution was added dropwise. The heterogeneous suspension was diluted with EtOAc (50 mL) and the layers were separated. The aqueous layer was extracted with EtOAc (3×50 mL). The combined organic extracts were dried over anhydrous MgSO₄, filtered, and concentrated under reduced pressure. The resulting crude reaction mixture was purified employing silica gel chromatography (10 to 50% EtOAc in hexanes) to afford the desired product as a yellow oil. $^1$H-NMR (400 MHz; CDCl₃): δ 4.61-4.49 (m, 2H), 3.44-3.41 (m, 1H), 2.28-2.20 (m, 1H), 1.98 (dddd, J=14.4, 10.3, 6.7, 5.7 Hz, 1H), 1.83-1.73 (m, 4H), 1.69-1.64 (m, 2H), 1.37-0.93 (m, 6H).

General Procedure A: Preparation of Hydroxyamidines

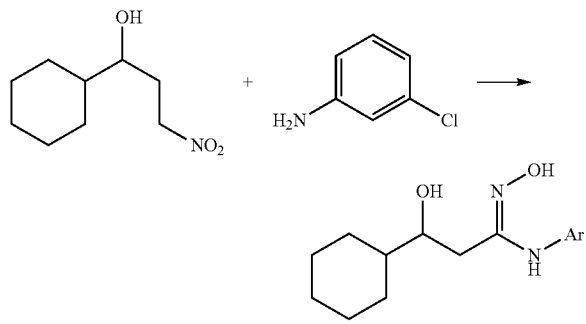

Hydroxyamidines were prepared as generally described in Sanguineti, G.; Le, H. V.; Ganem, B. *Tetrahedron*, 2011, 67, 10208-10211. To a solution of substituted aniline (1.2 mmol) in THF (1.0 mL) at −78° C. was added a solution of n-BuLi (480 μL, 1.2 mmol, 2.5M in hexanes). The resulting reaction mixture became heterogeneous and was allowed to warm to rt over 30 min. The reaction mixture was cooled to 0° C. and 1-cyclohexyl-3-nitropropan-1-ol (56 mg, 0.3 mmol) was added dropwise. The resulting suspension was heated to 65° C. for 2 h at which point TLC analysis indicated complete consumption of the nitroalkane. The reaction mixture was cooled to 0° C. and was diluted with saturated NH₄Cl solution (10 mL), EtOAc (10 mL) and stirred for 5 min. The layers were separated, and the aqueous layer was extracted with EtOAc (3×15 mL). The combined organic extracts were dried over anhydrous MgSO₄, filtered, and concentrated under reduced pressure. The crude reaction mixture was purified employing silica gel chromatography to afford the desired product.

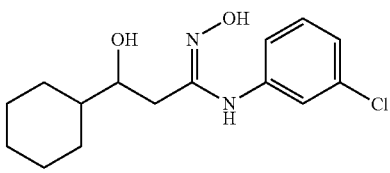 [SMILES: O/N=C(/CC(O)C1CCCCC1)Nc1cccc(Cl)c1]

(Z)—N-(3-chlorophenyl)-3-cyclohexyl-N',3-dihydroxypropanimidamide

Prepared using General Procedure A employing 56 mg 1-cyclohexyl-3-nitropropan-1-ol, and 154 mg 3-chloroaniline. Purified using silica gel chromatography (0 to 5% MeOH in CH₂Cl₂) to afford the desired product as an oil (33 mg, 37%). $^1$H-NMR (600 MHz; CDCl₃): δ 7.22 (t, J=8.0 Hz, 1H), 7.11 (dd, J=8.0, 1.1 Hz, 1H), 7.05 (t, J=2.0 Hz, 1H), 6.92 (dd, J=8.0, 1.2 Hz, 1H), 3.54 (ddd, J=10.1, 6.0, 2.0 Hz, 1H), 2.57 (dd, J=15.4, 2.1 Hz, 1H), 2.29 (dd, J=15.5, 10.2 Hz, 1H), 1.75-1.65 (m, 4H), 1.57 (dd, J=43.6, 12.4 Hz, 2H), 1.32-1.01 (m, 4H), 0.91 (dddt, J=16.3, 12.3, 8.3, 4.1 Hz, 2H). m/z 297.2 (M+H⁺).

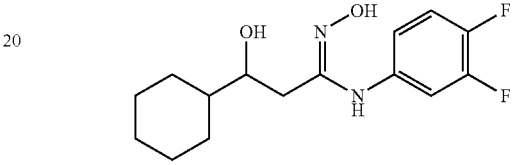

(Z)-3-cyclohexyl-N-(3,4-difluorophenyl)-N',3-dihydroxypropanimidamide

Prepared using General Procedure A employing 56 mg 1-cyclohexyl-3-nitropropan-1-ol, and 155 mg 3,4-difluoroaniline. Purified using silica gel chromatography (0 to 5% MeOH in CH₂Cl₂) to afford the desired product as a tan oil (56 mg, 62%). $^1$H-NMR (600 MHz; CDCl₃): δ 7.10 (q, J=9.2 Hz, 1H), 6.92 (ddd, J=10.9, 7.1, 2.6 Hz, 1H), 6.81-6.78 (m, 1H), 3.53-3.51 (m, 1H), 2.47 (dd, J=15.4, 1.6 Hz, 1H), 2.23 (dd, J=15.4, 10.3 Hz, 1H), 1.73-1.65 (m, 4H), 1.55 (dd, J=59.4, 12.3 Hz, 2H), 1.29-0.97 (m, 4H), 0.93-0.85 (m, 2H). m/z 299.2 (M+H⁺).

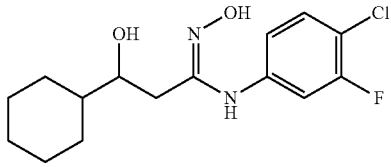 [SMILES: O/N=C(/CC(O)C1CCCCC1)Nc1ccc(Cl)c(F)c1]

(Z)—N-(4-chloro-3-fluorophenyl)-3-cyclohexyl-N',3-dihydroxypropanimidamide

Prepared using General Procedure A employing 56 mg 1-cyclohexyl-3-nitropropan-1-ol, and 175 mg 4-chloro-3-fluoroaniline. Purified using silica gel chromatography (0 to 5% MeOH in CH₂Cl₂) to afford the desired product as a yellow foam (57 mg, 60%). $^1$H-NMR (600 MHz; CDCl₃): δ 7.30 (t, J=8.4 Hz, 1H), 6.86 (dd, J=10.1, 2.5 Hz, 1H), 6.77 (ddd, J=8.6, 2.4, 0.8 Hz, 1H), 3.55 (ddd, J=10.2, 6.0, 2.0 Hz, 1H), 2.54 (dd, J=15.5, 2.1 Hz, 1H), 2.30 (dd, J=15.5, 10.3 Hz, 1H), 1.75-1.66 (m, 4H), 1.57 (dd, J=50.1, 12.4 Hz, 2H), 1.35-0.97 (m, 4H), 0.96-0.88 (m, 2H). m/z 315.2 (M+H⁺).

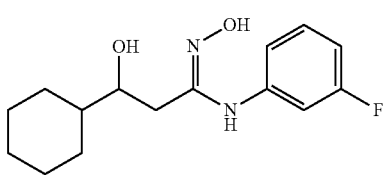 [SMILES: O/N=C(/CC(O)C1CCCCC1)Nc1cccc(F)c1]

(Z)-3-cyclohexyl-N-(3-fluorophenyl)-N',3-dihydroxypropanimidamide

Prepared using General Procedure A employing 56 mg 1-cyclohexyl-3-nitropropan-1-ol, and 133 mg 3-fluoroaniline. Purified using silica gel chromatography (0 to 5% MeOH in $CH_2Cl_2$) to afford the desired product as a yellow oil (43 mg, 51%). $^1$H-NMR (600 MHz; $CDCl_3$): δ 7.30 (t, J=8.4 Hz, 1H), 6.86 (dd, J=10.1, 2.5 Hz, 1H), 6.77 (ddd, J=8.6, 2.4, 0.8 Hz, 1H), 3.55 (ddd, J=10.2, 6.0, 2.0 Hz, 1H), 2.54 (dd, J=15.5, 2.1 Hz, 1H), 2.30 (dd, J=15.5, 10.3 Hz, 1H), 1.75-1.66 (m, 4H), 1.57 (dd, J=50.1, 12.4 Hz, 2H), 1.35-0.97 (m, 4H), 0.96-0.88 (m, 2H). m/z 281.2 (M+H$^+$).

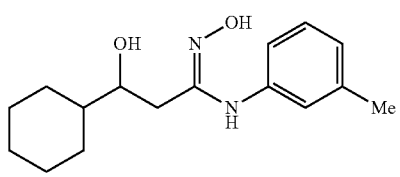 [SMILES: Cc1cccc(N/C(CC(O)C2CCCCC2)=N\O)c1]

(Z)-3-cyclohexyl-N',3-dihydroxy-N-(m-tolyl)propanimidamide

Prepared using General Procedure A employing 56 mg 1-cyclohexyl-3-nitropropan-1-ol, and 107 mg m-toluidine. Purified using silica gel chromatography (0 to 5% MeOH in $CH_2Cl_2$) to afford the desired product as a yellow oil (36 mg, 43%). $^1$H-NMR (600 MHz; $CDCl_3$): δ 7.17 (t, J=7.6 Hz, 1H), 6.94 (d, J=7.6 Hz, 1H), 6.84 (d, J=8.0 Hz, 1H), 3.54 (ddd, J=10.0, 6.0, 2.0 Hz, 1H), 2.55 (dd, J=15.4, 2.0 Hz, 1H), 2.30 (s, 3H), 2.24 (dd, J=15.4, 10.2 Hz, 1H), 1.75-1.62 (m, 4H), 1.54 (dd, J=46.2, 12.4 Hz, 2H), 1.34-0.96 (m, 4H), 0.93-0.84 (m, 2H). m/z 277.3 (M+H$^+$).

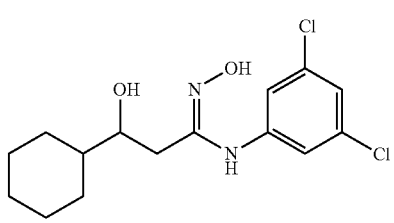 [SMILES: O/N=C(/CC(O)C1CCCCC1)Nc1cc(Cl)cc(Cl)c1]

(Z)-3-cyclohexyl-N-(3,5-dichlorophenyl)-N',3-dihydroxypropanimidamide

Prepared using General Procedure A employing 56 mg 1-cyclohexyl-3-nitropropan-1-ol, and 194 mg 3,5-dichloroaniline. Purified using silica gel chromatography (0 to 5% MeOH in $CH_2Cl_2$) to afford the desired product as an oil (50 mg, 50%). $^1$H-NMR (600 MHz; $CDCl_3$): δ 7.08 (t, J=1.7 Hz, 1H), 6.91 (d, J=1.7 Hz, 2H), 3.50 (dd, J=8.5, 6.1 Hz, 1H), 2.60 (dd, J=15.3, 1.6 Hz, 1H), 2.29 (dd, J=15.3, 10.4 Hz, 1H), 1.73-1.66 (m, 4H), 1.57 (dd, J=37.9, 12.4 Hz, 2H), 1.32-1.05 (m, 4H), 0.93-0.87 (m, 2H). m/z 331.1 (M+H$^+$).

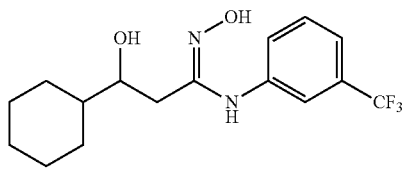 [SMILES: O/N=C(/CC(O)C1CCCCC1)Nc1cccc(C(F)(F)F)c1]

(Z)-3-cyclohexyl-N',3-dihydroxy-N-(3-(trifluoromethyl)phenyl)propanimidamide

Prepared using General Procedure A employing 56 mg 1-cyclohexyl-3-nitropropan-1-ol, and 193 mg 3-(trifluoromethyl)aniline. Purified using silica gel chromatography (0 to 5% MeOH in $CH_2Cl_2$) to afford the desired product as an oil (62 mg, 63%). $^1$H-NMR (600 MHz; $CDCl_3$): δ 7.40 (t, J=7.8 Hz, 1H), 7.37 (d, J=7.7 Hz, 1H), 7.28 (s, 1H), 7.21 (d, J=7.6 Hz, 1H), 3.50 (dd, J=8.1, 7.8 Hz, 1H), 2.60 (d, J=15.2 Hz, 1H), 2.30 (dd, J=15.2, 10.5 Hz, 1H), 1.75-1.62 (m, 4H), 1.54 (dd, J=53.8, 12.3 Hz, 2H), 1.27-1.01 (m, 4H), 0.89-0.81 (m, 2H). m/z 331.2 (M+H$^+$).

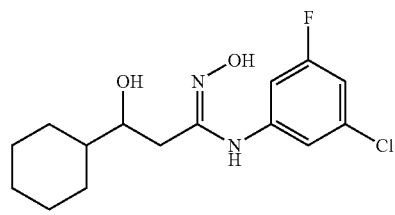 [SMILES: O/N=C(/CC(O)C1CCCCC1)Nc1cc(F)cc(Cl)c1]

(Z)—N-(3-chloro-5-fluorophenyl)-3-cyclohexyl-N',3-dihydroxypropanimidamide

Prepared using General Procedure A employing 56 mg 1-cyclohexyl-3-nitropropan-1-ol, and 175 mg 3-chloro-5-fluoroaniline. Purified using silica gel chromatography (0 to 5% MeOH in $CH_2Cl_2$) to afford the desired product as an oil (53 mg, 56%). $^1$H-NMR (600 MHz; $CDCl_3$): δ 7.40 (t, J=7.8 Hz, 1H), 7.37 (d, J=7.7 Hz, 1H), 7.28 (s, 1H), 7.21 (d, J=7.6 Hz, 1H), 3.50 (dd, J=8.1, 7.8 Hz, 1H), 2.60 (d, J=15.2 Hz, 1H), 2.30 (dd, J=15.2, 10.5 Hz, 1H), 1.75-1.62 (m, 4H), 1.54 (dd, J=53.8, 12.3 Hz, 2H), 1.27-1.01 (m, 4H), 0.89-0.81 (m, 2H). m/z 315.2 (M+H$^+$).

General Procedure B: Preparation of Nitroalkane Substrates

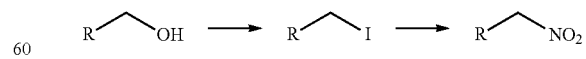

Non-commercial nitroalkanes were prepared from the corresponding alcohols by iodination followed by displacement with silver nitrite: To a solution of $PPh_3$ (2.88 g, 11.0 mmol) and imidazole (1.50 g, 22.0 mmol) at 0° C. in $CH_2Cl_2$ (20 mL) was added $I_2$ (2.78 g, 11.0 mmol). The reaction mixture was stirred for 10 min at which point the alcohol (10.0 mmol) was added dropwise. The reaction mixture was allowed to warm to rt and was stirred for 16 h at which point a solution of Na$_2$S$_2$O$_3$ (2M, 20 mL) was added. The biphasic mixture was stirred 10 min and the layers were separated. The aqueous layer was extracted with CH$_2$Cl$_2$ (3×25 mL) and the combined organic layers were dried over anhydrous MgSO$_4$, filtered, and concentrated under reduced pressure. The resulting crude reaction mixture was dissolved in diethyl ether and filtered through a 4×4 cm plug of silica gel eluting with diethyl ether (150 mL). The filtrate was concentrated under reduced pressure to afford the desired alkyl iodide which was used without further purification. The crude alkyl iodide was dissolved in diethyl ether (20 mL) and silver (I) nitrite (11.0 mmol) was added. The reaction vessel was wrapped in foil to exclude light and was stirred for 24 h at rt. The reaction mixture was diluted with 20 mL diethyl ether and was filtered through a 4×4 cm plug of silica gel eluting with diethyl ether (150 mL). The filtrate was concentrated to afford the crude nitroalkane which was used without further purification.

General Procedure C: Preparation of Hydroxyamidines

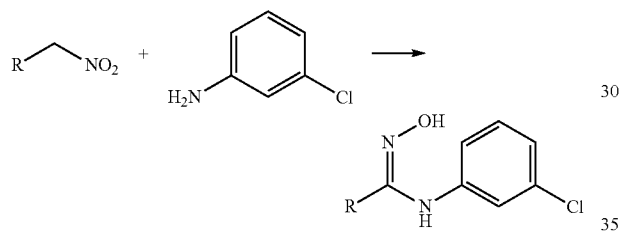

To a solution of 3-chloroaniline (510 mg, 4.0 mmol) in THF at −78° C. was added a solution of n-BuLi (1.6 mL, 4.0 mmol, 2.5M in hexanes). The resulting reaction mixture became heterogeneous and was allowed to warm to rt over 30 min. The reaction mixture was cooled to 0° C. and the nitroalkane (1.0 mmol) was added dropwise. The resulting suspension was heated to 60° C. for 2 h at which point TLC analysis indicated complete consumption of the nitroalkane. The reaction mixture was cooled to 0° C. and was diluted with saturated NH$_4$Cl solution (20 mL), EtOAc (20 mL) and stirred for 5 min. The layers were separated, and the aqueous layer was extracted with EtOAc (3×15 mL). The combined organic extracts were dried over anhydrous MgSO$_4$, filtered, and concentrated under reduced pressure. The crude reaction mixture was purified employing silica gel chromatography to afford the desired product.

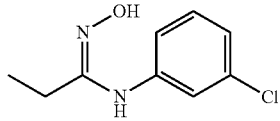

(Z)—N-(3-chlorophenyl)-N'-hydroxypropionimidamide

Prepared using General Procedure C employing 89 mg 1-nitropropane, and 510 mg 3-chloroaniline. Purified using silica gel chromatography (0 to 5% MeOH in CH$_2$Cl$_2$) to afford the desired product as a tan oil (156 mg, 79%). $^1$H-NMR (600 MHz; CDCl$_3$): δ 7.22 (t, J=8.0 Hz, 1H), 7.10 (ddd, J=8.0, 1.9, 0.9 Hz, 1H), 7.06 (t, J=2.0 Hz, 1H), 6.94 (ddd, J=8.0, 2.1, 0.8 Hz, 1H), 2.38 (q, J=7.4 Hz, 2H), 1.03 (t, J=7.4 Hz, 3H). m/z 199.1 (M+H$^+$).

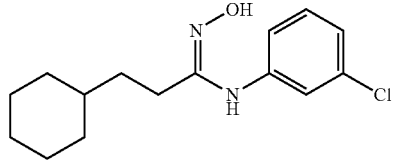 [SMILES: O/N=C(/CCC1CCCCC1)Nc1cccc(Cl)c1]

(Z)—N-(3-chlorophenyl)-3-cyclohexyl-N'-hydroxypropanimidamide

Prepared using General Procedure C employing 171 mg (3-nitropropyl)cyclohexane, and 510 mg 3-chloroaniline. Purified using silica gel chromatography (0 to 5% MeOH in CH$_2$Cl$_2$) to afford the desired product as a yellow oil (156 mg, 56%). $^1$H-NMR (600 MHz; CDCl$_3$): δ 7.23 (t, J=8.0 Hz, 1H), 7.10 (dd, J=8.0, 1.0 Hz, 1H), 7.06 (t, J=2.0 Hz, 1H), 6.94-6.93 (m, 1H), 2.35 (t, J=8.1 Hz, 2H), 1.64-1.57 (m, 4H), 1.33-1.29 (m, 2H), 1.19-1.05 (m, 4H), 0.81-0.75 (m, 2H).

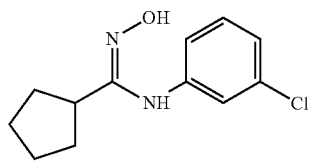 [SMILES: O/N=C(\Nc1cccc(Cl)c1)C1CCCC1]

(Z)—N-(3-chlorophenyl)-N'-hydroxycyclopentanecarboximidamide

Prepared using General Procedure C employing 129 mg (nitromethyl)cyclopentane, and 510 mg 3-chloroaniline. Purified using silica gel chromatography (0 to 5% MeOH in CH$_2$Cl$_2$) to afford the desired product as a red oil (70 mg, 29%). $^1$H-NMR (600 MHz; CDCl$_3$): δ 7.23 (t, J=8.0 Hz, 1H), 7.11 (d, J=8.1 Hz, 1H), 7.08 (s, 1H), 6.97 (d, J=7.9 Hz, 1H), 2.89 (quintet, J=7.7 Hz, 1H), 1.75-1.64 (m, 6H), 1.48 (d, J=4.6 Hz, 2H). m/z 239.1 (M+H$^+$).

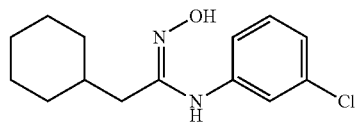 [SMILES: O/N=C(/CC1CCCCC1)Nc1cccc(Cl)c1]

(Z)—N-(3-chlorophenyl)-2-cyclohexyl-N'-hydroxyacetimidamide

Prepared using General Procedure C employing 157 mg (2-nitroethyl)cyclohexane, and 510 mg 3-chloroaniline. Purified using silica gel chromatography (0 to 5% MeOH in CH$_2$Cl$_2$) to afford the desired product as a tan oil (18 mg, 7%). $^1$H-NMR (600 MHz; CDCl$_3$): δ 7.23 (t, J=8.0 Hz, 1H), 7.10 (dd, J=8.0, 0.8 Hz, 1H), 7.05 (s, 1H), 6.92 (dd, J=8.0, 0.9 Hz, 1H), 2.22 (d, J=7.1 Hz, 2H), 1.71-1.56 (m, 8H), 1.15-1.08 (m, 3H).

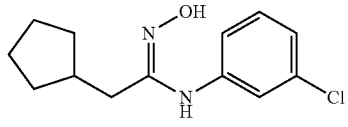 [SMILES: O/N=C(/CC1CCCC1)Nc1cccc(Cl)c1]

(Z)—N-(3-chlorophenyl)-2-cyclopentyl-N'-hydroxy-acetimidamide

Prepared using General Procedure C employing 143 mg (2-nitroethyl)cyclopentane, and 510 mg 3-chloroaniline. Purified using silica gel chromatography (0 to 5% MeOH in CH$_2$Cl$_2$) to afford the desired product as a tan oil (156 mg, 62%). $^1$H-NMR (600 MHz; CDCl$_3$): δ 7.23 (t, J=8.0 Hz, 1H), 7.23 (t, J=8.0 Hz, 1H), 7.09 (d, J=8.0 Hz, 1H), 7.09 (d, J=8.0 Hz, 1H), 7.06 (d, J=1.9 Hz, 1H), 7.06 (d, J=1.9 Hz, 1H), 6.94 (d, J=8.0 Hz, 1H), 6.94 (d, J=8.0 Hz, 1H), 2.35 (d, J=7.4 Hz, 2H), 2.35 (d, J=7.4 Hz, 2H), 1.93 (dt, J=15.3, 7.7 Hz, 1H), 1.93 (dt, J=15.3, 7.7 Hz, 1H), 1.72-1.68 (m, 2H), 1.72-1.68 (m, 2H), 1.59-1.52 (m, 2H), 1.59-1.52 (m, 2H), 1.49-1.45 (m, 2H), 1.49-1.45 (m, 2H), 1.14-1.09 (m, 2H), 1.14-1.09 (m, 2H). m/z 253.2 (M+H$^+$).

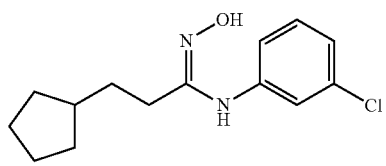 [SMILES: O/N=C(/CCC1CCCC1)Nc1cccc(Cl)c1]

(Z)—N-(3-chlorophenyl)-3-cyclopentyl-N'-hydroxy-propanimidamide

Prepared using General Procedure C employing 157 mg (3-nitropropyl)cyclopentane, and 510 mg 3-chloroaniline. Purified using silica gel chromatography (0 to 5% MeOH in CH$_2$Cl$_2$) to afford the desired product as a tan oil (170 mg, 64%). $^1$H-NMR (600 MHz; CDCl$_3$): δ 7.23 (t, J=8.2 Hz, 1H), 7.10 (d, J=8.0 Hz, 1H), 7.06 (d, J=1.2 Hz, 1H), 6.94 (d, J=8.0 Hz, 1H), 2.37-2.34 (m, 2H), 1.72-1.65 (m, 3H), 1.55-1.49 (m, 2H), 1.49-1.41 (m, 4H), 1.01-0.94 (m, 2H). m/z 267.2 (M+H$^+$).

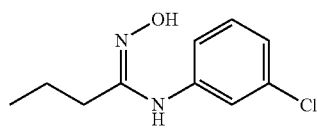

(Z)—N-(3-chlorophenyl)-N'-hydroxybutyrimid-amide

Prepared using General Procedure C employing 103 mg 1-nitrobutane, and 510 mg 3-chloroaniline. Purified using silica gel chromatography (0 to 40% EtOAc in hexanes) to afford the desired product as a yellow oil. $^1$H-NMR (600 MHz; CDCl$_3$): δ 7.23 (t, J=8.0 Hz, 1H), 7.11-7.09 (m, 1H), 7.06 (t, J=2.0 Hz, 1H), 6.94 (dt, J=8.0, 1.0 Hz, 1H), 2.33 (t, J=7.6 Hz, 2H), 1.49-1.43 (m, 2H), 0.88 (t, J=7.4 Hz, 3H); m/z 213.1 (M+H$^+$).

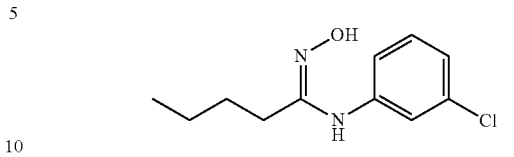

(Z)—N-(3-chlorophenyl)-N'-hydroxypentanimid-amide

Prepared using General Procedure C employing 117 mg 1-nitropentane, and 510 mg 3-chloroaniline. Purified using silica gel chromatography (0 to 40% EtOAc in hexanes) to afford the desired product as a yellow oil (165 mg, 73%). $^1$H-NMR (600 MHz; CDCl$_3$): δ 7.23 (t, J=8.0 Hz, 1H), 7.10 (dt, J=8.0, 0.9 Hz, 1H), 7.06 (t, J=2.0 Hz, 1H), 6.95-6.93 (m, 1H), 2.34 (t, J=7.7 Hz, 2H), 1.43-1.38 (m, 2H), 1.31-1.26 (m, 2H), 0.83 (t, J=7.3 Hz, 3H). m/z 227.1 (M+H$^+$).

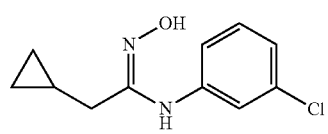 [SMILES: O/N=C(/CC1CC1)Nc1cccc(Cl)c1]

(Z)—N-(3-chlorophenyl)-2-cyclopropyl-N'-hydroxy-acetimidamide

Prepared using General Procedure C employing 115 mg (2-nitroethyl)cyclopropane, and 510 mg 3-chloroaniline. Purified using silica gel chromatography (0 to 35% EtOAc in hexanes) to afford the desired product as an orange oil (156 mg, 69%). $^1$H-NMR (600 MHz; CDCl$_3$): δ 7.23 (t, J=8.0 Hz, 1H), 7.10 (dt, J=8.0, 0.9 Hz, 1H), 7.08 (t, J=2.0 Hz, 1H), 6.97-6.95 (m, 1H), 2.27 (d, J=6.8 Hz, 2H), 0.83-0.76 (m, 1H), 0.47-0.43 (m, 2H), 0.08 (q, J=5.2 Hz, 2H). m/z 225.1 (M+H$^+$).

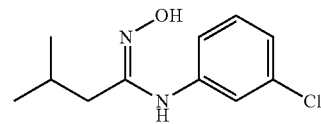

(Z)—N-(3-chlorophenyl)-N'-hydroxy-3-methylbuta-nimidamide

Prepared using General Procedure C employing 117 mg 3-methyl-1-nitrobutane, and 510 mg 3-chloroaniline. Purified using silica gel chromatography (0 to 35% EtOAc in hexanes) to afford the desired product as an orange oil (165 mg, 73%). $^1$H-NMR (600 MHz; CDCl$_3$): δ 7.23 (t, J=8.0 Hz, 1H), 7.11-7.09 (m, 1H), 7.05 (t, J=1.9 Hz, 1H), 6.93 (dt, J=8.0, 1.0 Hz, 1H), 2.23 (d, J=7.3 Hz, 2H), 1.69 (dquintet, J=13.6, 6.8 Hz, 1H), 0.86 (d, J=6.6 Hz, 6H). m/z 227.2 (M+H$^+$).

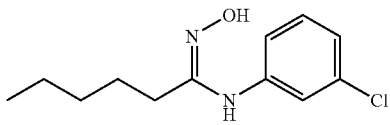 [SMILES: CCCCC/C(=N/O)Nc1cccc(Cl)c1]

(Z)—N-(3-chlorophenyl)-N'-hydroxyhexanimidamide

Prepared using General Procedure C employing 131 mg 1-nitrohexane, and 510 mg 3-chloroaniline. Purified using silica gel chromatography (0 to 25% EtOAc in hexanes) to afford the desired product as an off-white solid (208 mg, 86%). $^1$H-NMR (600 MHz; CDCl$_3$): δ 7.23 (t, J=8.0 Hz, 1H), 7.11-7.09 (m, 1H), 7.05 (t, J=1.9 Hz, 1H), 6.93 (dt, J=8.0, 1.0 Hz, 1H), 2.23 (d, J=7.3 Hz, 2H), 1.69 (dquintet, J=13.6, 6.8 Hz, 1H), 0.86 (d, J=6.6 Hz, 6H). m/z 241.1 (M+H$^+$).

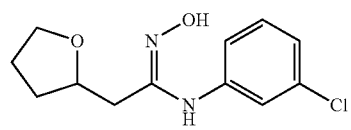 [SMILES: O/N=C(/CC1CCCO1)Nc1cccc(Cl)c1]

(Z)—N-(3-chlorophenyl)-N'-hydroxy-2-(tetrahydrofuran-2-yl)acetimidamide

Prepared using General Procedure C employing 145 mg 2-(2-nitroethyl)tetrahydrofuran, and 510 mg 3-chloroaniline. Purified using silica gel chromatography (15 to 60% EtOAc in hexanes) to afford the desired product as an oil (55 mg, 22%). $^1$H-NMR (600 MHz; CDCl$_3$): δ 7.21 (t, J=7.9 Hz, 1H), 7.09-7.07 (m, 2H), 6.95-6.93 (m, 1H), 4.04-4.00 (m, 1H), 3.81-3.76 (m, 1H), 3.69-3.65 (m, 1H), 2.65 (ddd, J=15.0, 6.7, 3.2 Hz, 1H), 2.43 (ddd, J=15.1, 6.4, 3.1 Hz, 1H), 2.00-1.94 (m, 1H), 1.84-1.80 (m, 2H), 1.54-1.48 (m, 1H). m/z 255.1 (M+H$^+$).

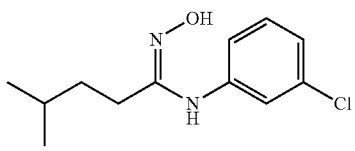 [SMILES: CC(C)CC/C(=N/O)Nc1cccc(Cl)c1]

(Z)—N-(3-chlorophenyl)-N'-hydroxy-4-methylpentanimidamide

Prepared using General Procedure C employing 131 mg 4-methyl-1-nitropentane, and 510 mg 3-chloroaniline. Purified using silica gel chromatography (0 to 35% EtOAc in hexanes) to afford the desired product as an off-white solid (130 mg, 54%). $^1$H-NMR (600 MHz; CDCl$_3$): δ 7.23 (t, J=8.0 Hz, 1H), 7.10 (dd, J=8.0, 0.9 Hz, 1H), 7.07 (s, 1H), 6.94 (dt, J=8.0, 0.8 Hz, 1H), 2.35 (dd, J=9.0, 7.1 Hz, 2H), 1.50 (dquintet, J=13.3, 6.6 Hz, 1H), 1.33-1.29 (m, 2H), 0.80 (d, J=6.6 Hz, 6H). m/z 241.2 (M+H$^+$).

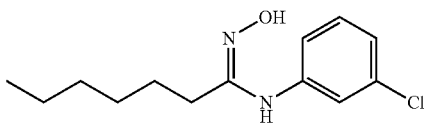 [SMILES: CCCCCC/C(=N/O)Nc1cccc(Cl)c1]

(Z)—N-(3-chlorophenyl)-N'-hydroxyheptanimidamide

Prepared using General Procedure C employing 145 mg 1-nitroheptane, and 510 mg 3-chloroaniline. Purified using silica gel chromatography (0 to 25% EtOAc in hexanes) to afford the desired product as an off-white solid (140 mg, 55%). $^1$H-NMR (400 MHz; CDCl$_3$): δ 7.23 (t, J=8.0 Hz, 1H), 7.10 (ddd, J=8.0, 2.0, 1.0 Hz, 1H), 7.06 (t, J=2.0 Hz, 1H), 6.94 (ddd, J=8.0, 2.1, 1.0 Hz, 1H), 1.29-1.16 (m, 6H), 0.83 (t, J=7.0 Hz, 3H). m/z 255.2 (M+H$^+$).

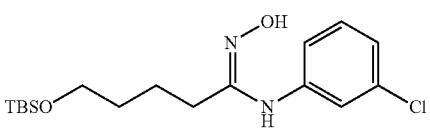 [SMILES: CC(C)(C)[Si](C)(C)OCCCC/C(=N/O)Nc1cccc(Cl)c1]

(Z)-5-((tert-butyldimethylsilyl)oxy)-N-(3-chlorophenyl)-N'-hydroxypentanimidamide Prepared using General Procedure C employing 247 mg tert-butyldimethyl((5-nitropentyl)oxy)silane, and 510 mg 3-chloroaniline. Purified using silica gel chromatography (0 to 4% MeOH in CH$_2$Cl$_2$) to afford the desired product as a red oil. m/z 357.2 (M+H$^+$).

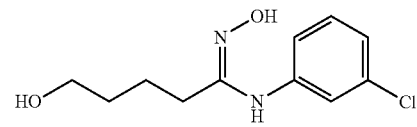 [SMILES: OCCCC/C(=N/O)Nc1cccc(Cl)c1]

(Z)—N-(3-chlorophenyl)-N',5-dihydroxypentanimidamide

To a solution of (Z)-5-((tert-butyldimethylsilyl)oxy)-N-(3-chlorophenyl)-N'-hydroxypentanimidamide (107 mg, 0.3 mmol) was added a solution of tetrabutylammonium fluoride (330 μL, 0.33 mmol, 1M solution in THF). The reaction mixture was stirred at rt for 6 h and was filtered through a 2×2 cm plug of silica eluting with 50 mL EtOAc. The filtrate was concentrated and purified using silica gel chromatography (30 to 100% EtOAc in hexanes) to afford the desired product as an orange solid. m/z 243.2 (M+H$^+$).

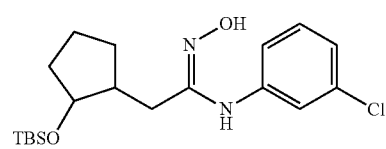 [SMILES: CC(C)(C)[Si](C)(C)OC1CCCC1C/C(=N/O)Nc1cccc(Cl)c1]

(Z)-2-(2-((tert-butyldimethylsilyl)oxy)cyclopentyl)-N-(3-chlorophenyl)-N'-hydroxyacetimidamide Prepared using General Procedure C employing 272 mg tert-butyldimethyl((2-(2-nitroethyl)cyclopentyl)oxy)silane, and 510 mg 3-chloroaniline. Purified using silica gel chromatography (0 to 4% MeOH in CH$_2$Cl$_2$) to afford the desired product as a red oil. m/z 383.2 (M+H$^+$).

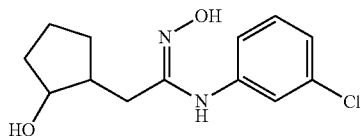 [SMILES: O/N=C(/CC1CCCC1O)Nc1cccc(Cl)c1]

(Z)—N-(3-chlorophenyl)-Y-hydroxy-2-(2-hydroxycyclopentyl)acetimidamide

To a solution of (Z)-2-(2-((tert-butyldimethylsilyl)oxy) cyclopentyl)-N-(3-chlorophenyl)-N-hydroxyacetimidamide (115 mg, 0.3 mmol) was added a solution of tetrabutylammonium fluoride (330 μL, 0.33 mmol, 1M solution in THF). The reaction mixture was stirred at rt for 6 h and was filtered through a 2×2 cm plug of silica eluting with 50 mL EtOAc. The filtrate was concentrated and purified using silica gel chromatography (25 to 60% EtOAc in hexanes) to afford the desired product as an orange solid. m/z 269.2 (M+H$^+$).

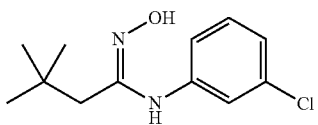 [SMILES: CC(C)(C)C/C(=N/O)Nc1cccc(Cl)c1]

(Z)—N-(3-chlorophenyl)-N'-hydroxy-3,3-dimethylbutanimidamide

Prepared using General Procedure C employing 131 mg 3,3-dimethyl-1-nitrobutane, and 510 mg 3-chloroaniline. Purified using silica gel chromatography (0 to 50% EtOAc in hexanes) to afford the desired product as a yellow semisolid (157 mg, 62%). $^1$H-NMR (400 MHz; CDCl$_3$): δ 7.22 (t, J=8.0 Hz, 1H), 7.10-7.07 (m, 1H), 7.01 (t, J=2.0 Hz, 1H), 6.89 (ddd, J=8.0, 2.0, 0.8 Hz, 1H), 2.33 (s, 2H), 0.86 (s, 9H). m/z 241.2 (M+H$^+$).

General Procedure D: Horner-Wadsworth-Emmons Olefination

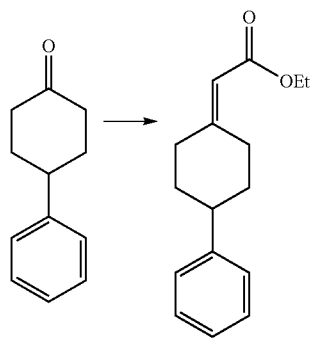 [SMILES: O=C1CCC(c2ccccc2)CC1 ; CCOC(=O)C=C1CCC(c2ccccc2)CC1]

To a suspension of either NaO$^t$Bu or NaH (1.1 equiv) in THF (1.6 M) at 0° C. was added triethylphosphono acetate (1.1 equiv) over 1 h. The mixture was stirred for 1 h at 0° C. and a solution of the appropriate ketone (1.0 equiv) in THF (1.5 M) was added dropwise. The mixture was slowly warmed to rt and was stirred for 90 min before being poured into saturated aqueous NH$_4$Cl and EtOAc. The layers were separated, and aqueous layer was extracted with EtOAc (3×). The combined organics were washed sequentially with saturated NaHCO$_3$ and brine before drying over anhydrous Na$_2$SO$_4$, filtration, and concentration under reduced pressure. The crude material was purified via silica gel chromatography (10% EtOAc in hexanes) to afford the desired product.

General Procedure E: Hydrogenation of α,β-Unsaturated Esters

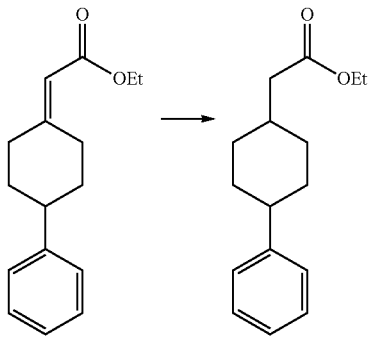 [SMILES: CCOC(=O)C=C1CCC(c2ccccc2)CC1 ; CCOC(=O)CC1CCC(c2ccccc2)CC1]

To a solution of α,β-unsaturated ester (1.0 equiv) in ethanol (0.25 M) was added 10% palladium on carbon (20 weight %). The solution was bubbled with hydrogen gas for 5 min before being capped and stirred under a hydrogen balloon 16 h. After this time, the mixture was filtered through celite and washed thoroughly with EtOAc. The material was then purified through a silica plug and concentrated to give the saturated product in good yield.

General Procedure F: Reduction of α,β-Unsaturated Esters with Stryker's Reagent

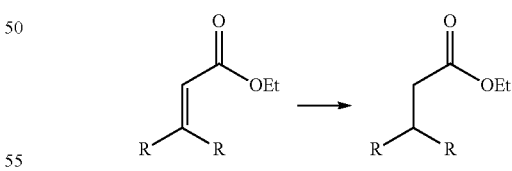

To a solution of α,β-unsaturated ester (1.0 equiv) in toluene (0.5 M) was added [PPh$_3$CuH]$_6$ (1 mol %) and $^t$BuOH (1.1 equiv). The solution was bubbled with argon for 5 min before polymethylhydrosiloxane (590 μL) was added. The resulting mixture was stirred under argon at rt for 14 h at which point saturated aqueous NaHCO$_3$ and diethyl ether were added. The heterogeneous mixture was stirred for 3 h, and the layers were separated. The aqueous layer was extracted with diethyl ether (2×) and the combined organic extracts were dried over anhydrous Na$_2$SO$_4$, concentrated under reduced pressure, and the resulting mixture was purified employing silica gel chromatography (0 to 100% EtOAc in hexanes) to afford the desired product.

General Procedure G: Ester Hydrolysis

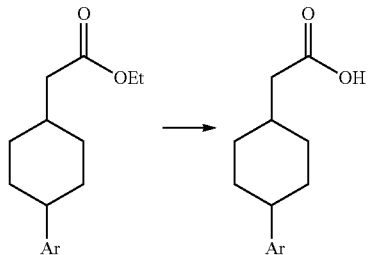

To a solution of ester (1.0 equiv.) in EtOH (1.0 M) was added an equal volume of aqueous LiOH solution (7.25 M). The mixture was stirred vigorously, heated to 50° C. for 1 h and then diluted with 50 mL of water and further heated to 50° C. for 5 h. The mixture was cooled with an ice bath and acidified (pH ~1) by slow addition of 3 M HCl. EtOAc was added, the layers were separated, and the aqueous phase was extracted with EtOAc (3×). The combined organic extracts were dried over anhydrous $Na_2SO_4$ and concentrated under reduced pressure to afford the desired carboxylic acid which was used without further purification.

General Procedure H: Amide Formation Via Acyl Chloride

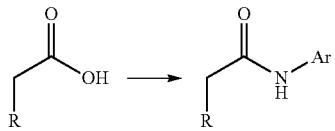

The appropriate carboxylic acid (1.0 equiv) was dissolved in dichloromethane (0.5 M) and cooled to 0° C. Oxalyl chloride (1.2 equiv) was added carefully, followed by 1 drop of DMF. The mixture was then warmed to rt over 15 minutes before being cooled back to 0° C. Meanwhile, the appropriate aniline (2.0 equiv) and triethylamine (2.0 equiv) were combined in dichloromethane (1 M with respect to aniline). This solution was added dropwise to the cold solution of acyl chloride. The mixture was then stirred at rt for 2 h before being carefully quenched with 1 N HCl. The organic layer was separated and the aqueous layer extracted once more with dichloromethane. The combined organic layers were washed with brine, dried over sodium sulfate, filtered, and concentrated under reduced pressure. The crude residue was purified by silica gel chromatography (0 to 100% EtOAc in hexanes) to afford the desired product.

General Procedure I: Amide Bond Coupling with HATU

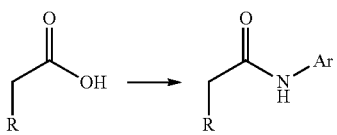

To a stirred solution of carboxylic acid (1.0 equiv) in DMF (0.3 M) was added aniline (1.5 equiv), $^iPr_2NEt$ (2 equiv), and 1-[bis(dimethylamino)methylene]-1H-1,2,3-triazolo[4,5-b]pyridinium 3-oxid hexafluorophosphate (HATU) (1.2 equiv). The resulting mixture was stirred at rt for 3 h at which point 3 M HCl and $CH_2Cl_2$ were added. The layers were separated and the aqueous layer was extracted with $CH_2Cl_2$ (2×). The combined organic extracts were dried over anhydrous $Na_2SO_4$, concentrated under reduced pressure and the resulting residue was purified by silica gel chromatography (0 to 100% EtOAc in hexanes) to afford the desired product.

General Procedure J: Aniline Addition to Esters

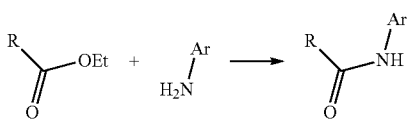

To a solution of the aniline (2.0 equiv) in THF (0.25 M) at 0° C. was added a solution of $^iPrMgCl$ (2.0 equiv, 2 M in THF). The resulting solution was warmed to rt, stirred for 5 min at which point the ester (1.0 equiv) was added dropwise. The resulting mixture was stirred at rt for 8 h and was poured onto a saturated solution of $NH_4Cl$. EtOAc was added the layers were separated. The aqueous layer was extracted with EtOAc (3×). The combined organic extracts were dried over anhydrous $MgSO_4$, filtered, and concentrated under reduced pressure. The crude mixture was purified employing silica gel chromatography (0 to 100% EtOAc in hexanes) to afford the desired product.

General Procedure K: Thioamide Formation

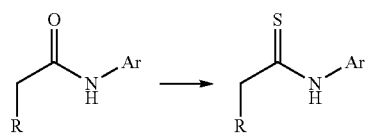

A slurry of the amide (0.1 mmol, 1.0 equiv.) and Lawesson's reagent (0.055 mmol, 0.55 equiv.) were heated in PhMe (400 µL) for 2 h. The resulting yellow solution was concentrated and purified employing silica gel flash chromatography (0 to 25% EtOAc in hexanes). To deliver the desired product as a yellow oil.

General Procedure L: Thioimino Ether Formation

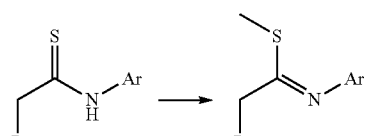

To a solution of the thioamide (0.1 mmol, 1.0 equiv.) in $CH_2Cl_2$ (500 µL) was added $NaHCO_3$ (168 mg, 2.0 mmol, 20 equiv.). The resulting slurry was cooled to 0° C. and Me₃OBF₄ (74 mg, 0.5 mmol, 5.0 equiv.) was added. The mixture was allowed to warm to rt, and was stirred for 1 h. The mixture was cooled to 0° C. and a saturated NaHCO₃ solution (2 mL) was added. The biphasic mixture was stirred for 5 min, diluted with EtOAc (10 mL), and the layers were separated. The aqueous layer was extracted with EtOAc (3×10 mL). The combined organic extracts were dried over anhydrous MgSO₄, filtered, and concentrated. The crude mixture was used directly in the subsequent step.

General Procedure M: Hydroxyamidine Formation from Thioimino Ethers

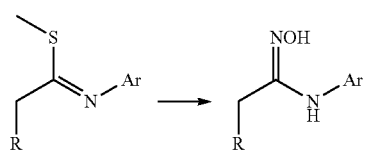

To a solution of the crude thioimino ether from the previous step in EtOH (1.0 mL) was added hydroxylamine solution (50 wt. % in H₂O, 120 µL), and the resulting mixture was heated to 60° C. for 16 h. LC/MS analysis indicated complete consumption of the starting material and formation of the desired product. The mixture was diluted with water (10 mL) and EtOAc (10 mL) and the layers were separated. The aqueous layer was extracted with EtOAc (3×10 mL). The combined organic extracts were dried over anhydrous MgSO₄, filtered, and concentrated under reduced pressure. The crude mixture was purified employing silica gel flash chromatography (0 to 5% MeOH in CH₂Cl₂) to provide the desired product as a yellow oil.

General Procedure N: Hydroxyamidine Formation from Nitro Compounds

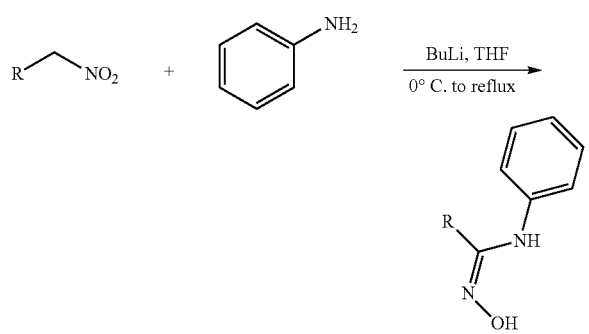

To a solution of substituted aniline (1.2 mmol) in THF (1.0 mL) at −78° C. was added a solution of n-BuLi (480 µL, 1.2 mmol, 2.5M in hexanes). The resulting mixture became heterogeneous and was allowed to warm to rt over 30 min. The mixture was cooled to 0° C. and the appropriate nitroalkane (0.3 mmol) was added dropwise. The resulting suspension was heated to 65° C. for 2 h at which point TLC analysis indicated complete consumption of the nitroalkane. The mixture was cooled to 0° C. and was diluted with saturated NH₄Cl solution (10 mL), EtOAc (10 mL) and stirred for 5 min. The layers were separated, and the aqueous layer was extracted with EtOAc (3×15 mL). The combined organic layers were dried over anhydrous MgSO₄, filtered, and concentrated under reduced pressure. The crude mixture was purified employing silica gel chromatography to afford the desired product.

General Procedure O: Preparation of Aryl Cyclohexenes Via Suzuki Cross-Coupling Reaction

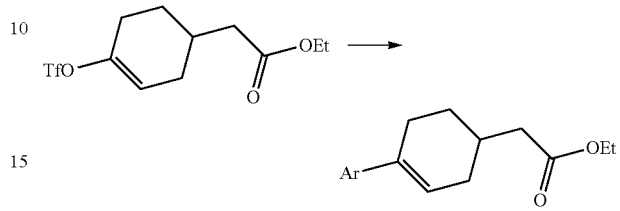

To ethyl 2-(4-(((trifluoromethyl)sulfonyl)oxy)cyclohex-3-en-1-yl)acetate (1.0 equiv), boronic acid (1.2 equiv), K₃PO₄ (1.5 equiv), KBr (1.1 equiv) in 1,4-dioxane (0.25M) was added water (0.025M) followed by Pd(PPh₃)₄ (5-10 mol %). The resulting mixture was heated to 80° C. for 16 h, upon which the crude mixture was concentrated under reduced pressure. The resulting solids were diluted with EtOAc and water and the layers were separated. The aqueous layer was extracted with EtOAc (3×). The combined organic extracts were dried over anhydrous MgSO₄, filtered, and concentrated under reduced pressure. The crude mixture was purified employing silica gel chromatography (0 to 100% EtOAc in hexanes) to afford the desired product.

General Procedure P: Hydrogenation

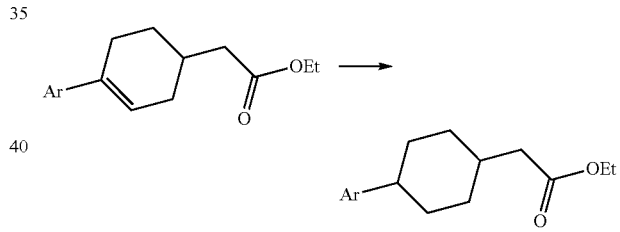

A solution of the unsaturated starting material in the indicated solvent was purged with nitrogen gas and 20 wt. % of the indicated catalyst (dry activated Pd/C 10 wt. %, or Degussa Pd/C 10 wt. %, or 10 wt. % Pd(OH)₂/C) was added. The flask was closed with a rubber septum and hydrogen gas was bubbled through the heterogeneous mixture until complete disappearance of the starting material (determined by TLC, and/or LC-MS, and/or NMR). Upon completion, mixture was purged with nitrogen gas, filtered through a pad of celite, and concentrated under reduced pressure. The crude mixture was purified employing silica gel chromatography (0 to 100% EtOAc in hexanes) to afford the desired product.

General Procedure Q: Preparation of Aryl Cyclohexenes Via Suzuki Cross-Coupling Reaction

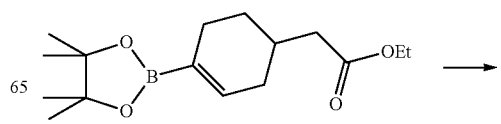

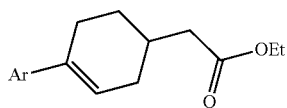

To ethyl 2-(4-(4,4,5,5-tetramethyl-1,3,2-dioxaborolan-2-yl)cyclohex-3-en-1-yl)acetate (1.0 equiv), aryl halide (1.0 equiv), Na₂CO₃ (3.0 equiv), and Pd(PPh₃)₄ (5-10 mol %), were added 1,4-dioxane/water (9:1, 0.2M). The resulting mixture was degassed with nitrogen gas and heated to 85° C. for 24 h upon which the crude mixture was concentrated under reduced pressure. The resulting solids were diluted with EtOAc and water and the layers were separated. The aqueous layer was extracted with EtOAc (3×). The combined organic layers were dried over anhydrous MgSO₄, filtered, and concentrated under reduced pressure. The crude mixture was purified employing silica gel chromatography (0 to 100% EtOAc in hexanes) to afford the desired product.

General Procedure R: Preparation of Hydroxyamidines

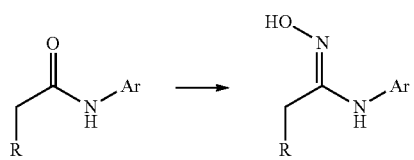

To a solution of the amide in CH₂Cl₂ (0.1 M) at −78° C. was added Tf₂O (1.5 equivalents) and pyridine (2 equivalents). The mixture was warmed rt and stirred at rt for 15 min. Then, NH₂OH (20 equivalents, 50 wt. % in H₂O) was added and the mixture was stirred for 1 h. The mixture was concentrated under reduced pressure and purified by silica gel column chromatography to afford the desired product.

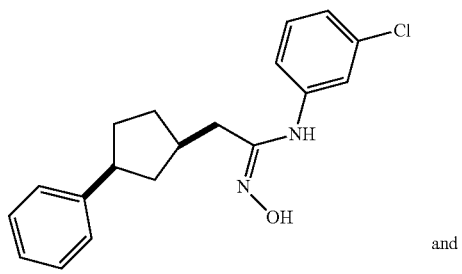

and

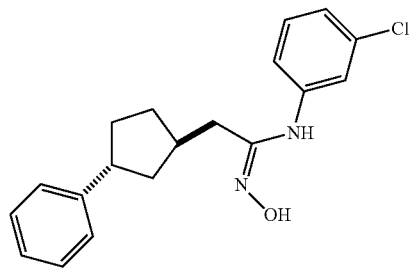

(cis)-N-(3-Chlorophenyl)-N'-hydroxy-2-(3-phenyl-cyclopentyl)acetimidamide and (trans)-N-(3-chlorophenyl)-N'-hydroxy-2-(3-phenylcyclopentyl)acetimidamide Prepared in the same manner as N-(3-chlorophenyl)-N-hydroxy-2-((1,3)-3-phenylcyclohexyl)acetimidamide replacing cyclohexenone with cyclopentenone. The mixture of diastereomers was isolated as a white solid. ¹H NMR (400 MHz, CDCl₃): δ 9.20-8.40 (bs, 1H), 7.30-6.96 (m, 9H), 3.15-2.87 (m, 1H), 2.64-2.39 (m, 2H), 2.35-1.18 (m, 7H) ppm.

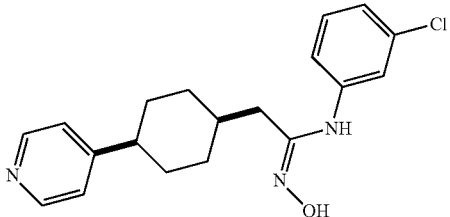

and

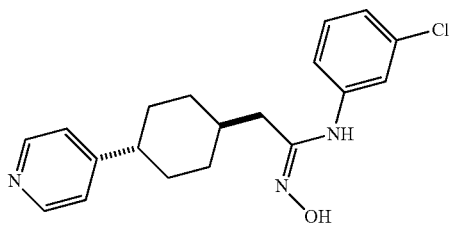

(cis)-N-(3-Chlorophenyl)-N'-hydroxy-2-(4-(pyridin-4-yl)cyclohexyl)acetimidamide and (trans)-N-(3-chlorophenyl)-N'-hydroxy-2-(4-(pyridin-4-yl)cyclohexyl)acetimidamide Prepared using General Procedures Q, P, G, H, K, L, M. In General Procedure Q, 4-bromopyridine hydrochloride was used. In General Procedure P, AcOH and Degussa Pd/C were used. In General Procedure H, 3-chloroaniline was used. In General Procedure L, NaHCO₃ was replaced with K₂CO₃. The desired products were obtained as a mixture of diastereomers as an off-white solid. ¹H NMR (400 MHz, CD₃OD): δ 8.40-8.33 (m, 2H), 7.33-7.23 (m, 3H), 7.17-7.08 (m, 2H), 7.14-7.04 (m, 1H), 2.56-2.42 (m, 2H), 2.32 (d, J=7.2 Hz, 1H), 1.81 (t, J=13.0 Hz, 3H), 1.63-1.16 (m, 5H), 1.15-0.98 (m, 1H) ppm. m/z 172.7 (M+2H)²⁺.

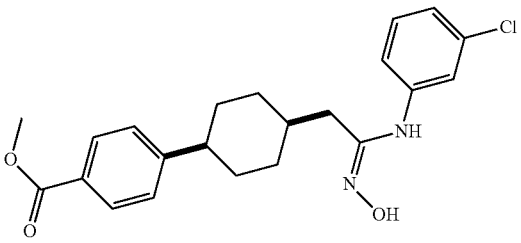

63

(cis)-Methyl 4-(4-(2-((3-chlorophenyl)amino)-2-(hydroxyimino)ethyl)cyclohexyl)-benzoate

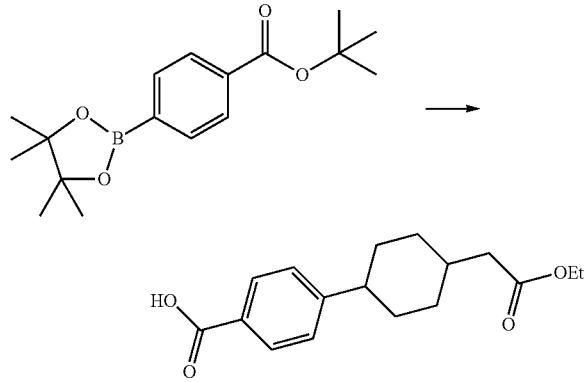

General Procedures O, P, and J were used to give 4-(4-(2-ethoxy-2-oxoethyl)cyclohexyl)benzoic acid. In General Procedure O, tert-Butyl 4-(4,4,5,5-tetramethyl-1,3,2-dioxaborolan-2-yl)benzoate was used. In General Procedure P, AcOH and Degussa Pd/C were used.

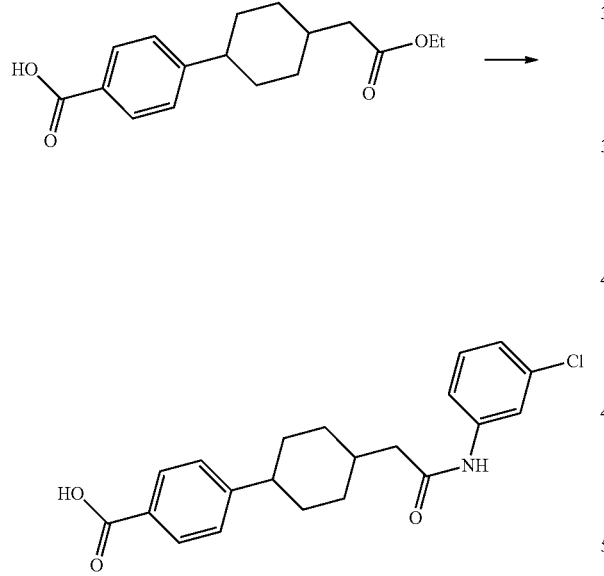

4-(4-(2-((3-Chlorophenyl)amino)-2-oxoethyl)cyclohexyl)benzoic acid was obtained using General Procedure J, which employed 3-chloroaniline.

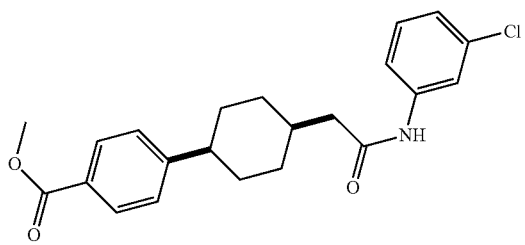

A solution of 4-(4-(2-((3-Chlorophenyl)amino)-2-oxoethyl)cyclohexyl)benzoic acid in MeOH was added. The mixture was heated at reflux for 8 h. The mixture was cooled to rt and concentrated under reduced pressure to give (cis)-methyl 4-(4-(2-((3-chlorophenyl)amino)-2-oxoethyl)cyclohexyl)benzoate.

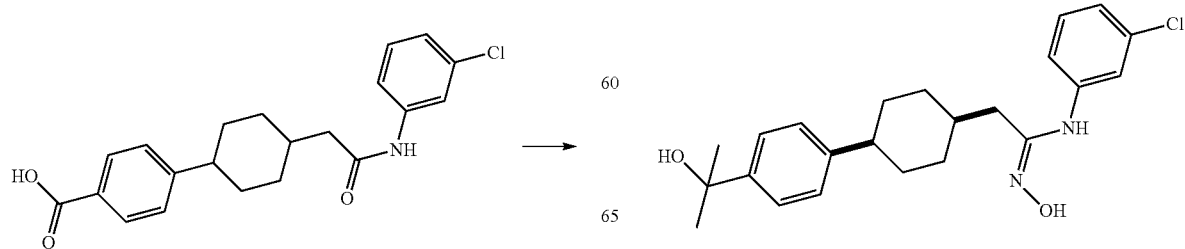

Prepared from (cis)-methyl 4-(4-(2-((3-chlorophenyl)amino)-2-oxoethyl)cyclohexyl)benzoate using General Procedures K, L, and M. In General Procedure L, replacing NaHCO$_3$ with K$_2$CO$_3$ to give the desired product as an off-white solid. $^1$H NMR (400 MHz, CDCl$_3$): δ 7.93 (d, J=8.3 Hz, 2H), 7.22 (d, J=8.5 Hz, 2H), 7.15-6.93 (m, 4H), 3.89 (s, 3H), 2.49 (d, J=7.4 Hz, 2H), 1.88-1.80 (m, 1H) 1.67-1.41 (m, 9H) ppm. m/z 401.2 (M+H)$^+$.

(cis)-N-(3-Chlorophenyl)-N'-hydroxy-2-(4-(4-(2-hydroxypropan-2-yl)phenyl)cyclohexyl)acetimidamide

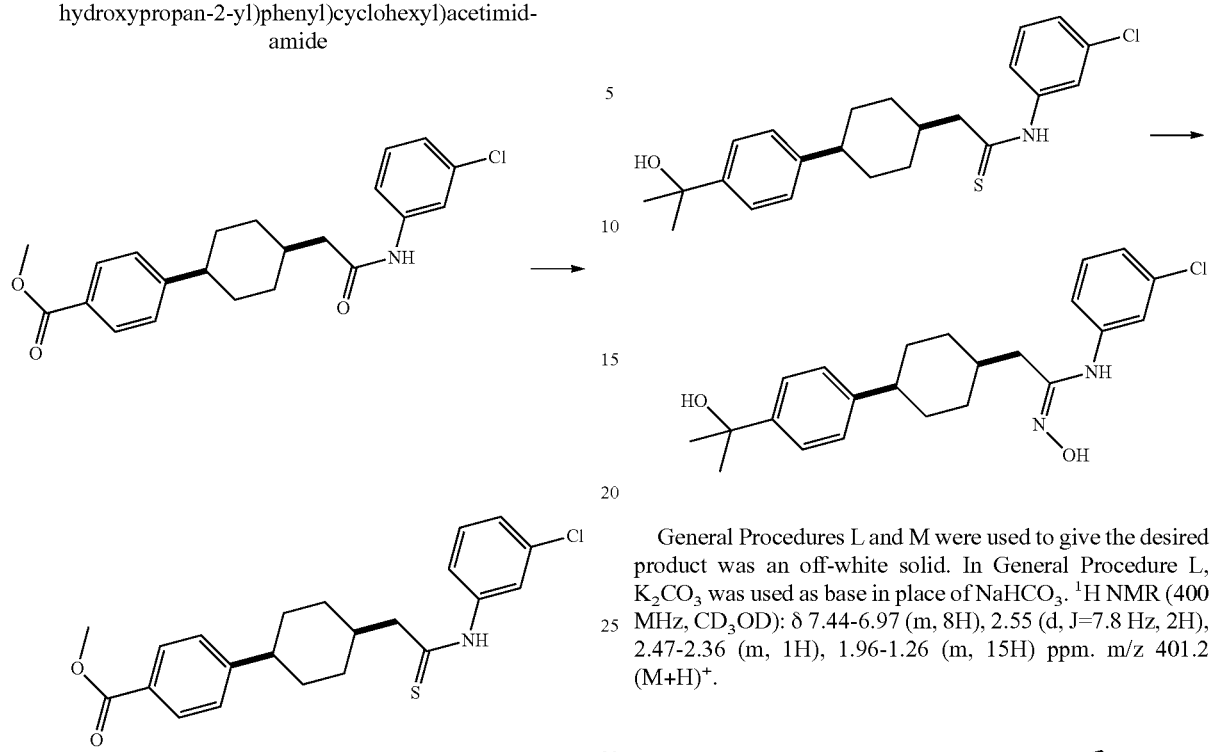

General Procedures K was used to give (cis)-methyl 4-(4-(2-((3-chlorophenyl)amino)-2-thioxoethyl)cyclohexyl)benzoate.

(Cis)-methyl 4-(4-(2-((3-chlorophenyl)amino)-2-thioxoethyl)cyclohexyl)benzoate was treated with MeMgCl (3.5 equivalents) in diethyl ether at 0° C. to rt for 30 minutes Sat. NH$_4$Cl was added and the mixture was extracted with EtOAc. The organic layer was dried over Na$_2$SO$_4$ and concentrated under reduced pressure to give (cis)-N-(3-chlorophenyl)-2-(4-(4-(2-hydroxypropan-2-yl)phenyl)cyclohexyl)ethanethioamide.

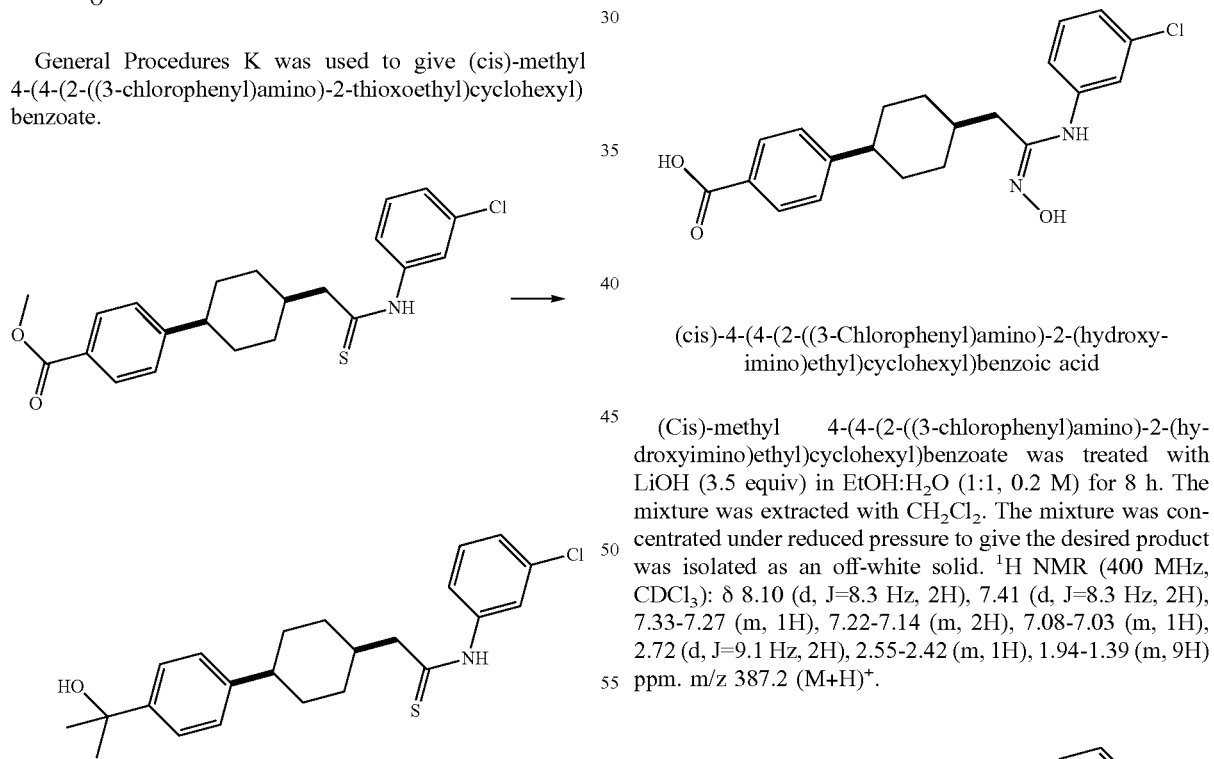

General Procedures L and M were used to give the desired product was an off-white solid. In General Procedure L, K$_2$CO$_3$ was used as base in place of NaHCO$_3$. $^1$H NMR (400 MHz, CD$_3$OD): δ 7.44-6.97 (m, 8H), 2.55 (d, J=7.8 Hz, 2H), 2.47-2.36 (m, 1H), 1.96-1.26 (m, 15H) ppm. m/z 401.2 (M+H)$^+$.

(cis)-4-(4-(2-((3-Chlorophenyl)amino)-2-(hydroxyimino)ethyl)cyclohexyl)benzoic acid (Cis)-methyl 4-(4-(2-((3-chlorophenyl)amino)-2-(hydroxyimino)ethyl)cyclohexyl)benzoate was treated with LiOH (3.5 equiv) in EtOH:H$_2$O (1:1, 0.2 M) for 8 h. The mixture was extracted with CH$_2$Cl$_2$. The mixture was concentrated under reduced pressure to give the desired product was isolated as an off-white solid. $^1$H NMR (400 MHz, CDCl$_3$): δ 8.10 (d, J=8.3 Hz, 2H), 7.41 (d, J=8.3 Hz, 2H), 7.33-7.27 (m, 1H), 7.22-7.14 (m, 2H), 7.08-7.03 (m, 1H), 2.72 (d, J=9.1 Hz, 2H), 2.55-2.42 (m, 1H), 1.94-1.39 (m, 9H) ppm. m/z 387.2 (M+H)$^+$.

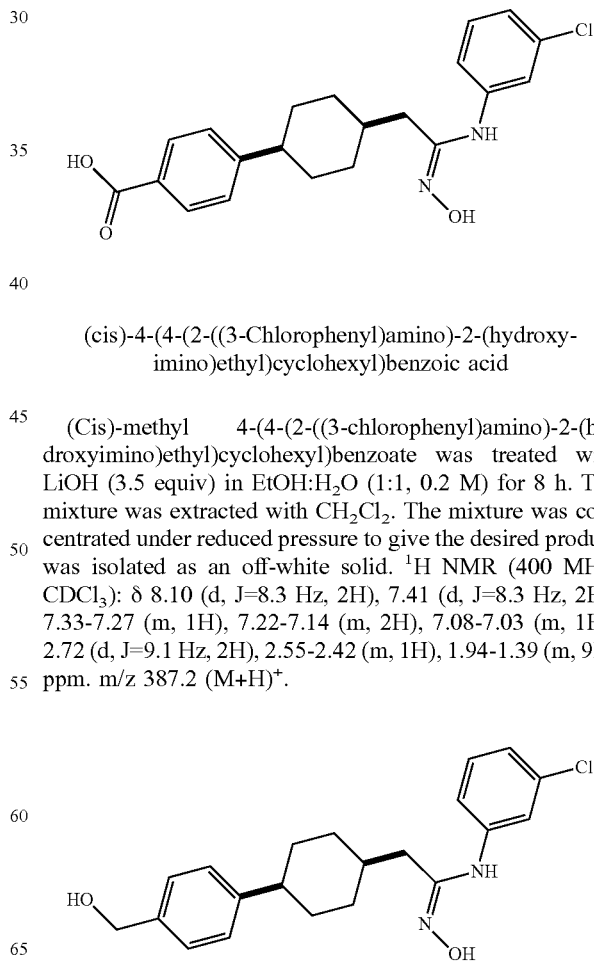

67

(cis)-N-(3-Chlorophenyl)-N'-hydroxy-2-(4-(4-(hydroxymethyl)phenyl)cyclohexyl)-acetimidamide

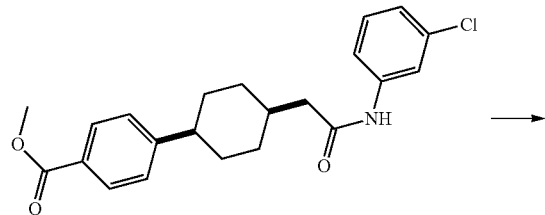

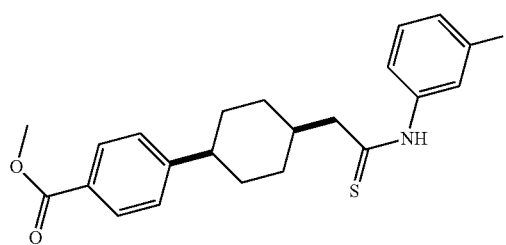

Prepared using General Procedures K to give (cis)-methyl 4-(4-(2-((3-chlorophenyl)amino)-2-thioxoethyl)cyclohexyl)benzoate

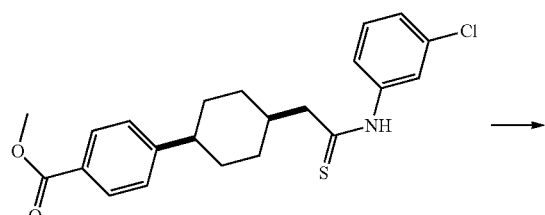

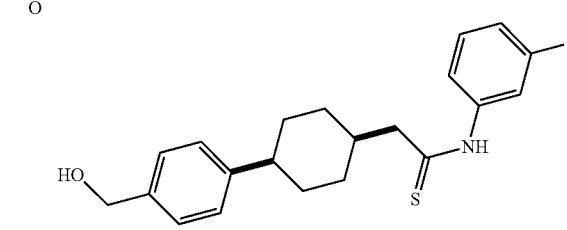

(Cis)-methyl 4-(4-(2-((3-chlorophenyl)amino)-2-thioxoethyl)cyclohexyl)benzoate was treated with LiAlH$_4$ (2.0 equivalents) in THF (0.1 M) at 0° C. for 10 min. The mixture was quenched with 1 M HCl, extracted with EtOAc and purified by silica gel column chromatography (0-100% EtOAc in Hexanes) to obtain N-(cis)-(3-chlorophenyl)-2-(4-(4-(hydroxymethyl)phenyl)cyclohexyl)ethanethioamide.

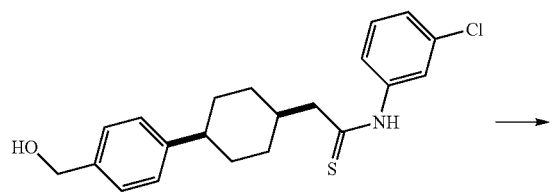

68

-continued

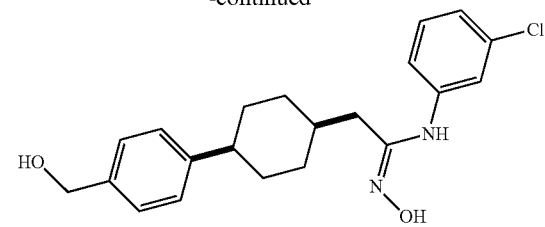

Prepared using General Procedures L and M. In General Procedure L, NaHCO$_3$ was replaced with K$_2$CO$_3$. The desired product was obtained as an off-white solid. $^1$H NMR (400 MHz, CDCl$_3$): δ 7.30-7.26 (m, 2H), 7.20-6.93 (m, 6H), 4.65 (s, 1H), 2.49 (d, J=7.7 Hz, 2H), 1.92-1.74 (m, 1H), 1.65-1.45 (m, 9H) ppm. m/z 373.2 (M+H)$^+$.

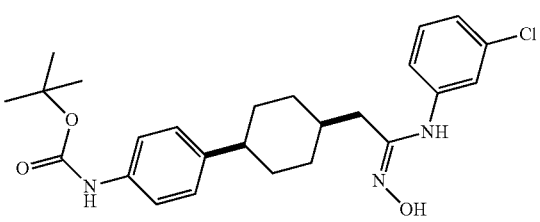

(cis)-tert-butyl (4-(4-(2-((3-Chlorophenyl)amino)-2-(hydroxyimino)ethyl)-cyclohexyl)phenyl)carbamate Prepared by General Procedures O, P, G, I, K, L, and M. In General Procedure O, 4-(Boc-amino)phenylboronic acid was used as the coupling partner. In General Procedure P, Degussa Pd/C and AcOH were used as the catalyst and solvent respectively. In General Procedure I, 3-chloroaniline was used. In General Procedure L, K$_2$CO$_3$ was used in place of NaHCO$_3$. The desired product was obtained as an off-white solid. $^1$H NMR (400 MHz, CDCl$_3$): δ 7.25-7.21 (m, 3H), 7.15-7.02 (m, 5H), 6.96 (d, J=9.2 Hz, 1H), 2.50-2.40 (m, 3H), 1.83 (s, 1H), 1.65-1.39 (m, 19H) ppm.

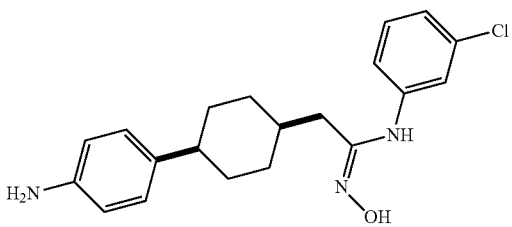

(cis)-2-(4-(4-Aminophenyl)cyclohexyl)-N-(3-chlorophenyl)-N'-hydroxyacetimidamide Prepared from (cis)-tert-butyl (4-(4-(2-((3-chlorophenyl)amino)-2-(hydroxyimino)ethyl)cyclohexyl)phenyl)carbamate by treatment with trifluoroacetic acid and CH$_2$Cl$_2$ (1:1, 0.1 M) for 30 min at rt, quenching with 1 M NaOH, extracting with CH$_2$Cl$_2$ and purified by silica gel chromatography (0-100% EtOAc in hexanes). The desired product was isolated as an off-white solid. m/z 358.3 (M+H)$^+$.

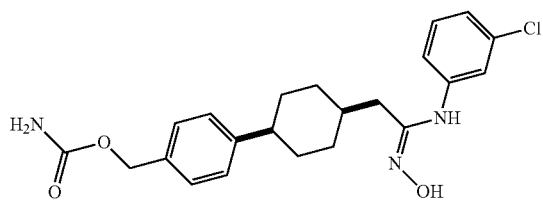

(cis)-4-(4-(2-(((3-Chlorophenyl)amino)-2-(hydroxy-imino)ethyl)cyclohexyl)benzyl carbamate

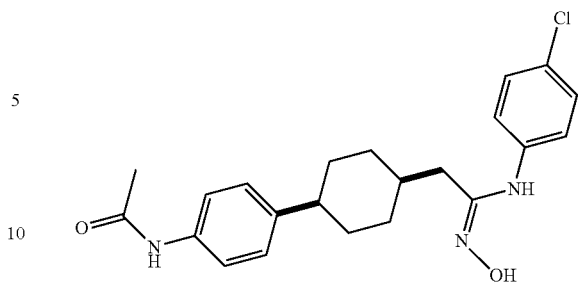

(cis)-N-(4-(4-((Z)-2-((3-Chlorophenyl)amino)-2-(hydroxyimino)ethyl)-cyclohexyl)phenyl)acetamide

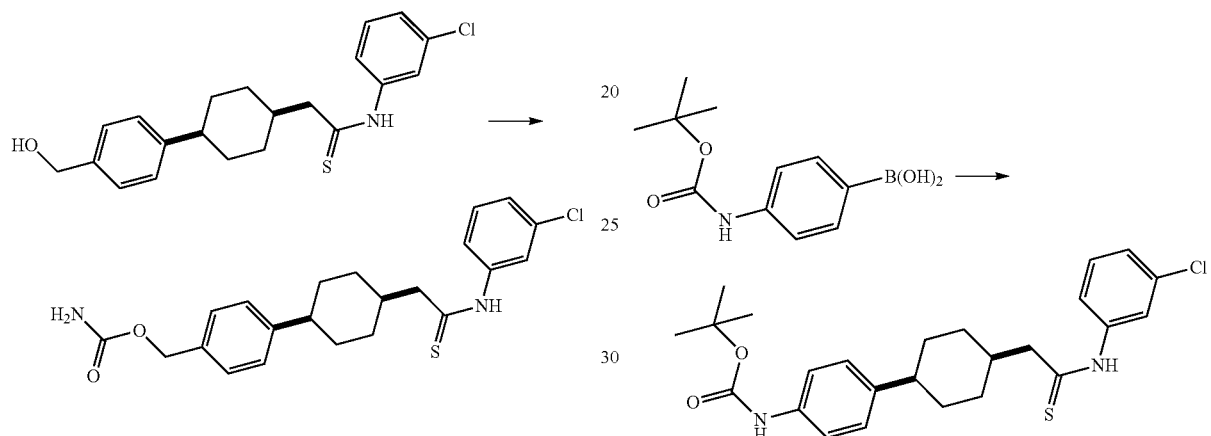

N-(cis)-(3-chlorophenyl)-2-(4-(4-(hydroxymethyl)phenyl)cyclohexyl)ethanethioamide was dissolved in CH$_2$Cl$_2$ and trichloroacetylisocyanate (1.1 equivalent) was added at rt. After stirring for 1 h, MeOH and K$_2$CO$_3$ were added and the mixture was stirred for 4 h. The mixture was concentrated under reduce pressure and the residue was purified by silica gel column chromatography (0-100% EtOAc in hexanes) to yield (cis)-4-(4-(2-((3-chlorophenyl)amino)-2-thioxoethyl)cyclohexyl)benzyl carbamate.

General Procedures O, P, G, I, K were employed. In General Procedure O, 4-(Boc-amino)phenylboronic acid was used as the coupling partner. In General Procedure P, Degussa Pd/C and AcOH were used as the catalyst and solvent respectively. In General Procedure I, 3-chloroaniline was used. In General Procedure L, K$_2$CO$_3$ was used in place of NaHCO$_3$ to afford (cis)-tert-butyl (4-(4-(2-((3-chlorophenyl)amino)-2-thioxoethyl)cyclohexyl)phenyl)carbamate.

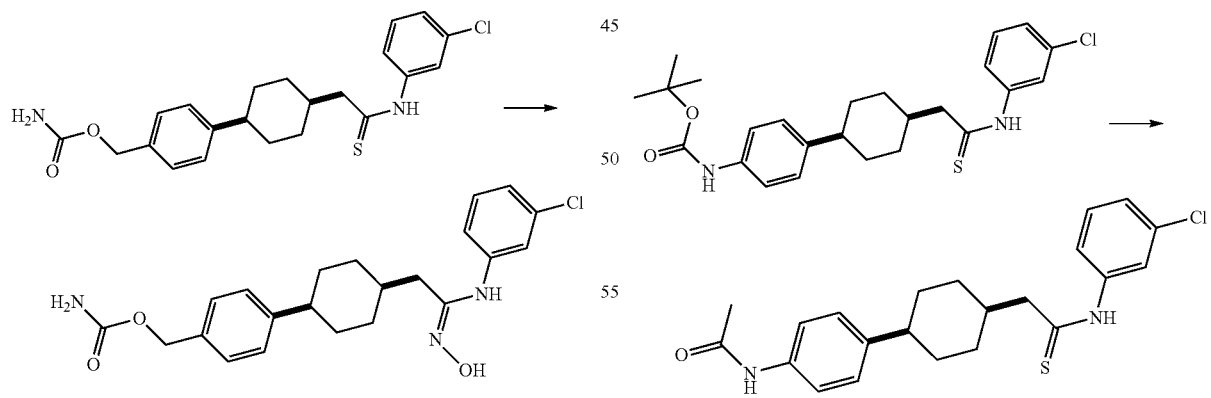

General Procedures L, and M were used to give the desired product as an off-white solid. In General Procedure L, K$_2$CO$_3$ was used in place of NaHCO$_3$. $^1$H NMR (400 MHz, CDCl$_3$) δ 7.28-7.22 (m, 2H), 7.18-7.10 (m, 4H), 7.07 (t, J=2.0 Hz, 1H), 6.94 (ddd, J=8.0, 2.1, 1.0 Hz, 1H), 5.04 (s, 2H), 4.78 (s, 2H), 2.55-2.35 (m, 3H), 1.92-1.76 (m, 2H), 1.67-1.47 (m, 7H) ppm. m/z 416.2 (M+H)$^+$.

(Cis)-tert-butyl (4-(4-(2-((3-chlorophenyl)amino)-2-thioxoethyl)cyclohexyl)-phenyl)carbamate was dissolving in trifluoroacetic acid and CH$_2$Cl$_2$ (1:1, 0.1 M) and the mixture was stirred at rt for 30 min. The mixture was basified with saturated aqueous NaHCO$_3$, extracted with CH$_2$Cl$_2$. The organic layer was concentrated under reduced pressure. The residue was diluted with pyridine (0.1 M) and acetic anhydride (1.2 equivalents) was added. The mixture was stirred at rt for 1.5 h, poured onto saturated aqueous NH₄Cl and extracted with CH₂Cl₂. The organic layer was dried over Na₂SO₄ and concentrated under reduced pressure to give (cis)-N-(4-(4-(2-((3-chlorophenyl)amino)-2-thioxoethyl)cyclohexyl)phenyl)acetamide.

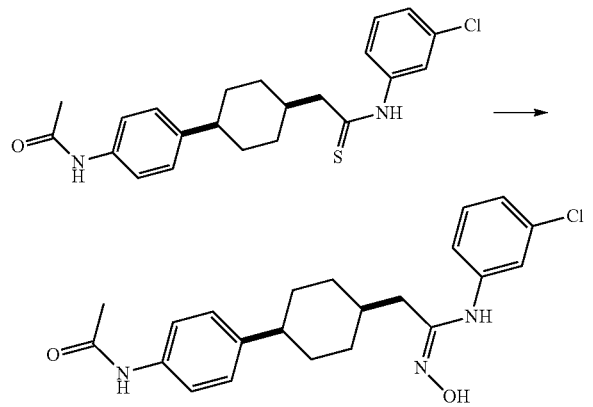

General Procedures L, and M were utilized. In General Procedure L, K₂CO₃ was utilized in place of NaHCO₃. ¹H NMR (400 MHz, CD₃OD): δ 7.40 (d, J=8.5 Hz, 2H), 7.29 (t, J=8.0 Hz, 1H), 7.16-7.01 (m, 5H), 2.53 (d, J=7.8 Hz, 2H), 2.46-2.37 (m, 1H), 2.09 (s, 3H), 1.95-1.43 (m, 9H) ppm. m/z 400.3 (M+H)⁺.

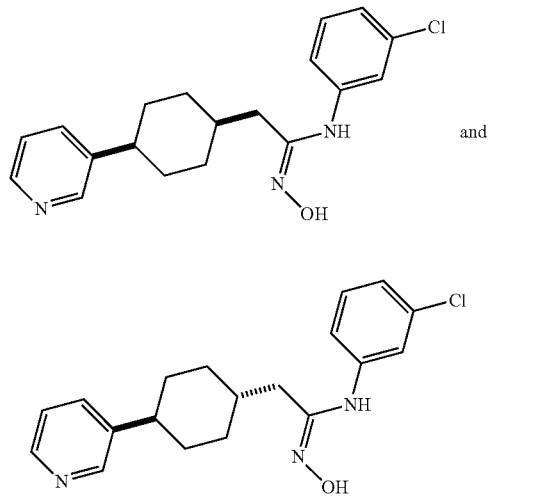

(cis)-N-(3-Chlorophenyl)-N'-hydroxy-2-(4-(pyridin-3-yl)cyclohexyl)acetimidamide and (trans)-N-(3-chlorophenyl)-N'-hydroxy-2-(4-(pyridin-3-yl)cyclohexyl)acetimidamide Prepared by General Procedures Q, P, J, and R. Purified by silica gel column chromatography (0-20% MeOH in CH₂Cl₂) to give a mixture of diastereomers. ¹H NMR (400 MHz, CD₃OD): δ 8.46-8.27 (m, 2H), 7.80-7.61 (m, 1H), 7.40-7.22 (m, 2H), 7.17-7.01 (m, 3H), 2.70-2.27 (m, 3H), 2.02-0.83 (m, 9H) ppm. m/z 172.7 (M+2H)²⁺.

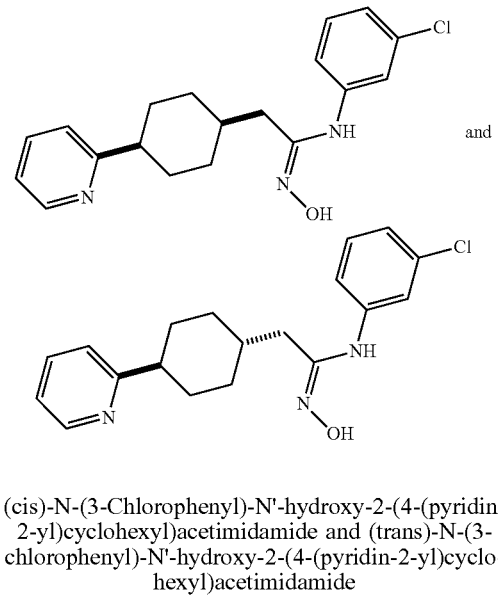

(cis)-N-(3-Chlorophenyl)-N'-hydroxy-2-(4-(pyridin-2-yl)cyclohexyl)acetimidamide and (trans)-N-(3-chlorophenyl)-N'-hydroxy-2-(4-(pyridin-2-yl)cyclohexyl)acetimidamide Prepared by General Procedures Q, P, J, and R. Purified by silica gel column chromatography 0-20% MeOH in CH₂Cl₂) to give a mixture of diastereomers. ¹H NMR (400 MHz, CD₃OD): δ 8.47-8.33 (m, 1H), 7.80-7.68 (m, 1H), 7.40-7.00 (m, 6H), 2.82-2.24 (m, 3H), 2.05-1.00 (m, 9H) ppm. LC/MS, m/z 172.7 (M+2H)²⁺.

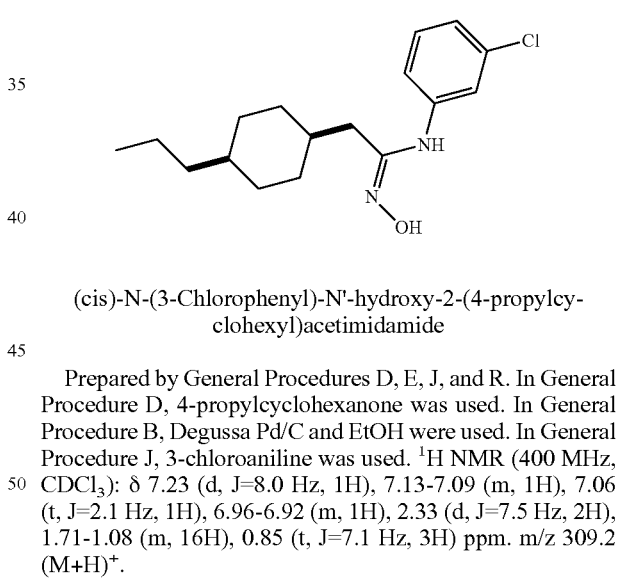

(cis)-N-(3-Chlorophenyl)-N'-hydroxy-2-(4-propylcyclohexyl)acetimidamide

Prepared by General Procedures D, E, J, and R. In General Procedure D, 4-propylcyclohexanone was used. In General Procedure B, Degussa Pd/C and EtOH were used. In General Procedure J, 3-chloroaniline was used. ¹H NMR (400 MHz, CDCl₃): δ 7.23 (d, J=8.0 Hz, 1H), 7.13-7.09 (m, 1H), 7.06 (t, J=2.1 Hz, 1H), 6.96-6.92 (m, 1H), 2.33 (d, J=7.5 Hz, 2H), 1.71-1.08 (m, 16H), 0.85 (t, J=7.1 Hz, 3H) ppm. m/z 309.2 (M+H)⁺.

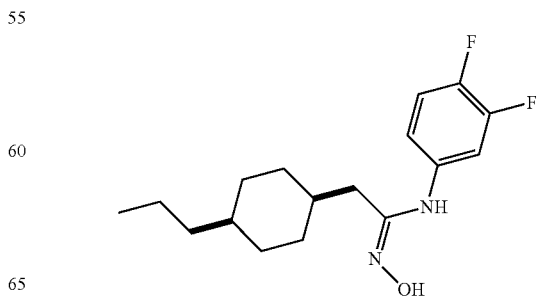

(cis)-N-(3,4-Difluorophenyl)-N'-hydroxy-2-(4-propylcyclohexy)acetimidamide

Prepared by General Procedures D, E, J, and R. $^1$H NMR (400 MHz, CDCl$_3$): δ 7.17-7.06 (m, 1H), 6.91 (ddd, J=11.5, 7.0, 2.7 Hz, 1H), 6.83-6.77 (m, 1H), 2.25 (d, J=7.4 Hz, 2H), 1.45-1.11 (m, 14H), 0.85 (t, J=7.1 Hz, 3H) ppm. m/z 311.3 (M+H)$^+$.

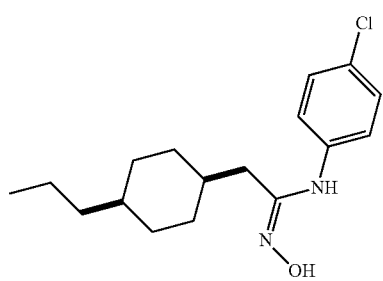 [SMILES: CCC[C@H]1CC[C@@H](C/C(=N/O)Nc2ccc(Cl)cc2)CC1]

(cis)-N-(4-Chlorophenyl)-N'-hydroxy-2-(4-propylcyclohexyl)acetimidamide

Prepared by General Procedures D, E, J and R. $^1$H NMR (400 MHz, CDCl$_3$): δ 7.30-7.26 (m, 2H), 7.02-6.97 (m, 2H), 2.28 (d, J=7.5 Hz, 2H), 1.63-1.11 (m, 14H), 0.85 (t, J=7.1 Hz, 3H) ppm. m/z 309.2 (M+H)$^+$.

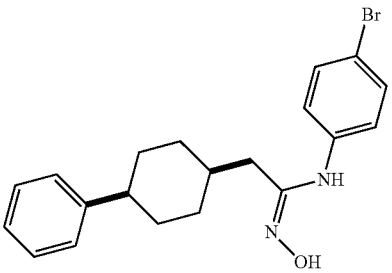 [SMILES: O/N=C(/C[C@H]1CC[C@@H](c2ccccc2)CC1)Nc1ccc(Br)cc1]

(cis)-N-(4-Bromophenyl)-N'-hydroxy-2-(4-phenylcyclohexyl)acetimidamide

Prepared by General Procedures D, F, J, K, L, and M. In General Procedure d, 4-phenylcyclohexanone was used. In General Procedure J, 4-bromoaniline was used. In General Procedure L, K$_2$CO$_3$ was used in place of NaHCO$_3$. The product was isolated as an off-white solid. $^1$H NMR (400 MHz, CD$_3$OD): δ 7.46-7.40 (m, 2H), 7.28-7.18 (m, 2H), 7.13-7.07 (m, 3H), 7.05-6.98 (m, 2H), 2.51 (d, J=7.9 Hz, 2H), 2.45-2.35 (m, 1H), 1.80-1.40 (m, 9H) ppm. m/z 387.2 (M+H)$^+$.

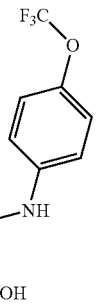

(cis)-N'-Hydroxy-2-(4-phenylcyclohexyl)-N-(4-(trifluoromethoxy)phenyl)-acetimidamide Prepared by General Procedures D, F, J, K, L, and M. In General Procedure D, 4-phenylcyclohexanone was used. In General Procedure J, 4-trifluoromethoxyaniline was used. In General Procedure L, K$_2$CO$_3$ was used in place of NaHCO$_3$. The product was isolated as an off-white solid. $^1$H NMR (400 MHz, CD$_3$OD) δ 7.27-7.01 (m, 9H), 2.51 (d, J=7.8 Hz, 2H), 2.44-2.35 (m, 1H), 1.79-1.39 (m, 9H) ppm. m/z 393.2 (M+H)$^+$.

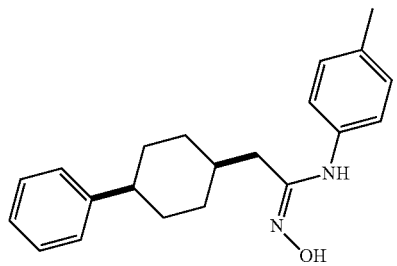 [SMILES: Cc1ccc(N/C(C[C@H]2CC[C@@H](c3ccccc3)CC2)=N\O)cc1]

(cis)-N-(4-Methylphenyl)-N'-hydroxy-2-(4-phenylcyclohexyl)acetimidamide

Prepared by General Procedures D, E, J, K, L, and M. In General Procedure D, 4-phenylcyclohexanone was used. In General Procedure J, 4-methylaniline was used. In General Procedure L, K$_2$CO$_3$ was used in place of NaHCO$_3$. The product was isolated as an off-white solid. $^1$H NMR (400 MHz, CD$_3$OD): δ 7.36-6.85 (m, 9H), 2.56-2.17 (m, 6H), 1.81-1.20 (m, 9H) ppm. m/z 323.2 (M+H)$^+$.

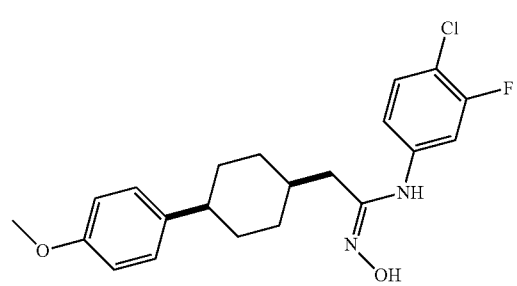 [SMILES: COc1ccc([C@H]2CC[C@@H](C/C(=N/O)Nc3ccc(Cl)c(F)c3)CC2)cc1]

(cis)-N-(4-Chloro-3-fluorophenyl)-N'-hydroxy-2-(4-(4-methoxyphenyl)cyclohexyl)-acetimidamide Prepared from (cis)-methyl 2-((1,4)4-(4-methoxyphenyl) cyclohexyl)acetate by General Procedures G, I, K, L, and M.

In General Procedure I, 3-fluoro-4-chloroaniline was used. In General Procedure L, K₂CO₃ was used in place of NaHCO₃. The product was isolated as an off-white solid. ¹H NMR (400 MHz, CDCl₃): δ 7.33 (t, J=8.4 z Hz, 1H), 7.08 (d, J=8.7 Hz, 2H), 6.90-6.75 (m, 4H), 3.77 (s, 3H), 2.48 (d, J=7.7 Hz, 3H), 1.83 (s, 1H), 1.62-1.45 (m, 8H) ppm. m/z 391.2 (M+H)⁺.

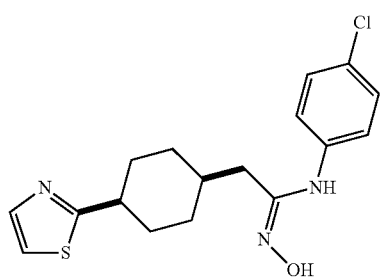 [SMILES: O/N=C(/C[C@H]1CC[C@@H](c2nccs2)CC1)Nc1ccc(Cl)cc1]

(cis)-N-(4-Chlorophenyl)-N'-hydroxy-2-(4-(thiazol-2-yl)cyclohexyl)-acetimidamide

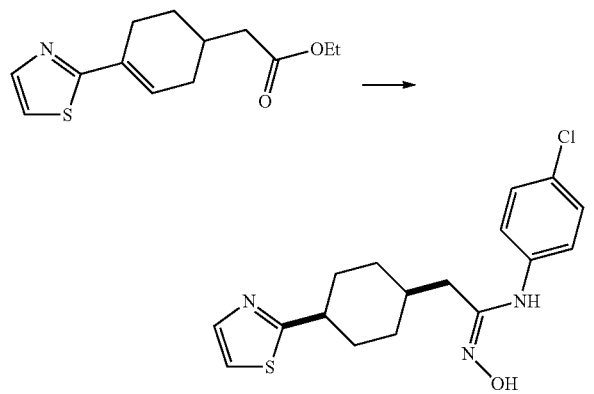

A solution of tributyl-2-thiazolylstannane (1.0 equivalents), ethyl 2-(4-((((trifluoromethyl)sulfonyl)oxy)cyclohex-3-en-1-yl)acetate (1.0 equivalents), Pd(PPh₃)₄ (0.1 equivalents), CuI (0.2 equivalents), and LiCl (1.5 equivalents) in dioxane (0.1 M) was heated at 100° C. for 16 h. The mixture was concentrated under reduced pressure and the reside was was purified by silica gel chromatography (0-20% EtOAc in Hexanes) to give ethyl 2-(4-(thiazol-2-yl)cyclohex-3-en-1-yl)acetate.

General Procedures P, J, K, L, and M were employed. In General Procedure P, Pd/C and EtOH were used. In General Procedure J, 4-chloroaniline was used. In General Procedure L, K₂CO₃ was used in place of NaHCO₃. The product was isolated as an off-white solid. ¹H NMR (400 MHz, CDCl₃): δ 7.65 (d, J=3.3 Hz, 1H), 7.31-7.26 (m, 2H), 7.18 (d, J=3.3 Hz, 1H), 7.03-6.95 (m, 2H), 3.17-3.04 (m, 1H), 2.30 (d, J=7.4 Hz, 2H), 2.14-1.34 (m, 9H) ppm. m/z 175.6 (M+2H)²⁺.

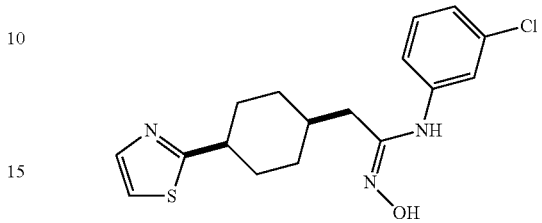

(cis)-N-(3-Chlorophenyl)-N'-hydroxy-2-(4-(thiazol-2-yl)cyclohexyl)acetimidamide

Prepared using the same Procedures as those used to prepare (cis)-N-(4-chlorophenyl)-N-hydroxy-2-(4-(thiazol-2-yl)cyclohexyl)acetimidamide replacing 4-chloroaniline with 4-chloroaniline in General Procedure J. The desired product was isolated as an off-white solid. ¹H NMR (400 MHz, CDCl₃): δ 7.66 (d, J=3.3 Hz, 1H), 7.23 (d, J=8.0 Hz, 1H), 7.18 (d, J=3.3 Hz, 1H), 7.13-7.03 (m, 3H), 6.94 (ddd, J=8.0, 2.1, 0.9 Hz, 1H), 3.16-3.07 (m, 1H), 2.35 (d, J=7.4 Hz, 2H), 2.01-1.33 (m, 9H) ppm. m/z 175.6 (M+2H)²⁺.

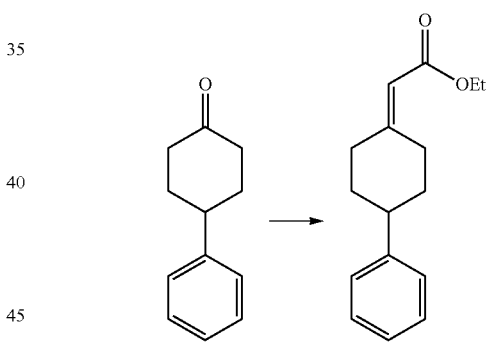

Ethyl 2-(4-phenylcyclohexylidene)acetate

Sodium tert-butoxide (6.1 g, 63.2 mmol) was suspended in THF (72 mL) and cooled to 0° C. Triethylphosphonoacetate (12.5 mL, 63.2 mmol) was added dropwise and the mixture was warmed to rt. After warming the solution became colorless. The mixture was cooled to 0° C. and a THF (72 mL) solution of 4-phenylcyclohexanone (10 g, 57.5 mmol) was added dropwise over 30 min. After addition, the mixture was warmed to rt during which time the mixture became biphasic. Stirring was continued for 1 h then the solvent was removed under reduced pressure. The residue was dissolved in EtOAc (150 mL) and washed with 1 M HCl (100 mL). The organic layer was dried with anhydrous Na₂SO₄, concentrated under reduced pressure and purified by silica gel chromatography (0-30% EtOAc in hexanes) which afforded the desired product as a clear oil (13.3 g, 95%). ¹H NMR (400 MHz, CDCl₃): δ 7.35-7.26 (m, 2H), 7.23-7.15 (m, 3H), 5.68 (s, 1H), 4.15 (d, J=7.5 Hz, 2H), 4.03-3.89 (m, 1H), 2.79 (tt, J=12.2, 3.4 Hz, 1H), 2.49-2.28 (m, 2H), 2.13-1.97 (m, 3H), 1.74-1.59 (m, 2H), 1.36-1.22 (m, 3H) ppm.

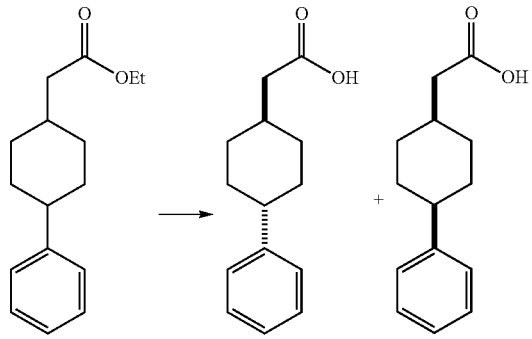

(trans)-2-(4-Phenylcyclohexyl)acetic acid and (cis)-2-(4-phenylcyclohexyl)acetic acid To a solution of ethyl 2-(4-phenylcyclohexyl)acetic acid (5.8 g, 23.5 mmol, 1.0 equiv.) in EtOH (1.0 M) was added an equal volume of aqueous LiOH solution (7.25 M, 145 mmol). The mixture was stirred vigorously, heated to 50° C. for 1 h and then diluted with 50 mL of water and further heated to 50° C. for 5 h. The mixture was then cooled to rt and the solids were filtered, washing carefully with cold, aqueous 5% LiOH solution (2×10 mL). The wet filter cake was then partitioned between EtOAc (40 mL) and 6 N HCl (25 mL) until all solids dissolved. The layers were separated and the organic layer was concentrated under reduced pressure to give the pure trans-diastereomer.

The cis diastereomer was obtained by taking the filtrate of the filtration and acidifying it to pH ~2 with aqueous 3N HCl. The filtrate was then extracted with EtOAc (50 mL) to yield the cis diastereomer as the major product.

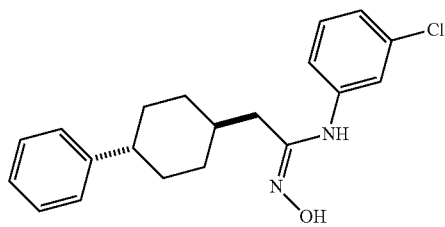 [SMILES: O/N=C(/C[C@H]1CC[C@H](c2ccccc2)CC1)Nc1cccc(Cl)c1]

(trans)-N-(3-Chlorophenyl)-N'-hydroxy-2-(4-phenyl-cyclohexyl)acetimidamide

Prepared using General Procedures H, K, L, and M, employing (trans)-2-(4-phenylcyclohexyl)-acetic acid (400 mg) and 3-chloroaniline (0.39 mL) in General Procedure H. The final product was purified using silica chromatography (0 to 40% EtOAc in hexanes) to afford the desired product as a white foam. $^1$H-NMR (400 MHz; CDCl$_3$): δ7.30-7.23 (m, 3H), 7.19-7.11 (m, 4H), 7.09 (t, J=2.0 Hz, 1H), 6.96 (ddd, J=8.0, 2.1, 1.0 Hz, 1H), 2.44-2.37 (m, 1H), 2.31 (d, J=7.1 Hz, 2H), 1.85 (d, J=10.5 Hz, 4H), 1.51-1.44 (m, 1H), 1.43-1.31 (m, 2H), 1.14-0.95 (m, 2H) ppm. m/z 343.2 (M+H)$^+$.

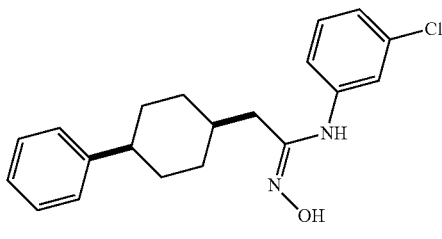 [SMILES: O/N=C(/C[C@H]1CC[C@@H](c2ccccc2)CC1)Nc1cccc(Cl)c1]

(cis)-N-(3-Chlorophenyl)-N'-hydroxy-2-(4-phenyl-cyclohexyl)acetimidamide

Prepared using General Procedures H, K, L, and M, employing (cis)-2-(4-phenylcyclohexyl)-acetic acid (300 mg) and 3-chloroaniline (0.30 mL) in General Procedure H. The final product was purified using silica chromatography (0 to 100% EtOAc in hexanes) to afford the desired product as a white foam. $^1$H-NMR (400 MHz; CDCl$_3$): δ 7.29-7.21 (m, 3H), 7.19-7.04 (m, 6H), 6.95 (ddd, J=8.0, 2.2, 1.0 Hz, 1H), 2.51-2.45 (m, 3H), 1.89-1.81 (m, 1H), 1.66-1.51 (m, 8H) ppm. m/z 343.2 (M+H)$^+$.

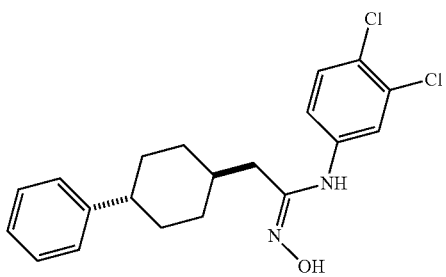 [SMILES: O/N=C(/C[C@H]1CC[C@H](c2ccccc2)CC1)Nc1ccc(Cl)c(Cl)c1]

(trans)-N-(3,4-Dichlorophenyl)-N'-hydroxy-2-(4-phenylcyclohexyl)acetimidamide

Prepared using General Procedures H, K, L, and M, employing (trans)-2-(4-phenylcyclohexyl)-acetic acid (300 mg) and 3,4-dichloroaniline (444 mg) in General Procedure H. The final product was purified using silica chromatography (0 to 100% EtOAc in hexanes) to afford the desired product as a white solid. $^1$H-NMR (400 MHz; CDCl$_3$): δ 7.39 (d, J=8.5 Hz, 1H), 7.29-7.23 (m, 2H), 7.18-7.15 (dd, J=8.8, 2.7 Hz, 4H), 6.92 (dd, J=8.6, 2.5 Hz, 1H), 2.46-2.37 (m, 1H), 2.27 (d, J=7.0 Hz, 2H), 1.88-1.82 (m, 4H), 1.52-1.31 (m, 3H), 1.06 (dq, J=12.9, 3.3 Hz, 2H) ppm. m/z 377.1 (M+H)$^+$.

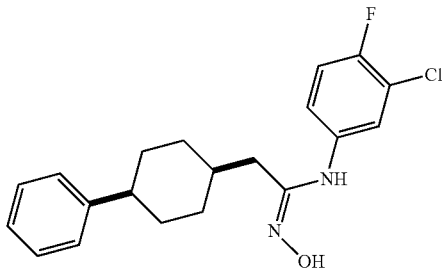

(cis)-N-(3-Chloro-4-fluorophenyl)-N'-hydroxy-2-(4-phenylcyclohexyl)-acetimidamide Prepared using General Procedures H, K, L, and M, employing (cis)-2-(4-phenylcyclohexyl)acetic acid (200 mg) and 3-chloro-4-fluoroaniline (173 mg) in General Procedure H. The final product was purified using silica chromatography (0 to 100% EtOAc in hexanes) to afford the desired product as a white solid. $^1$H-NMR (400 MHz; CDCl$_3$): δ 7.30-7.21 (m, 3H), 7.20-7.06 (m, 4H), 6.96 (ddd, J=8.7, 4.1, 2.7 Hz, 2H), 2.54-2.46 (m, 1H), 2.42 (d, J=7.7 Hz, 2H), 1.89-1.75 (m, 1H), 1.68-1.49 (m, 8H) ppm. m/z 361.2 (M+H$^+$).

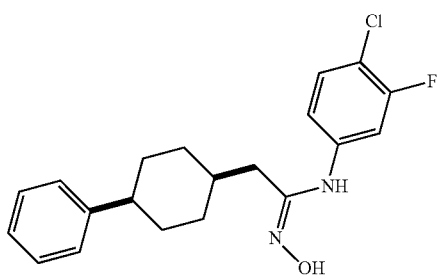

(cis)-N-(4-Chloro-3-fluorophenyl)-N'-hydroxy-2-(4-phenylcyclohexyl)-acetimidamide Prepared using General Procedures H, K, L, and M, employing (cis)-2-(4-phenylcyclohexyl)acetic acid (200 mg) and 4-chloro-3-fluoroaniline (173 mg) in General Procedure H. The final product was purified using silica chromatography (0 to 100% EtOAc in hexanes) to afford the desired product as a white solid. $^1$H-NMR (400 MHz; CDCl$_3$): δ 7.32 (t, J=8.4 Hz, 1H), 7.29-7.21 (m, 2H), 7.20-7.09 (m, 3H), 6.84 (dd, J=10.2, 2.5 Hz, 1H), 6.76 (ddd, J=8.6, 2.3, 0.9 Hz, 1H), 2.51-2.49 (m, 3H), 1.91-1.78 (m, 1H), 1.70-1.46 (m, 8H) ppm. m/z 361.2 (M+H)$^+$.

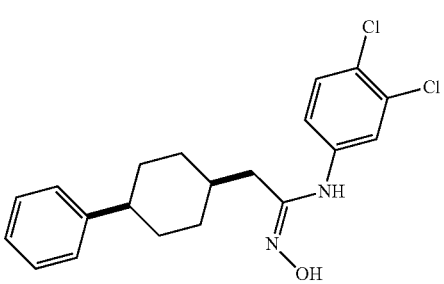

(cis)-N-(3,4-Dichlorophenyl)-N'-hydroxy-2-(4-phenylcyclohexyl)acetimidamide

Prepared using General Procedures H, K, L, and M, employing (cis)-2-(4-phenylcyclohexyl)-acetic acid (150 mg) and 3,4-dichloroaniline (133 mg) in General Procedure H. The final product was purified using silica chromatography (0 to 100% EtOAc in hexanes) to afford the desired product as a white solid. $^1$H-NMR (400 MHz; CDCl$_3$): δ 7.37 (d, J=8.6 Hz, 1H), 7.30-7.21 (m, 3H), 7.20-7.12 (m, 4H), 6.87 (dd, J=8.6, 2.6 Hz, 1H), 2.50-2.47 (m, 3H), 1.93-1.75 (m, 1H), 1.62-1.56 (m, 8H) ppm. m/z 377.3 (M+H)$^+$.

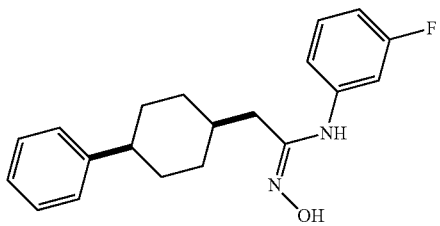

(cis)-N-(3-Fluorophenyl)-N'-hydroxy-2-(4-phenylcyclohexyl)acetimidamide

Prepared using General Procedures H, K, L, and M employing, (cis)-2-(4-phenylcyclohexyl)-acetic acid (150 mg) and 3-fluoroaniline (92 mg) in General Procedure H. The final product was purified using silica chromatography (0 to 100% EtOAc in hexanes) to afford the desired product as a white solid. $^1$H-NMR (400 MHz; CDCl$_3$): δ 7.33-7.21 (m, 3H), 7.15 (dd, J=10.8, 4.4 Hz, 4H), 6.87-6.82 (m, 2H), 6.79 (dt, J=10.2, 2.3 Hz, 1H), 2.52-2.46 (m, 3H), 1.91-1.80 (m, 1H), 1.64-1.57 (m, 8H) ppm. m/z 327.2 (M+H)$^+$.

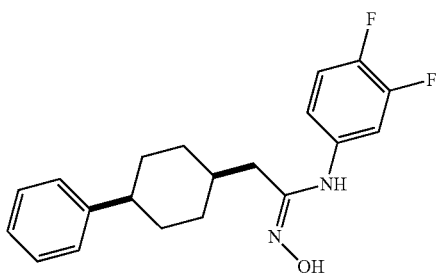

(cis)-N-(3,4-Difluorophenyl)-N'-hydroxy-2-(4-phenylcyclohexyl)acetimidamide

Prepared using General Procedures H, K, L, and M, employing (cis)-2-(4-phenylcyclohexyl)-acetic acid (150 mg) and 3,4-difluoroaniline (0.08 mL) in General Procedure H. The final product was purified using silica chromatography (0 to 100% EtOAc in hexanes) to afford the desired product as a white solid. $^1$H-NMR (400 MHz; CDCl$_3$): δ 7.31-7.21 (m, 2H), 7.20-7.06 (m, 4H), 6.96-6.91 (m, 2H), 6.85-6.78 (m, 1H), 2.54-2.46 (m, 1H), 2.42 (d, J=7.6 Hz, 2H), 1.89-1.74 (m, 1H), 1.67-1.50 (m, 8H) ppm. m/z 345.3 (M+H)$^+$.

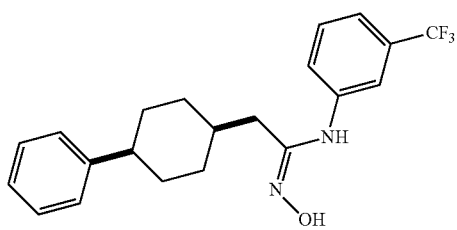

(cis)-N'-Hydroxy-2-(4-phenylcyclohexyl)-N-(3-(trifluoromethyl)phenyl)-acetimidamide Prepared using General Procedures H, K, L, and M, employing (cis)-2-(4-phenylcyclohexyl)acetic acid (200 mg) and 3-(trifluoromethyl)aniline (0.15 mL) in General Procedure H. The final product was purified using silica chromatography (0 to 50% EtOAc in hexanes) to afford the desired product as a white solid. ¹H-NMR (400 MHz; CDCl₃): δ 7.49-7.35 (m, 2H), 7.32 (s, 1H), 7.29-7.10 (m, 7H), 2.58-2.43 (m, 3H), 1.92-1.79 (m, 1H), 1.68-1.49 (m, 8H) ppm. m/z 377.3 (M+H)⁺.

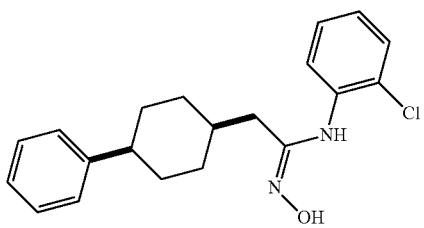

(cis)-N-(2-Chlorophenyl)-N'-hydroxy-2-(4-phenyl-cyclohexyl)acetimidamide

Prepared using General Procedures H, K, L, and M, employing (cis)-2-(4-phenylcyclohexyl)-acetic acid (100 mg) and 2-chloroaniline (0.07 mL) in General Procedure H. The final product was purified using silica chromatography (0 to 20% EtOAc in hexanes) to afford the desired product as a white solid. ¹H-NMR (400 MHz; CDCl₃): δ 7.42 (dd, J=8.0, 1.4 Hz, 1H), 7.28-7.18 (m, 5H), 7.16-7.07 (m, 4H), 2.49-2.41 (m, 3H), 1.87-1.69 (m, 1H), 1.60-1.52 (m, 8H) ppm. m/z 343.2 (M+H)⁺.

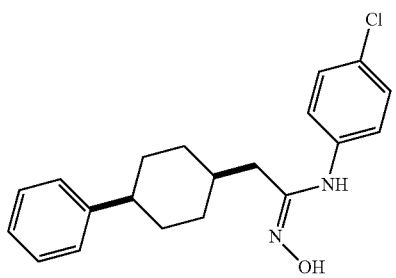

(cis)-N-(4-Chlorophenyl)-N'-hydroxy-2-(4-phenyl-cyclohexyl)acetimidamide

Prepared using General Procedures H, K, L, and M, employing (cis)-2-(4-phenylcyclohexyl)-acetic acid (100 mg) and 4-chloroaniline (82 mg) in General Procedure H. The final product was purified using silica chromatography (0 to 30% EtOAc in hexanes) to afford the desired product as a white solid. ¹H-NMR (400 MHz; CDCl₃): δ 7.31-7.23 (m, 4H), 7.17-7.14 (m, 3H), 7.04-6.97 (m, 2H), 2.47 (d, J=7.6 Hz, 3H), 1.87-1.80 (m, 1H), 1.62-1.52 (m, 8H) ppm. m/z 343.2 (M+H)⁺.

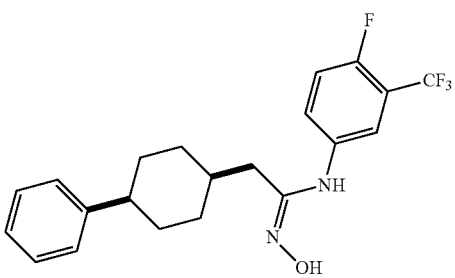

(cis)-N-(4-Fluoro-3-(trifluoromethyl)phenyl)-N'-hydroxy-2-(4-phenylcyclohexyl)acetimidamide Prepared using General Procedures I, K, L, and M, employing (cis)-2-(4-phenylcyclohexyl)acetic acid (120 mg) and 4-fluoro-3-(trifluoromethyl)-aniline (0.14 mL) in General Procedure I. The final product was purified using silica chromatography (10 to 50% EtOAc in hexanes) to afford the desired product as a white solid. ¹H-NMR (400 MHz; CDCl₃): δ 7.36-7.05 (m, 9H), 2.49-2.44 (m, 3H), 1.84-1.74 (m, 1H), 1.68-1.44 (m, 8H) ppm. m/z 395.2 (M+H)⁺.

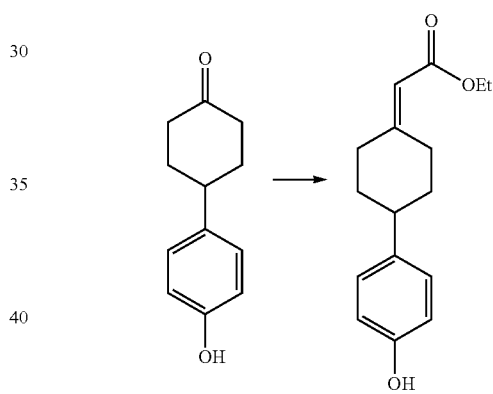

Ethyl 2-(4-(4-hydroxyphenyl)cyclohexylidene)acetate

To an oven-dried flask (Flask #1) was added NaH (60% dispersion in oil, 11.8 g, 295 mmol) and 120 mL of THF and cooled to 0° C. Tritethylphosphonoacetate (46.9 mL, 236 mmol) was dissolved in 250 mL of THF and added dropwise to the NaH mixture over 1 hour. After the addition, the mixture was stirred for 1 hour at rt.

To a separate flask was added 37.47 grams (196.9 mmol) of 4-(4-hydroxyphenyl)cyclohexanone was dissolved in 250 mL THF with heating. After cooling this solution to rt, it was CAREFULLY added over 45 minutes to a another flask (Flask #2) which contained a 0° C. mixture of NaH (60% dispersion in oil, 8.67 g, 216 mmol) in 100 mL THF. After addition, the mixture was stirred at rt for 2 hours until the mixture becomes a clear solution. Once this solution was clear, Flask #1 was cooled back to 0° C. and the contents of Flask #2 are added via cannulation. After the addition, the mixture was warmed back to rt and stirred for 2 hours.

The mixture was quenched by careful addition of ice and water (1 L) and subsequently extracted with EtOAc (3×500 mL) and the combined organics were washed with brine (1 L), dried over sodium sulfate, filtered, and concentrated under reduced to provide ethyl 2-(4-(4-hydroxyphenyl)cyclohexylidene)acetate in 97% yield as a white solid.

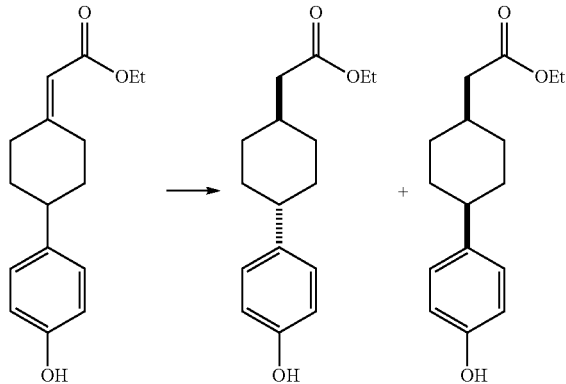 [SMILES: CCOC(=O)C=C1CCC(c2ccc(O)cc2)CC1 ; CCOC(=O)C[C@H]1CC[C@H](c2ccc(O)cc2)CC1 ; CCOC(=O)C[C@H]1CC[C@@H](c2ccc(O)cc2)CC1]

(trans)-Ethyl 2-4-(4-hydroxyphenyl)cyclohexyl)acetate and (cis)-Ethyl 2-4-(4-hydroxyphenyl)cyclohexyl)acetate To a solution of ethyl 2-(4-(4-hydroxyphenyl)-cyclohexylidene)acetate (9.74 g, 35.8 mmol) in EtOAc (180 mL) was added 10% palladium on carbon (0.974 g). The solution was bubbled with hydrogen gas for 5 min before being capped and stirred under a hydrogen balloon 16 h. The mixture was filtered through celite plug and the plug was washed with EtOAc. The filtrate was concentrated under reduced pressure. The solie was then recrystallized from an EtOAc/hexanes (8 mL/10 mL). The solid was isolated by filtration to give the pure trans isomer. The filtrate was concentrated under reduced pressure to yield a solid with a 2:1 ratio of cis:trans diastereomers.

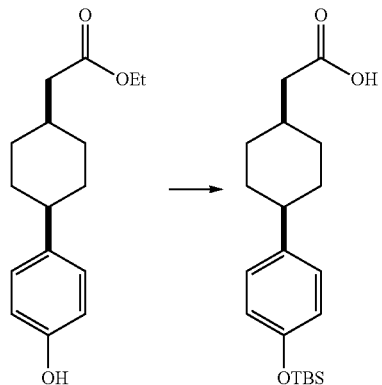 [SMILES: CCOC(=O)C[C@H]1CC[C@@H](c2ccc(O)cc2)CC1 ; CC(C)(C)[Si](C)(C)Oc1ccc([C@H]2CC[C@@H](CC(=O)O)CC2)cc1]

(cis)-2-4-(4-((tert-Butyldimethylsilyl)oxy)phenyl)cyclohexyl)acetic acid

General Procedure G utilizing (cis)-ethyl 2-4-(4-hydroxyphenyl)cyclohexyl)acetate was used to give (cis)-2-(4-(4-hydroxyphenyl)cyclohexyl)acetic acid. To a solution of (cis)-2-(4-(4-hydroxyphenyl)cyclohexyl)acetic acid (3.0 g, 12.8 mmol) in DMF (100 mL) was added imidazole (2.18 g, 32.0 mmol). The mixture was cooled to 0° C. and then tert-butyldimethylsilyl chloride (4.05 g, 26.9 mmol) was added in portions. The mixture was then slowly warm to rt and stir at rt for 16 h. Saturated aqueous ammonium chloride (100 mL) was added. The mixture was then extracted with EtOAc (3×100 mL) and the combined organic layers were washed with water (2×100 mL) and brine (100 mL). The organic layer was dried over sodium sulfate and concentration under reduced pressure. The residue was purified by silica chromatography (0 to 100% EtOAc in hexanes) to colorless oil. The colorless oil was dissolved in THF (50 mL) and solid $K_2CO_3$ (2.6 g, 18.8 mmol) was added. The mixture was then stirred 16 h before the addition of water (6 mL) followed by stirring for 1 h. The pH of the solution was then adjusted using 0.2N HCl until pH ~7. The mixture was then extracted with EtOAc (3×50 mL) and the combined organics were dried over sodium sulfate, and concentrated under reduced pressure. The crude mixture was purified by silica chromatography (0 to 100% EtOAc in hexanes) to isolate (cis)-2-4-(4-((tert-butyldimethylsilyl)oxy)phenyl)cyclohexyl)acetic acid.

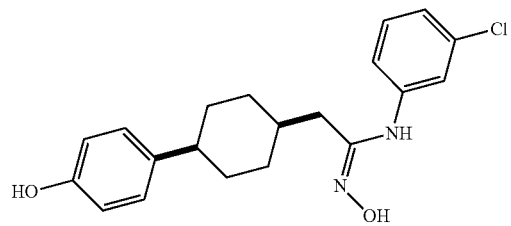

(cis)-N-(3-Chlorophenyl)-N'-hydroxy-2-(4-(4-hydroxyphenyl)cyclohexyl)-acetimidamide

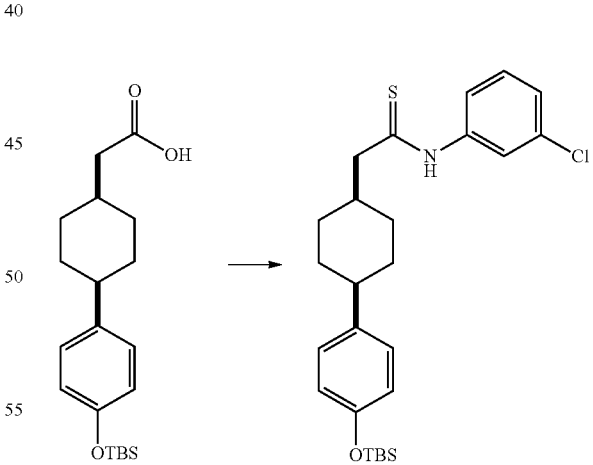

General Procedures H, K, were used, employing (cis)-2-4-(4-((tert-butyldimethylsilyl)oxy)phenyl)cyclohexyl)acetic acid (1.50 g) and 3-chloroaniline (0.55 mL) in General Procedure H to give (cis)-2-(4-(4-((tert-butyldimethylsilyl)oxy)phenyl)cyclohexyl)-N-(3-chlorophenyl)ethanethioamide.

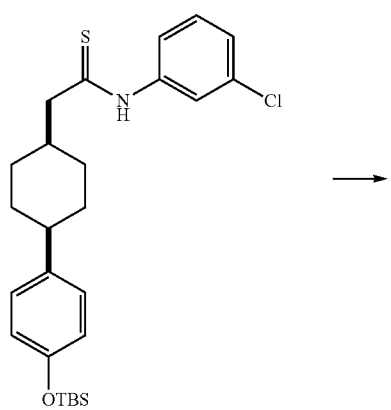

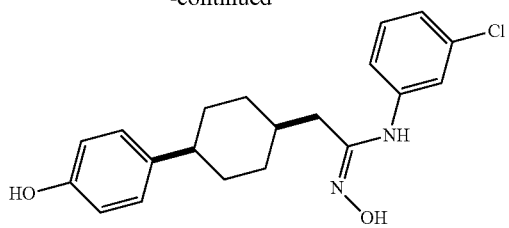

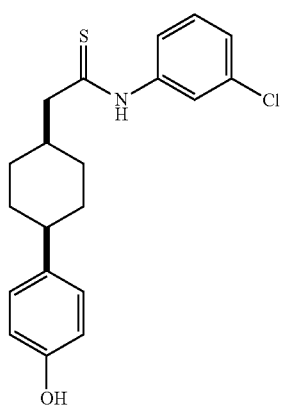

General Procedures L and M were used. General Procedure M employed 30 equivalents of hydroxylamine solution (50 wt. %) and heating the mixture at 50° C. The final product was purified using silica chromatography (30 to 50% EtOAc in hexanes) to afford the desired product as a white foam. $^1$H-NMR (400 MHz; CDCl$_3$): δ 7.28-7.20 (m, 2H), 7.16-7.09 (m, 1H), 7.08 (t, J=2.1 Hz, 1H), 7.03-6.90 (m, 3H), 6.76-6.67 (m, 2H), 2.49 (d, J=7.7 Hz, 2H), 2.45-2.35 (m, 1H), 1.84-1.74 (m, 1H), 1.62-1.43 (m, 8H) ppm. m/z 359.2 (M+H)$^+$.

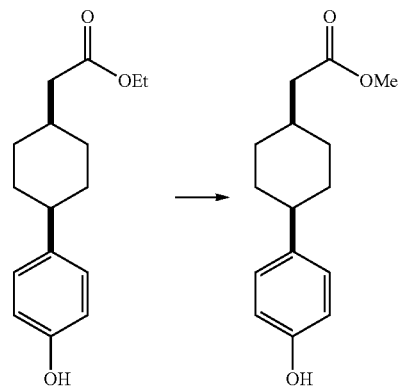 [SMILES: CCOC(=O)C[C@H]1CC[C@@H](c2ccc(O)cc2)CC1 ; COC(=O)C[C@H]1CC[C@@H](c2ccc(O)cc2)CC1]

To a solution of (cis)-2-(4-(4-((tert-butyldimethylsilyl)oxy)phenyl)cyclohexyl)-N-(3-chlorophenyl)ethanethioamide (180 mg, 0.380 mmol) in THF (1.3 mL) at 0° C. was added TBAF (1.0M in THF, 0.418 mL). The mixture was warmed to rt and stirred at rt for 3 h. The mixture was quenched by slow addition of water (1 mL). The mixture was extracted with EtOAc (3×10 mL) and the combined organics were dried over sodium sulfate, and concentrated under reduced pressure. The residue was purified by silica chromatography (0 to 100% EtOAc in hexanes) to give (cis)-N-(3-chlorophenyl)-2-(4-(4-hydroxyphenyl)cyclohexyl)ethanethioamide.

(cis)-Methyl 2-4-(4-hydroxyphenyl)cyclohexyl)acetate (Cis)-2-(4-(4-hydroxyphenyl)cyclohexyl)acetic acid (1.7 g, 7.25 mmol) was dissolved in methanol (15 mL) and one drop of concentrated sulfuric acid. The mixture was heated at reflux for 16 h. The mixture was then cooled to rt and aqueous saturated bicarbonate was added until the pH of the mixture was ~7. The mixture was then extracted with EtOAc (3×25 mL) and the combined organics were washed with brine (50 mL), dried over sodium sulfate, and concentrated to give (cis)-methyl 2-4-(4-hydroxyphenyl)cyclohexyl)acetate as a pale yellow solid.

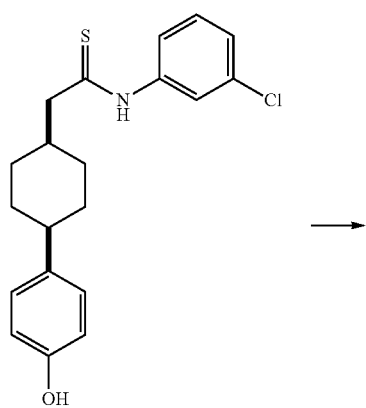

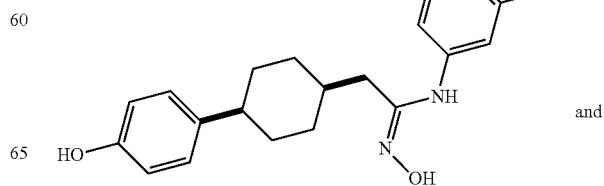

and

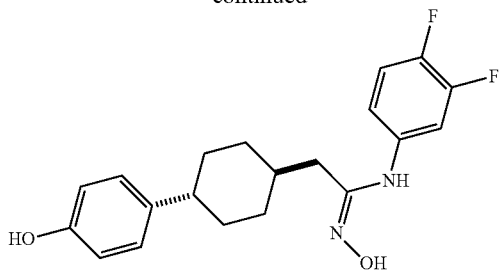

(cis)-N-(3-Chlorophenyl)-N'-hydroxy-2-(4-(4-morpholinophenyl)cyclohexyl)-acetimidamide and (trans)-N-(3-chlorophenyl)-N'-hydroxy-2-(4-(4-morpholino-phenyl)cyclohexyl)acetimidamide Prepared using General Procedures J, K, L, and M, employing (cis)-methyl 2-4-(4-hydroxyphenyl)cyclohexyl) acetate (300 mg) and 3,4-difluoroaniline (0.36 mL) in General Procedure J. The final product was purified using silica chromatography (30 to 80% EtOAc in hexanes) to afford the desired product as a white solid in a 2:1 cis: trans diastereomeric ratio. $^1$H-NMR (400 MHz; CDCl$_3$): δ 7.16-7.09 (m, 1H), 7.04-6.98 (m, 2H), 6.97-6.88 (m, 1H), 6.83-6.80 (m, 1H), 6.76-6.70 (m, 2H), 2.46-2.18 (m, 3H), 1.83-1.76 (m, 3H), 1.57-1.51 (m, 4H), 1.42-1.33 (m, 1H), 1.17-0.98 (m, 1H) ppm. m/z 361.2 (M+H)$^+$.

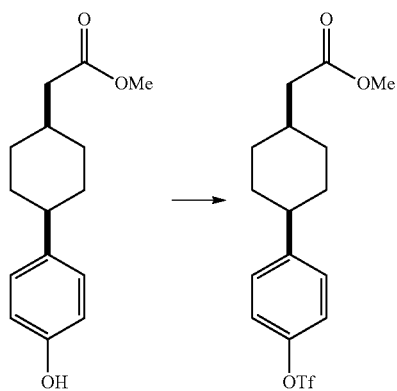 [SMILES: COC(=O)C[C@H]1CC[C@@H](c2ccc(O)cc2)CC1 ; COC(=O)C[C@H]1CC[C@@H](c2ccc(OS(=O)(=O)C(F)(F)F)cc2)CC1]

Methyl 2-(4-(4-(((trifluoromethyl)sulfonyl)oxy)phenyl)cyclohexyl)acetate

To a 0° C. solution of (cis)-methyl 2-4-(4-hydroxyphenyl)cyclohexyl)acetate (1.5 g, 6.04 mmol) in dichloromethane (30 mL) was added triflic anhydride (1.22 mL, 7.25 mmol). The mixture was stirred at 0° C. for 20 min before triethylamine (2.1 mL, 15.1 mmol) was added dropwise over 20 min. During this time, the color of the mixture turned red and then black. The mixture was held at 0° C. for 90 min and then warmed to rt and stirred at rt for 16 h. The mixture was carefully quenched with the addition of water (20 mL). The mixture was then extracted with dichloromethane (3×20 mL) and the combined organics were washed successively with saturated aqueous bicarbonate (20 mL) and brine (20 mL) before drying over sodium sulfate and concentration under reduced pressure. The crude residue was purified by silica chromatography (0 to 50% EtOAc in hexanes) to give the product as a yellow oil as a 2:1 mixture of cis: trans diastereomers.

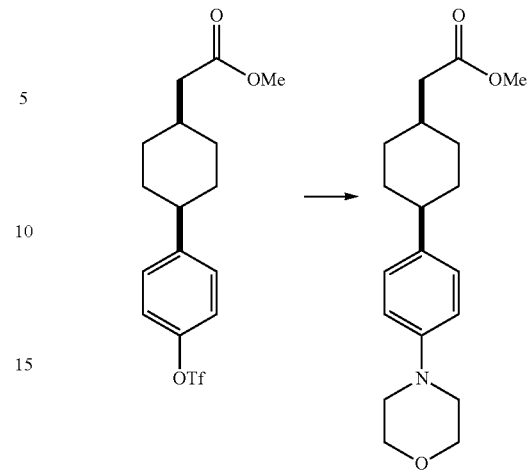

Methyl 2-(4-(4-morpholinophenyl)cyclohexyl)acetate

In a sealed tube was combined methyl 2-(4-(4-(((trifluoromethyl)sulfonyl)oxy)phenyl)cyclohexyl)acetate (760 mg, 2.0 mmol, 2:1 dr), morpholine (0.22 mL, 2.6 mmol), palladium acetate (44 mg, 0.20 mmol), Xphos (96 mg, 0.20 mmol), cesium carbonate (652 mg, 2.0 mmol), and toluene (10 mL). This mixture was then degassed with N$_2$ (g) for 10 min and subsequently heated at 116° C. for 16 h. The mixture was then cooled to rt and filtered through a plug of celite. The plug of celite was washing thoroughly with EtOAc. The filtrate was concentrated under reduced pressure and the reside was purified by silica chromatography (20 to 100% EtOAc in hexanes) to give isolated methyl 2-(4-(4-morpholinophenyl)cyclohexyl)acetate as a pale yellow solid in a 2:1 cis: trans diastereomeric ratio.

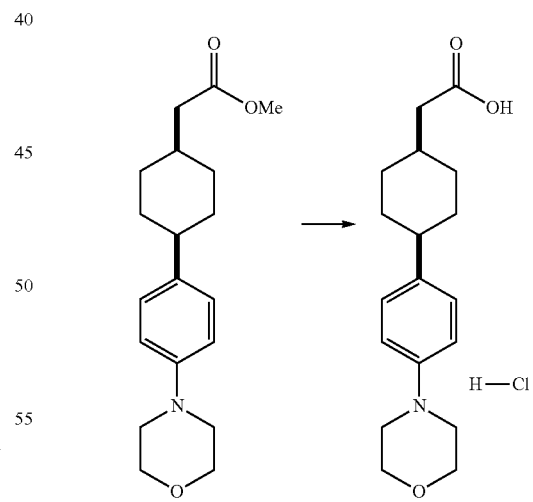

2-(4-(4-Morpholinophenyl)cyclohexyl)acetic acid hydrochloride

A round-bottom flask was charged with methyl 2-(4-(4-morpholinophenyl)cyclohexyl)acetate (650 mg, 2.05 mmol) and ethanol (7 mL). Lithium hydroxide (61 mg, 2.56 mmol) was dissolved in water (3 mL) and added to the ethanol solution. The mixture was stirred at 60° C. for 16 h at which time lithium hydroxide (40 mg in 1 mL water) was added and the mixture was heated at 70° C. for an additional 3 h. The solution was cooled to 0° C. and acidified to pH ~2 with HCl (2M in Et₂O). The mixture was concentrated under reduced pressure to give the title compound as an orange foam.

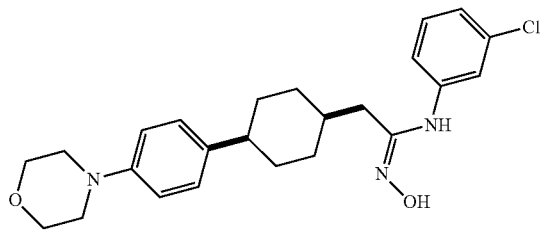

(cis)-N-(3-Chlorophenyl)-N'-hydroxy-2-(4-(4-morpholinophenyl)cyclohexyl)-acetimidamide Prepared using General Procedures I, K, L, and M employing 2-(4-(4-morpholinophenyl)cyclohexyl)acetic acid hydrochloride (150 mg) and 3-chloroaniline (0.08 mL) in General Procedure I. The final product was purified using silica chromatography (0 to 100% EtOAc in hexanes) to afford the desired product as a white solid. ¹H-NMR (400 MHz; CDCl₃): δ 7.29-7.20 (m, 2H), 7.16-7.02 (m, 4H), 6.95 (ddd, J=8.0, 2.1, 0.9 Hz, 1H), 6.85-6.80 (m, 2H), 3.90-3.80 (m, 4H), 3.16-3.04 (m, 4H), 2.48 (d, J=7.6 Hz, 2H), 2.46-2.38 (m, 1H), 1.87-1.77 (m, 1H), 1.65-1.46 (m, 8H) ppm. m/z 428.2 (M+H)⁺.

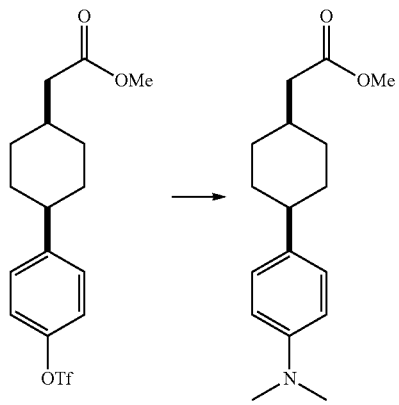 [SMILES: COC(=O)C[C@H]1CC[C@@H](c2ccc(OS(=O)(=O)C(F)(F)F)cc2)CC1 ; COC(=O)C[C@H]1CC[C@@H](c2ccc(N(C)C)cc2)CC1]

Methyl 2-(4-(4-(dimethylamino)phenyl)cyclohexyl)acetate

In a sealed tube was combined methyl 2-(4-(4-(((trifluoromethyl)sulfonyl)oxy)phenyl)cyclohexyl)acetate (1.0 g, 2.63 mmol, 2:1 dr), dimethylamine (1.0M in THF, 5.25 mL, 5.26 mmol), palladium acetate (59 mg, 0.263 mmol), Xphos (125 mg, 0.263 mmol), cesium carbonate (837 mg, 2.63 mmol), and toluene (12 mL). This mixture was then degassed with N₂ for 10 min and subsequently heated at 116° C. for 16 h. The mixture was then cooled to rt and filtered through a plug of celite. The plug was washed thoroughly with EtOAc. The filtrate was then concentrated under reduced pressure and purified by silica chromatography (20 to 30% EtOAc in hexanes). The title compound was isolated as a clear oil in a 2:1 cis:trans diastereomeric ratio.

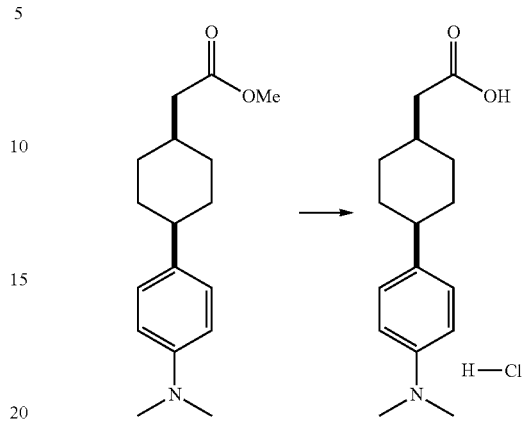

2-4-(4-(dimethylamino)phenyl)cyclohexyl)acetic acid hydrochloride

A round-bottom flask was charged with methyl 2-(4-(4-(dimethylamino)phenyl)cyclohexyl)acetate (600 mg, 2.18 mmol) and ethanol (8 mL). Lithium hydroxide (157 mg, 6.54 mmol) was dissolved in water (3 mL) and added to the ethanol solution. The mixture was stirred at 70° C. for 5 h. The solution was cooled to 0° C. and acidified to pH ~2 with HCl (2M in Et₂O). The was concentrated under reduced pressure to give the title compound as a brown oil which was used without further purification.

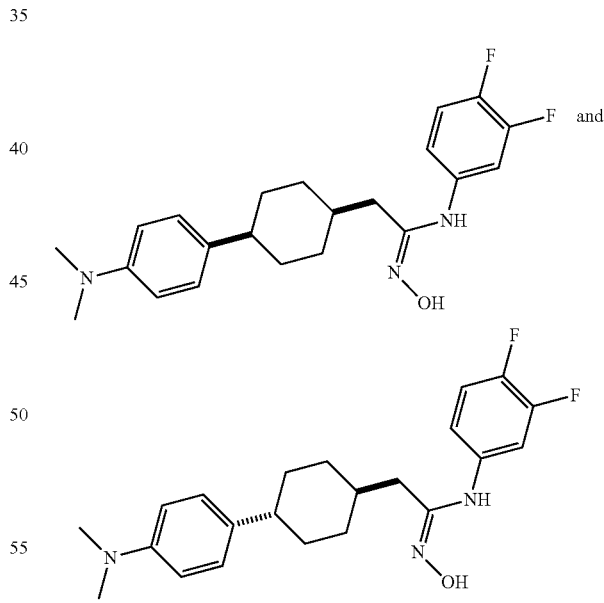

(cis)-N-(3,4-Difluorophenyl)-2-(4-(4-(dimethylamino)phenyl)cyclohexyl)-N'-hydroxyacetimidamide and (trans)-N-(3,4-difluorophenyl)-2-(4-(4-(dimethylamino)phenyl)cyclohexyl)-N'-hydroxyacetimidamide Prepared using General Procedures I, K, L, and M employing 2-4-(4-(dimethylamino)phenyl)cyclohexyl)acetic acid hydrochloride (300 mg) and 3,4-difluloroaniline (0.20 mL) in General Procedure I. The final product was purified using silica chromatography (20 to 60% EtOAc in hexanes) to afford the desired product as a white solid in a 2:1 cis:trans diastereomeric ratio. ¹H-NMR (400 MHz; CDCl₃): δ 7.22-6.98 (m, 4H), 6.94-6.90 (m, 1H), 6.86-6.77 (m, 1H), 6.73-6.62 (m, 2H), 2.90-2.88 (m, 6H), 2.44-2.22 (m, 3H), 1.81 (m, 2H), 1.60-1.54 (m, 5H), 1.37-1.26 (m, 1H, minor diasteromer), 1.09-0.95 (m, 1H, minor diasteromer).

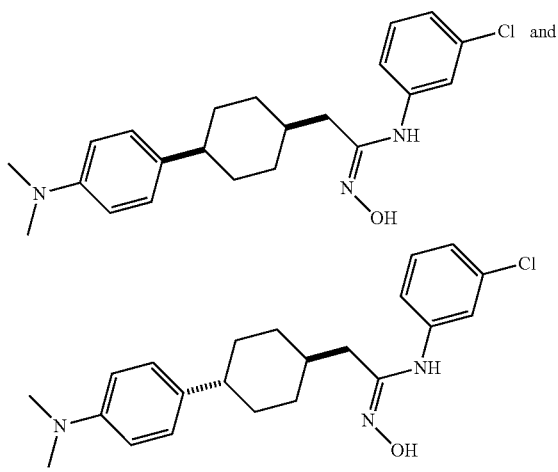

(cis)-N-(3-Chlorophenyl)-2-(4-(4-(dimethylamino) phenyl)cyclohexyl)-N'-hydroxyacetimidamide and (trans)-N-(3-chlorophenyl)-2-(4-(4-(dimethylamino) phenyl)-cyclohexyl)-N'-hydroxyacetimidamide Prepared using General Procedures I, K, L, and M employing 2-4-(4-(dimethylamino)phenyl)cyclohexyl)acetic acid hydrochloride (300 mg) and 3-chloroaniline (0.21 mL) in General Procedure I. The final product was purified using silica chromatography (20 to 60% EtOAc in hexanes) to afford the desired product as a white solid in a 2:1 cis:trans diastereomeric ratio. ¹H-NMR (400 MHz; CDCl₃): δ 7.30-7.21 (m, 2H), 7.21-7.01 (m, 4H), 6.96 (m, 1H), 6.74-6.61 (m, 2H), 2.94-2.85 (m, 6H), 2.54-2.25 (m, 3H), 1.84-1.82 (m, 2H), 1.66-1.47 (m, 5H), 1.38-1.27 (m, 1H, minor diastereomer), 1.10-0.98 (m, 1H, minor diastereomer).

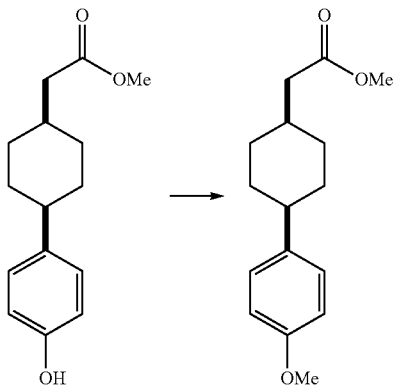 [SMILES: COC(=O)C[C@H]1CC[C@@H](c2ccc(O)cc2)CC1 ; COC(=O)C[C@H]1CC[C@@H](c2ccc(OC)cc2)CC1]

(cis)-Methyl 2-((1,4)4-(4-methoxyphenyl)cyclohexyl)acetate

To a round-bottom flask was added (cis)-methyl 2-4-(4-hydroxyphenyl)cyclohexyl)acetate (1.4 g, 5.64 mmol), cesium carbonate (3.21 g, 9.87 mmol), and DMF (57 mL). Then iodomethane (0.44 mL, 7.04 mmol) was added and the mixture was stirred at rt for 2 h. After this time, the mixture was cooled to 0° C., diluted with water (100 mL), and extracted with EtOAc (3×50 mL). The combined organic layers were washed with brine (50 mL), dried over sodium sulfate and concentration under reduced pressure. The residue was purified by silica chromatography (0 to 15% EtOAc in hexanes) to afford (cis)-methyl 2-((1,4)4-(4-methoxyphenyl)cyclohexyl)acetate as a colorless oil.

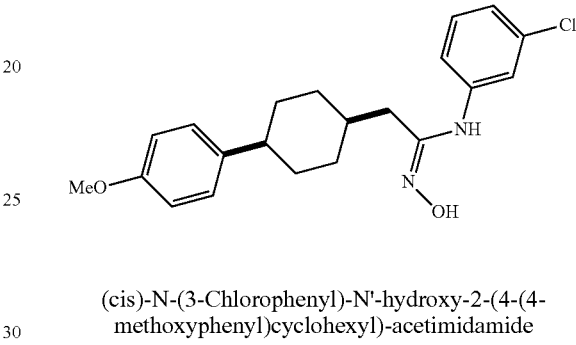

(cis)-N-(3-Chlorophenyl)-N'-hydroxy-2-(4-(4-methoxyphenyl)cyclohexyl)-acetimidamide General Procedures G, H, K, L, and M were used, employing (cis)-methyl 2-(4-(4-methoxyphenyl)cyclohexyl) acetate in General Procedure G. 3-Chloroaniline (0.32 mL) was used in General Procedure H. The final product was purified using silica chromatography (0 to 100% EtOAc in hexanes) to afford the desired product as a white foam. ¹H-NMR (400 MHz; CDCl₃): δ 7.28-7.19 (m, 1H), 7.15-7.03 (m, 5H), 6.94 (ddd, J=8.0, 2.1, 0.9 Hz, 1H), 6.83-6.74 (m, 2H), 3.76 (s, 3H), 2.49 (d, J=7.6 Hz, 2H), 2.47-2.38 (m, 1H), 1.90-1.79 (m, 1H), 1.65-1.51 (m, 8H) ppm. m/z 373.2 (M+H)⁺.

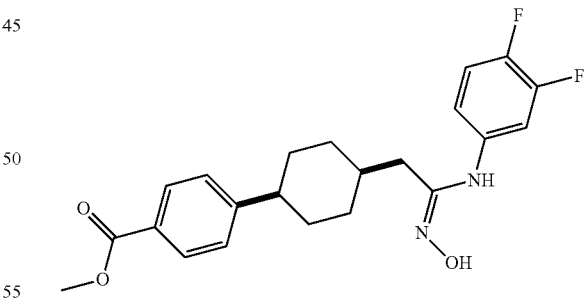

Methyl (cis)-4-(4-(2-((3,4-difluorophenyl)amino)-2-(hydroxyimino)ethyl)-cyclohexyl)benzoate General Procedure J was accomplished with 4-(4-(2-ethoxy-2-oxoethyl)cyclohexyl)benzoic acid (320 mg) and 3,4-difluoroaniline (0.33 mL) to give 4-(4-(2-((3,4-difluorophenyl)amino)-2-oxoethyl)cyclohexyl)benzoic acid. 4-(4-(2-((3,4-Difluorophenyl)amino)-2-oxoethyl)cyclohexyl) benzoic acid was dissolved in methanol (10 mL) and 2 drops of concentrated sulfuric acid. The mixture was heated to reflux for 16 h. The mixture was cooled to rt, basified with careful addition of sodium bicarbonate and extracted with EtOAc (3×25 mL). The combined organic layers were dried over sodium sulfate, and concentrated under reduced pressure. The crude residue was purified by silica chromatography (20 to 25% EtOAc in hexanes) to afford (cis)-methyl 4-(4-(2-((3,4-difluorophenyl)amino)-2-oxoethyl)cyclohexyl)benzoate. Then General Procedures K, L, and M were employed and the final product was purified using silica chromatography (0 to 100% EtOAc in hexanes) to afford the desired product as a white foam. $^1$H-NMR (400 MHz; CDCl$_3$): δ 7.92-7.84 (m, 2H), 7.22 (d, J=8.3 Hz, 2H), 7.10 (dd, J=18.7, 8.8 Hz, 1H), 7.02 (s, 1H), 6.89 (ddd, J=11.1, 6.9, 2.6 Hz, 1H), 6.84-6.71 (m, 1H), 3.93-3.80 (m, 3H), 2.53 (dd, J=14.5, 7.4 Hz, 1H), 2.43 (d, J=7.7 Hz, 2H), 1.87-1.70 (m, 1H), 1.57 (dt, J=16.9, 9.7 Hz, 8H) ppm. m/z 403.2 (M+H)$^+$.

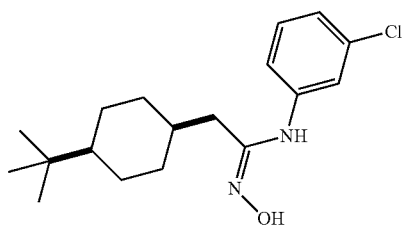

(cis)-2-(4-(tert-Butyl)cyclohexyl)-N-(3-chlorophenyl)-N'-hydroxyacetimidamide

General Procedures D, E, G, I, K, L, and M employing 4-tert-butylcyclohexanone in Procedure D. 3-Chloroaniline was used in General Procedure I. The final product was purified using silica chromatography (0 to 20% EtOAc in hexanes) to afford the desired product as a white foam. $^1$H-NMR (400 MHz; CDCl$_3$): δ 7.23 (t, J=8.0 Hz, 1H), 7.12-7.04 (m, 2H), 6.94 (ddd, J=8.0, 2.1, 0.9 Hz, 1H), 2.42 (d, J=7.6 Hz, 2H), 1.87-1.72 (m, 1H), 1.57 (d, J=12.8 Hz, 2H), 1.44 (d, J=12.8 Hz, 2H), 1.41-1.28 (m, 2H), 1.07-0.81 (m, 3H), 0.78 (s, 9H) ppm. m/z 323.2 (M+H)$^+$.

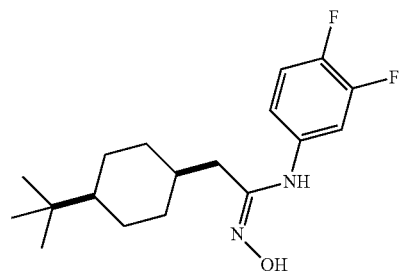

(cis)-2-(4-(tert-Butyl)cyclohexyl)-N-(3,4-difluorophenyl)-N'-hydroxyacetimidamide General Procedures D, E, G, I, K, L, and M employing 4-tert-butylcyclohexanone in Procedure D. 3,4-Difluoroaniline was used in General Procedure I. The final product was purified using silica chromatography (0 to 20% EtOAc in hexanes) to afford the desired product as a white foam. $^1$H-NMR (400 MHz; CDCl$_3$): δ 7.18-7.00 (m, 2H), 6.96-6.84 (m, 1H), 6.84-6.74 (m, 1H), 2.35 (d, J=7.7 Hz, 2H), 1.79-1.72 (m, 1H), 1.54 (d, J=12.4 Hz, 2H), 1.44 (d, J=12.8 Hz, 2H), 1.40-1.28 (m, 2H), 1.07-0.82 (m, 3H), 0.79 (s, 9H) ppm. m/z 325.3 (M+H)$^+$.

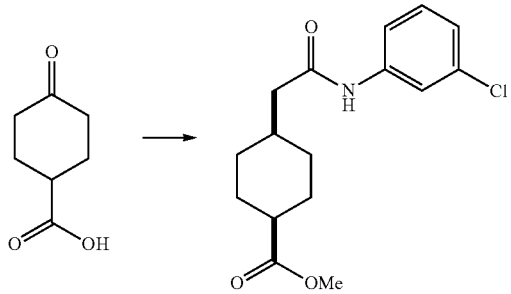 [SMILES: O=C1CCC(C(=O)O)CC1 ; COC(=O)[C@H]1CC[C@@H](CC(=O)Nc2cccc(Cl)c2)CC1]

(cis)-Methyl 4-(2-((3-chlorophenyl)amino)-2-oxoethyl)cyclohexane-1-carboxylate

General Procedures D, E, and J were used, employing 4-oxocyclohexanecarboxylic acid in General Procedures D. General Procedure E employing platinum oxide as catalyst and stirring of the mixture for 3 days at rt. 3-Chloroaniline was used in General Procedure J to give to prepare 4-(2-((3-chlorophenyl)amino)-2-oxoethyl)cyclohexane-1-carboxylic acid. To 4-(2-((3-chlorophenyl)amino)-2-oxoethyl)cyclohexane-1-carboxylic acid (1.23 g, 4.16 mmol) was added methanol (25 mL) and 5 drops of concentrated sulfuric acid. The mixture was heated at reflux for 16 h. The mixture was then cooled to rt and the pH adjusted to 8 with aqueous sodium bicarbonate. This mixture was extracted with EtOAc (3×25 mL) and the combined organic layers were washed with brine (25 mL), dried over anhydrous Na$_2$SO$_4$ and concentration under reduced pressure. The residue was purified using silica gel chromatography (10 to 25% EtOAc in hexanes) to afford (cis)-methyl 4-(2-((3-chlorophenyl)amino)-2-oxoethyl)cyclohexane-1-carboxylate.

(cis)-N-(3-Chlorophenyl)-2-(4-(2-hydroxypropan-2-yl)cyclohexyl)ethanethioamide General Procedure K was used employing (cis)-methyl 4-(2-((3-chlorophenyl)amino)-2-oxoethyl)cyclohexane-1-carboxylate to give (cis)-methyl 4-(2-((3-chlorophenyl)amino)-2-thioxoethyl)cyclohexane-1-carboxylate. (Cis)-methyl 4-(2-((3-chlorophenyl)amino)-2-thioxoethyl)cyclohexane-1-carboxylate (110 mg, 0.34 mmol) was dissolved in THF (2 mL) and cooled to 0° C. then methylmagnesium bromide (2.5M in THF, 0.54 mL, 1.35 mmol) was added. The mixture was stirred at rt for 1 h then saturated aqueous ammonium chloride was added. The mixture was extracted with EtOAc (3×10 mL) and the combined organic layers were washed with brine (25 mL), dried over anhydrous $Na_2SO_4$, and concentration under reduced pressure. The residue was purified using silica gel chromatography (10 to 25% EtOAc in hexanes) to afford (cis)-N-(3-chlorophenyl)-2-(4-(2-hydroxypropan-2-yl)cyclohexyl)ethanethioamide.

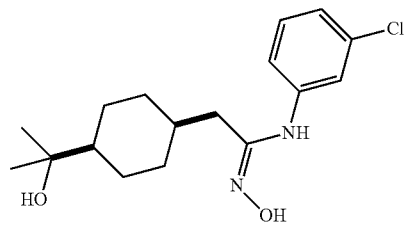

(cis)-N-(3-Chlorophenyl)-N'-hydroxy-2-(4-(2-hydroxypropan-2-yl)cyclohexyl)-acetimidamide General Procedures L and M were used to prepare the title compound from (cis)-N-(3-chlorophenyl)-2-(4-(2-hydroxypropan-2-yl)cyclohexyl)ethanethioamide. The final product was purified using silica chromatography (30 to 100% EtOAc in hexanes) to afford the desired product as a white solid. $^1$H-NMR (400 MHz; CDCl$_3$): δ 7.23 (t, J=8.0 Hz, 1H), 7.15-7.02 (m, 2H), 6.98-6.91 (m, 1H), 2.43 (d, J=7.8 Hz, 2H), 1.82-1.73 (m, 1H), 1.64-1.47 (m, 4H), 1.41-1.34 (m, 2H), 1.23-1.01 (m, 9H) ppm. m/z 325.2 (M+H)$^+$.

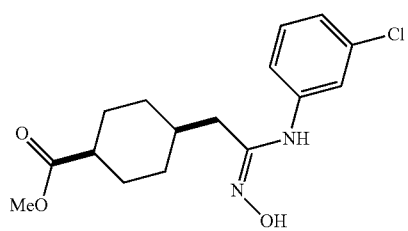

(cis)-Methyl-4-(2-((3-chlorophenyl)amino)-2-(hydroxyimino)ethyl)cyclohexane-1-carboxylate General Procedures K, L, and M were used to prepare the title compound from (cis)-methyl 4-(2-((3-chlorophenyl)amino)-2-oxoethyl)cyclohexane-1-carboxylate. The final product was purified using silica chromatography (0 to 30% EtOAc in hexanes) to afford the desired product as a white solid. $^1$H-NMR (400 MHz; CDCl$_3$): δ 7.23 (t, J=8.0 Hz, 1H), 7.15 (s, 1H), 7.10 (ddd, J=8.0, 1.9, 0.9 Hz, 1H), 7.07 (t, J=2.0 Hz, 1H), 6.94 (ddd, J=8.0, 2.1, 1.0 Hz, 1H), 3.63 (s, 3H), 2.51-2.39 (m, 1H), 2.30 (d, J=6.9 Hz, 2H), 1.99-1.84 (m, 2H), 1.61-1.39 (m, 5H), 1.26-1.15 (m, 2H) ppm.

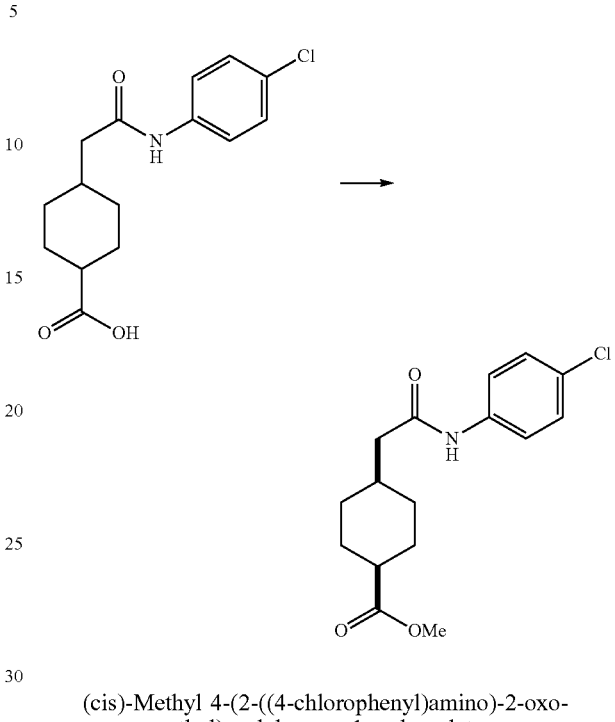

(cis)-Methyl 4-(2-((4-chlorophenyl)amino)-2-oxoethyl)cyclohexane-1-carboxylate General Procedures D, E, and J were used, employing 4-Oxocyclohexanecarboxylic acid in Procedure D. General Procedure E employing platinum oxide as catalyst and stirring the mixture at rt for 3 days. General Procedure J using 4-chloroaniline to give 4-(2-((4-chlorophenyl)amino)-2-oxoethyl)cyclohexane-1-carboxylic acid. To 4-(2-((4-chlorophenyl)amino)-2-oxoethyl)cyclohexane-1-carboxylic acid (1.4 g, 4.16 mmol) in dichloromethane (25 mL) and methanol (25 mL) was added (trimethylsilyl)diazomethane solution (2.0M in diethyl ether, 4.73 mL) dropwise. The mixture was then stirred for 15 min at rt and then silica gel was added. The mixture was concentrated under reduced pressure and purified by silica chromatography (15 to 40% EtOAc in hexanes) to yield (cis)-methyl 4-(2-((4-chlorophenyl)amino)-2-oxoethyl)cyclohexane-1-carboxylate as a white solid.

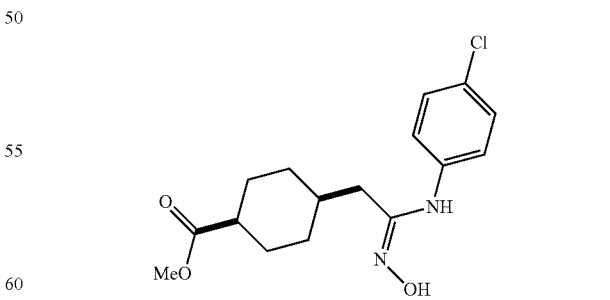

(cis)-Methyl-4-(2-((4-chlorophenyl)amino)-2-(hydroxyimino)ethyl)cyclohexane-1-carboxylate General Procedures K, L, and M were used to prepare the title compound from (cis)-methyl 4-(2-((4-chlorophenyl)

amino)-2-oxoethyl)cyclohexane-1-carboxylate. The final product was purified using silica chromatography (0 to 30% EtOAc in hexanes) to afford the desired product as a white solid. ¹H-NMR (400 MHz; CDCl₃): δ 7.32-7.22 (m, 2H), 7.08 (s, 1H), 7.03-6.94 (m, 2H), 3.62 (s, 3H), 2.50-2.39 (m, 1H), 2.25 (d, J=6.8 Hz, 2H), 1.98-1.82 (m, 2H), 1.55-1.38 (m, 5H), 1.25-1.11 (m, 2H) ppm.

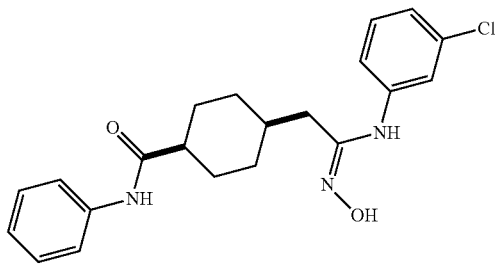

4-((cis)-2-((3-Chlorophenyl)amino)-2-(hydroxy-imino)ethyl)-N-phenylcyclohexane-1-carboxamide General Procedure J was performed using (cis)-methyl 4-(2-((3-chlorophenyl)amino)-2-thioxoethyl)cyclohexane-1-carboxylate (110 mg) and aniline (0.12 mL) to afford (cis)-4-(2-(3-chlorophenyl)amino)-2-thioxoethyl)-N-phenylcyclohexane-1-carboxamide which was subsequently subjected to General Procedures L and M. The final product was purified using silica chromatography (10 to 50% EtOAc in hexanes) to afford the desired product as a white solid. ¹H-NMR (400 MHz; CDCl₃): δ 7.46 (d, J=7.8 Hz, 2H), 7.33-7.14 (m, 5H), 7.13-6.98 (m, 3H), 6.93 (ddd, J=8.0, 2.1, 1.0 Hz, 1H), 2.40 (d, J=7.5 Hz, 2H), 2.35-2.30 (m, 1H), 1.93-1.79 (m, 2H), 1.71-1.56 (m, 3H), 1.56-1.41 (m, 4H) ppm. m/z 386.2 (M+H)⁺.

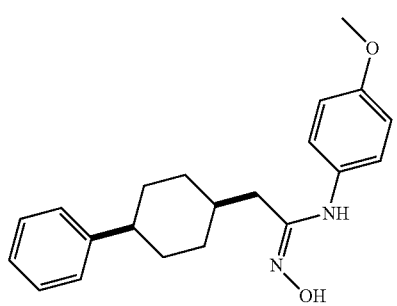

(cis)-N'-Hydroxy-N-(4-methoxyphenyl)-2-(4-phenylcyclohexyl) acetimidamide

Prepared using general Procedures D, E, G, I, K, L, and M. General Procedure E used ethyl 2-(4-phenylcyclohex-ylidene)acetate and Degussa Pd/C (10 wt. %). General Procedure G used ethyl 2-(4-phenylcyclohexyl)acetate. General Procedure I used 2-(4-phenylcyclohexyl)acetic acid and 4-methoxyaniline (2 eq.). General Procedure K used N-(4-methoxyphenyl)-2-(4-phenylcyclohexyl)acetamide. The desired (cis)-isomer was isolated as a first eluting isomer using chromatography on silica gel (0 to 30% EtOAc in hexanes). Mixture of E and Z isomers was observed when NMR was taken in DMSO-d₆. ¹H NMR (400 MHz, DMSO-d₆): δ 9.39 (s, 0.7H), 8.92 (s, 0.3H), 7.65 (s, 0.3H), 7.52 (s, 0.7H), 7.38-7.25 (m, 0.7H), 7.19-7.30 (m, 2.7H), 7.08-7.17 (m, 2.3H), 6.97-7.03 (m, 1.3H), 6.81-6.87 (m, 1.3H), 6.71-6.77 (m, 0.7H), 3.70 (s, 2H), 3.65 (s, 1H), 2.47-2.53 (m, 1.3H), 2.33-2.44 (m, 0.7H), 2.31 (d, J=7.7 Hz, 1.3H) 2.20-2.30 (m, 0.3H), 1.74-1.88 (m, 0.7H), 1.63-1.74 (m, 0.7H), 1.49-1.62 (m, 2H), 1.33-1.50 (m, 5H) ppm. m/z 339.3 (M+H)⁺.

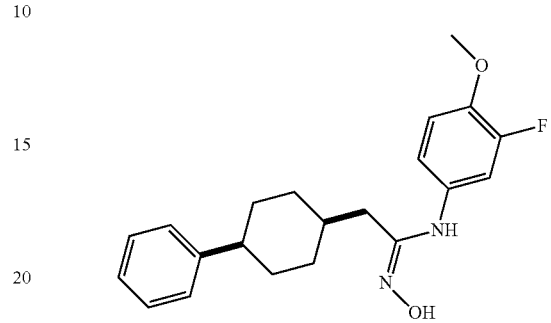

(cis)-N-(3-fluoro-4-methoxyphenyl)-N'-hydroxy-2-(4-phenylcyclohexyl)-acetimidamide Prepared using general Procedures D, E, G, I, K, L, and M. General Procedure E used ethyl 2-(4-phenylcyclohex-ylidene)acetate and Degussa Pd/C (10 wt. %). General Procedure G used ethyl 2-(4-phenylcyclohexyl)acetate. General Procedure I used 2-(4-phenylcyclohexyl)acetic acid and 3-fluoro4-methoxyaniline (2 eq.). General Procedure K used N-(3-fluoro-4-methoxyphenyl)-2-(4-phenylcyclo-hexyl)acetamide. The desired (cis)-isomer was isolated as a first eluting isomer using chromatography on silica gel (0 to 30% EtOAc in hexanes). m/z 357.3 (M+H)⁺.

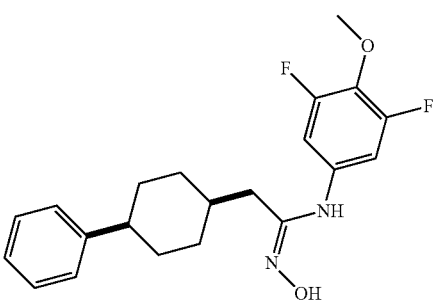

(cis)-N-(3,5-difluoro-4-methoxyphenyl)-N'-hydroxy-2-(4-phenylcyclohexyl)-acetimidamide Prepared using general Procedures D, E, G, I, K, L, and M. General Procedure E used ethyl 2-(4-phenylcyclohex-ylidene)acetate and Degussa Pd/C (10 wt. %). General Procedure G used ethyl 2-(4-phenylcyclohexyl)acetate. General Procedure I used 2-(4-phenylcyclohexyl)acetic acid and 3,5-difluoro-4-methoxyaniline (2 eq.). General Procedure K used N-(3,5-difluoro-4-methoxyphenyl)-2-(4-phe-nylcyclohexyl)acetamide. The desired (cis)-isomer was iso-lated as a first eluting isomer using chromatography on silica gel (0 to 30% EtOAc in hexanes). m/z 375.3 (M+H)⁺.

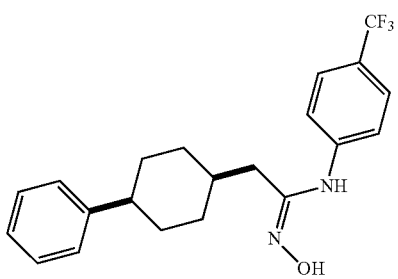

(cis)-N-(4-trifluoromethylphenyl)-N'-hydroxy-2-(4-phenylcyclohexyl)-acetimidamide Prepared using general Procedures D, E, G, I, K, L, and M. General Procedure E used ethyl 2-(4-phenylcyclohexylidene)acetate and Degussa Pd/C (10 wt. %). General Procedure G used ethyl 2-(4-phenylcyclohexyl)acetate. General Procedure I used 2-(4-phenylcyclohexyl)acetic acid and 4-trifluoromethylaniline (2 eq.). General Procedure K used N-(4-trifluoromethylphenyl)-2-(4-phenylcyclohexyl)acetamide. The desired (cis)-isomer was isolated as a first eluting isomer using chromatography on silica gel (0 to 30% EtOAc in hexanes). A mixture of E and Z isomers was observed when NMR was taken in DMSO-$d_6$. $^1$H NMR (400 MHz, DMSO-$d_6$): δ 9.98 (s, 0.25H), 9.44 (s, 0.75H), 8.38 (s, 0.75H), 8.29 (s, 0.25H), 7.64-7.69 (m, 1.6H), 7.46-7.55 (m, 2H), 7.20-7.31 (m, 3.5H), 7.08-7.18 (m, 1.9H), 2.48-2.60 (m, 3H), 2.38-2.48 (m, 0.25H), 2.18-2.28 (m, 0.75H), 1.75-1.90 (m, 1.75H), 1.42-1.64 (m, 6.25H) ppm. m/z 377.2 (M+H)$^+$.

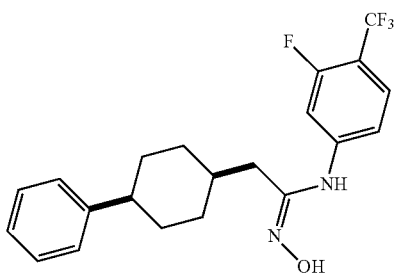

(cis)-N-(3-Fluoro-4-trifluoromethylphenyl)-N'-hydroxy-2-(4-phenylcyclohexyl)acetimidamide Prepared using general Procedures D, E, G, I, K, L, and M. General Procedure E used ethyl 2-(4-phenylcyclohexylidene)acetate and Degussa Pd/C (10 wt. %). General Procedure G used ethyl 2-(4-phenylcyclohexyl)acetate. General Procedure I used 2-(4-phenylcyclohexyl)acetic acid and 4-3-fluoro-4-trifluoromethylaniline (2 eq.). General Procedure K used N-(3-fluoro-4-trifluoromethylphenyl)-2-(4-phenylcyclohexyl)acetamide. The (cis)-isomer was isolated as a first eluting isomer using chromatography on silica gel (0 to 30% EtOAc in hexanes). A mixture of E and Z isomers was observed when NMR was taken in DMSO-$d_6$. $^1$H NMR (400 MHz, DMSO-$d_6$): 10.22 (s, 0.15H), 9.65 (s, 0.85H), 8.68 (s, 0.85H), 8.54 (s, 0.15H), 7.74-7.82 (m, 0.85H), 7.47-7.55 (m, 1H), 7.21-7.30 (m, 4.85H), 7.10-7.18 (m, 1.15H), 6.84-6.92 (m, 0.15H), 2.48-2.60 (m, 3H), 2.38-2.48 (m, 0.15H), 2.16-2.26 (m, 0.85H), 1.74-1.88 (m, 1.85H), 1.46-1.64 (m, 6.15H) ppm. m/z 395.2 (M+H)$^+$.

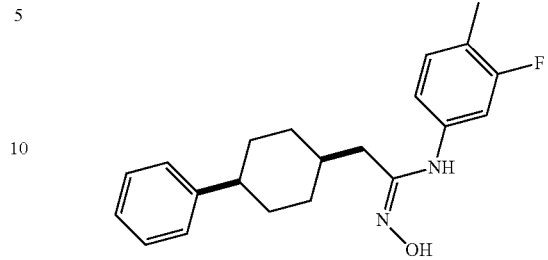

(cis)-N-(3-Fluoro-4-methylphenyl)-N'-hydroxy-2-(4-phenylcyclohexyl)-acetimidamide Prepared using general Procedures D, E, G, I, K, L, and M. General Procedure E used ethyl 2-(4-phenylcyclohexylidene)acetate and Degussa Pd/C (10 wt. %). General Procedure G used ethyl 2-(4-phenylcyclohexyl)acetate. General Procedure I used 2-(4-phenylcyclohexyl)acetic acid and 3-fluoro4-methylaniline (2 eq.). General Procedure K used N-(3-fluoro4-methylphenyl)-2-(4-phenylcyclohexyl)acetamide. The (cis)-isomer was isolated as a first eluting isomer using chromatography on silica gel (0 to 30% EtOAc in hexanes). A mixture of E and Z isomers was observed when NMR was taken in DMSO-$d_6$. $^1$H NMR (400 MHz, DMSO-$d_6$): 9.67 (s, 0.35H), 9.21 (m, 0.65H), 8.02 (s, 0.65H), 7.87 (s, 0.35H), 7.51-7.57 (m, 0.65H), 7.20-7.30 (m, 3.35H), 7.08-7.17 (m, 2H), 7.07-7.05 (m, 1.35H), 7.76-7.86 (m, 0.65H), 2.48-2.55 (m, 1.85H), 2.35-2.48 (m, 1.25H), 2.17-2.27 (m, 0.65H), 2.12-2.15 (m, 1H), 2.07-2.10 (m, 2H), 1.67-1.87 (m, 1.75H), 1.40-1.60 (m, 6.5H) ppm. m/z 341.2 (M+H)$^+$.

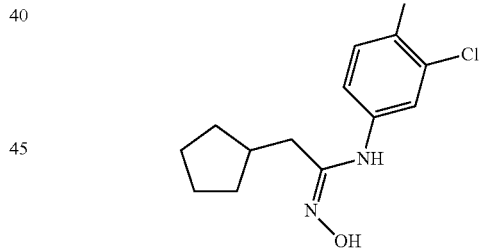

N-(3-Chloro-4-fluorophenyl)-2-cyclopentyl-N'-hydroxyacetimidamide

Prepared using General Procedure N employing 143 mg (2-nitroethyl)cyclopentane, 582 mg, 3-chloro-4-fluoroaniline, and 4.0 mmol BuLi in 5.0 mL of THF. Purified using silica gel chromatography (0 to 5% MeOH in CH$_2$Cl$_2$) to afford the desired product as an oil. m/z 271.1 (M+H$^+$).

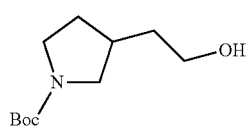 [SMILES: CC(C)(C)OC(=O)N1CCC(CCO)C1]

tert-Butyl 3-(2-hydroxyethyl)pyrrolidine-1-carboxylate

To a solution of 2-(1-(tert-butoxycarbonyl)pyrrolidin-3-yl)acetic acid (2.29 g, 10 mmol) at −78° C. was added a solution of BH$_3$.SMe$_2$ (12 mL, 12.0 mmol 1 M in THF). The mixture was allowed to warm to rt and was stirred 4 h. The mixture was cooled to 0° C. 1M NaOH solution (20 mL) was added followed by EtOAc (30 mL). The layers were separated, and the aqueous layer was extracted with EtOAc (3×25 mL). The combined organic layers were dried over anhydrous MgSO$_4$, filtered, and concentrated under reduced pressure. The residue was purified employing silica gel chromatography (40 to 100% EtOAc in hexanes) to afford the desired product as an oil, 596 g, 67%.

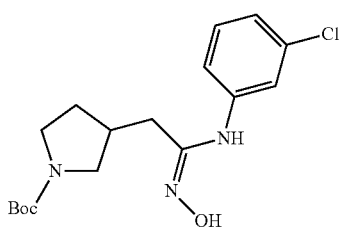 [SMILES: CC(C)(C)OC(=O)N1CCC(C/C(=N/O)Nc2cccc(Cl)c2)C1]

tert-Butyl 3-(2-((3-chlorophenyl)amino)-2-(hydroxyimino)ethyl)pyrrolidine-1-carboxylate Prepared using General Procedure N employing 855 mg tert-butyl 3-(2-nitroethyl)pyrrolidine-1-carboxylate, 1.79 g, 3-chloroaniline, and 14.0 mmol BuLi in 18.0 mL of THF. Purified using silica gel chromatography (20 to 70% EtOAc in hexanes) to afford the desired product as an oil (1.06 g, 85% yield). $^1$H-NMR (400 MHz; CDCl$_3$): δ 7.33 (s, 1H), 7.28-7.24 (m, 1H), 7.14 (dd, J=7.8, 0.2 Hz, 1H), 7.08 (t, J=1.9 Hz, 1H), 6.97-6.95 (m, 1H), 3.48-3.30 (m, 2H), 3.23-3.17 (m, 1H), 2.97-2.83 (m, 1H), 2.48-2.40 (m, 2H), 2.28-2.21 (m, 1H), 1.95-1.90 (m, 1H), 1.54-1.46 (m, 1H), 1.40 (s, 9H) ppm. m/z 298.1 (M+H$^+$).

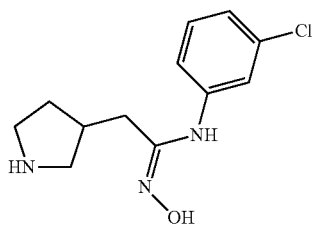 [SMILES: O/N=C(/CC1CCNC1)Nc1cccc(Cl)c1]

N-(3-Chlorophenyl)-N'-hydroxy-2-(pyrrolidin-3-yl)acetimidamide

To a solution of tert-butyl (Z)-3-(2-((3-chlorophenyl)amino)-2-(hydroxyimino)ethyl)pyrrolidine-1-carboxylate (35 mg, 0.1 mmol) in CH$_2$Cl$_2$ (500 µL) at 0° C. was added TFA (114 mg, 1.0 mmol). The mixture was warmed to rt and was stirred for 4 h. The mixture was concentrated under reduced pressure and the residue was purified using silica gel chromatography (0 to 25% MeOH in CH$_2$Cl$_2$) to afford the desired product as an oil. $^1$H-NMR (400 MHz; CDCl$_3$): δ 9.73 (s, 1H), 9.40 (s, 1H), 7.29 (t, J=8.0 Hz, 1H), 7.20-7.18 (m, 1H), 7.08 (t, J=1.9 Hz, 1H), 6.97 (dd, J=7.9, 1.0 Hz, 1H), 3.46-3.37 (m, 2H), 3.17-3.13 (m, 2H), 2.65 (dd, J=15.0, 4.0 Hz, 1H), 2.54-2.48 (m, 1H), 2.48-2.39 (m, 1H), 2.15-2.06 (m, 1H), 1.79-1.69 (m, 1H) ppm. m/z 239.1 (M+H$^+$).

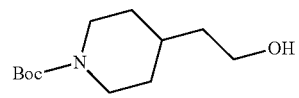

tert-Butyl 4-(2-hydroxyethyl)piperidine-1-carboxylate

To a solution of 2-(piperidin-4-yl)ethan-1-ol (5.0 g, 38.7 mmol) in THF (100 mL) at rt, was added Boc$_2$O (8.45 g, 38.7 mmol). The mixture was stirred at rt for 16 h and then concentrated under reduced pressure. The residue was purified using silica gel chromatography (40 to 80% EtOAc in hexanes) to afford the desired product as an oil.

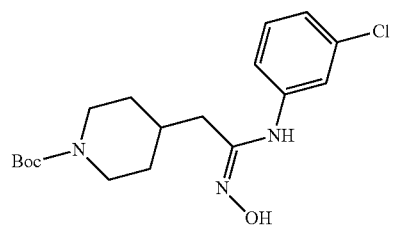 [SMILES: CC(C)(C)OC(=O)N1CCC(C/C(=N/O)Nc2cccc(Cl)c2)CC1]

tert-Butyl-4-(2-((3-chlorophenyl)amino)-2-(hydroxyimino)ethyl)piperidine-1-carboxylate Prepared using General Procedure N employing 129 mg tert-butyl 4-(2-nitroethyl)piperidine-1-carboxylate, 255 mg, 3-chloroaniline, and 2.0 mmol BuLi in 2.5 mL of THF. Purified using silica gel chromatography (20 to 70% EtOAc in hexanes) to afford the desired product as an oil (132 mg, 72% yield). $^1$H-NMR (400 MHz; CDCl$_3$): δ 7.25 (t, J=8.0 Hz, 1H), 7.13 (ddd, J=8.0, 2.0, 0.9 Hz, 1H), 7.09-7.05 (m, 2H), 6.93 (ddd, J=8.0, 2.1, 1.0 Hz, 1H), 4.02 (s, 2H), 2.64-2.55 (m, 2H), 2.27 (d, J=6.8 Hz, 2H), 1.66-1.53 (m, 4H), 1.42 (s, 9H), 1.11-1.00 (m, 2H) ppm.

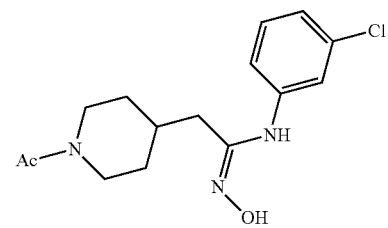

2-(1-Acetylpiperidin-4-yl)-N-(3-chlorophenyl)-N'-hydroxyacetimidamide

Prepared using General Procedure N employing 100 mg 1-(4-(2-nitroethyl)piperidin-1-yl)ethan-1-one, 255 mg, 3-chloroaniline, and 2.0 mmol BuLi in 2.5 mL of THF. Purified using silica gel chromatography (0 to 25% MeOH in CH$_2$Cl$_2$) to afford the desired product as an orange foam.

¹H-NMR (400 MHz; CDCl₃): δ 7.22 (t, J=8.0 Hz, 1H), 7.09 (dd, J=8.0, 0.9 Hz, 1H), 7.02 (s, 1H), 6.91-6.89 (m, 1H), 4.50-4.46 (m, 1H), 3.70-3.67 (m, 1H), 2.92-2.85 (m, 1H), 2.44-2.38 (m, 1H), 2.29-2.24 (m, 2H), 2.01 (s, 3H), 1.69-1.58 (m, 3H), 1.10-0.99 (m, 2H) ppm. m/z 310.1 (M+H⁺).

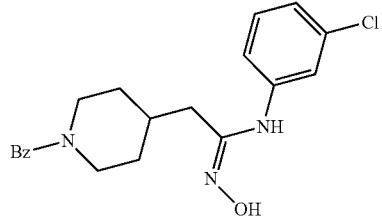

2-(1-Benzoylpiperidin-4-yl)-N-(3-chlorophenyl)-N'-hydroxyacetimidamide

Prepared using General Procedure N employing 235 mg 1-(4-(2-nitroethyl)piperidin-1-yl)ethan-1-one, 459 mg, 3-chloroaniline, and 3.6 mmol BuLi in 4.5 mL of THF. Purified using silica gel chromatography (50 to 100% EtOAc in hexanes) to afford the desired product as a foam (151 mg, 45% yield). ¹H-NMR (400 MHz; CDCl₃): δ 7.36-7.30 (m, 5H), 7.22 (t, J=8.0 Hz, 1H), 7.10-7.08 (m, 1H), 7.02 (t, J=2.0 Hz, 1H), 6.91-6.89 (m, 1H), 4.61-4.58 (m, 1H), 3.66-3.61 (m, 1H), 2.89-2.60 (m, 2H), 2.37-2.26 (m, 2H), 1.75-1.54 (m, 3H), 1.19-1.02 (m, 2H) ppm. m/z 372.2 (M+H⁺).

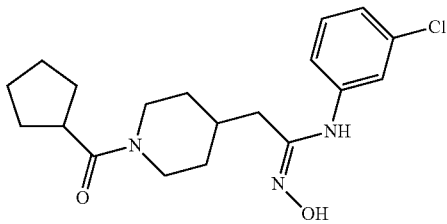 [SMILES: O=C(C1CCCC1)N1CCC(C/C(=N/O)Nc2cccc(Cl)c2)CC1]

N-(3-Chlorophenyl)-2-(1-(cyclopentanecarbonyl) piperidin-4-yl)-N'-hydroxyacetimidamide Prepared using General Procedure N employing 36 mg cyclopentyl(4-(2-nitroethyl)piperidin-1-yl)methanone, 71 mg, 3-chloroaniline, and 0.56 mmol BuLi in 0.7 mL of THF. Purified using silica gel chromatography (50 to 100% EtOAc in hexanes) to afford the desired product as a brown foam (39 mg, 45% yield). ¹H-NMR (400 MHz; CDCl₃): δ 7.24 (t, J=8.0 Hz, 1H), 7.12-7.10 (m, 1H), 7.04 (t, J=2.0 Hz, 1H), 6.92 (dt, J=8.0, 1.0 Hz, 1H), 4.55-4.52 (m, 1H), 3.89-3.86 (m, 1H), 2.91-2.78 (m, 2H), 2.48-2.41 (m, 1H), 2.28 (dd, J=6.7, 2.7 Hz, 2H), 1.79-1.60 (m, 8H), 1.56-1.49 (m, 3H), 1.07-1.01 (m, 2H) ppm. m/z 364.2 (M+H⁺).

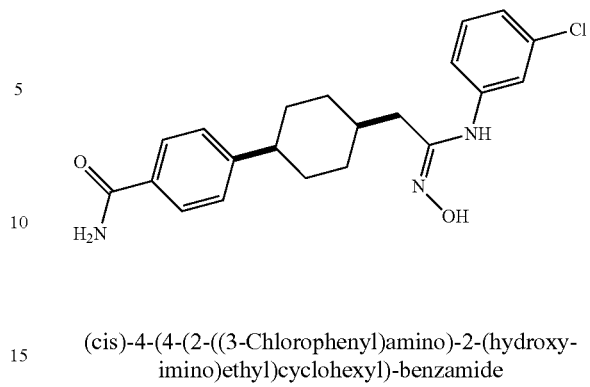

(cis)-4-(4-(2-((3-Chlorophenyl)amino)-2-(hydroxyimino)ethyl)cyclohexyl)-benzamide Prepared using General Procedures D, F, G, H, K, L, and M. 4-(4-Oxocyclohexyl)benzonitrile was employed in General Procedure D. General Procedure H used 3-chloroaniline. General Procedure M used methyl (cis)-N-(3-chlorophenyl)-2-(4-(4-cyanophenyl)cyclohexyl)ethanimidothioate (35 mg) hydroxylamine solution (61 μL), EtOH (500 mL). Purified using silica gel chromatography (0 to 5% MeOH in CH₂Cl₂) to afford the desired product as an oil. ¹H-NMR (400 MHz; CDCl₃): δ 7.70 (d, J=8.3 Hz, 1H), 7.50 (d, J=8.3 Hz, 2H), 7.23 (d, J=1.4 Hz, 2H), 7.19 (d, J=8.3 Hz, 1H), 7.12 (ddd, J=8.0, 2.0, 0.9 Hz, 1H), 7.09 (q, J=1.9 Hz, 1H), 6.97-6.94 (m, 1H), 4.88-4.81 (br s, 2H), 2.50 (d, J=7.7 Hz, 2H), 1.86-1.81 (m, 1H), 1.62-1.56 (m, 11H) ppm. m/z 386.2 (M+H⁺).

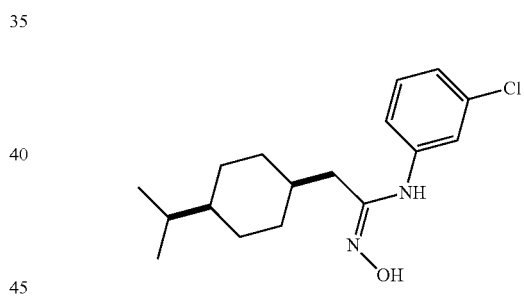

(cis)-N-(3-Chlorophenyl)-N'-hydroxy-2-(4-isopropylcyclohexyl)acetimidamide

Prepared using General Procedures D, F, J, K, L, and M. 4-Isopropylcyclohexan-1-one was employed in General Procedure D. 3-Chloroaniline was used in General Procedure J. General Procedure M used methyl (cis)-N-(3-chlorophenyl)-2-(4-isopropylcyclohexyl)ethanimidothioate (110 mg), hydroxylamine solution (227 μL) and EtOH (3.0 mL). Purified using silica gel chromatography (5 to 20% EtOAc in hexanes) to afford the desired product as an oil. ¹H-NMR (400 MHz; CDCl₃): δ 7.23 (t, J=8.0 Hz, 1H), 7.10-7.08 (m, 1H), 7.05 (q, J=2.0 Hz, 1H), 6.94 (dt, J=8.0, 1.0 Hz, 1H), 2.39 (d, J=7.5 Hz, 2H), 1.71-1.63 (m, 1H), 1.46-1.20 (m, 9H), 1.03-0.94 (m, 1H), 0.88-0.85 (m, 1H), 0.80 (d, J=6.7 Hz, 6H) ppm. m/z 309.2 (M+H⁺).

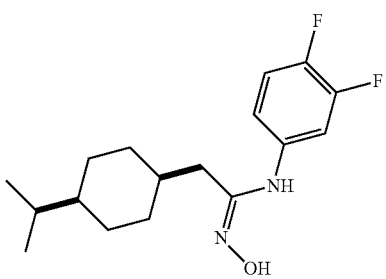 [SMILES: CC(C)[C@H]1CC[C@@H](C/C(=N/O)Nc2ccc(F)c(F)c2)CC1]

(cis)-N-(3,4-Difluorophenyl)-N'-hydroxy-2-(4-isopropylcyclohexy)acetimidamide

Prepared using General Procedures D, F, J, K, L, and M. 4-Isopropylcyclohexan-1-one was employed in General Procedure D. 3,4-Difluoroaniline was used in General Procedure J. General Procedure M use methyl (cis)-N-(3,4-difluorophenyl)-2-(4-isopropylcyclohexyl)ethanimidothioate (111 mg), hydroxylamine solution 227 µL, and EtOH (3.0 mL). Purified using silica gel chromatography (0 to 10% EtOAc in hexanes) to afford the desired product as an oil. $^1$H-NMR (400 MHz; CDCl$_3$): δ 7.11 (dt, J=10.0, 8.8 Hz, 1H), 7.00 (s, 1H), 6.91 (ddd, J=11.3, 6.9, 2.6 Hz, 1H), 6.80 (dddd, J=8.8, 3.9, 2.5, 1.5 Hz, 1H), 2.29 (d, J=7.5 Hz, 2H), 1.65-1.62 (m, 1H), 1.48-1.39 (m, 1H), 1.40-1.31 (m, 5H), 1.27-1.17 (m, 2H), 1.02-0.96 (m, 1H), 0.80 (d, J=6.7 Hz, 6H) ppm. m/z 311.3 (M+H$^+$).

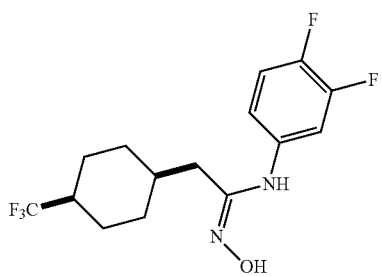

(cis)-N-(3,4-Difluorophenyl)-N'-hydroxy-2-(4-(trifluoromethyl)cyclohexyl)-acetimidamide Prepared using General Procedures D, F, J, K, L, and M. 4-Trifluoromethylcyclohexan-1-one was employed General Procedure D. 3,4-Difluoroaniline was used in General Procedure J. General Procedure M used methyl (cis)-N-(3,4-difluorophenyl)-2-(4-(trifluoromethyl)cyclohexyl)ethanimidothioate (105 mg), hydroxylamine solution (200 µL) and EtOH (3.0 mL). Purified using silica gel chromatography (0 to 20% EtOAc in hexanes) to afford the desired product as an oil. $^1$H-NMR (400 MHz; CDCl$_3$): δ 7.12 (dt, J=9.9, 8.8 Hz, 1H), 7.06 (s, 1H), 6.91 (ddd, J=11.2, 6.9, 2.7 Hz, 1H), 6.81 (dddd, J=8.8, 3.9, 2.5, 1.5 Hz, 1H), 2.37-2.31 (m, 2H), 2.03-1.94 (m, 1H), 1.71-1.65 (m, 1H), 1.59 (tq, J=11.5, 4.0 Hz, 3H), 1.53-1.38 (m, 5H) ppm. m/z 337.2 (M+H$^+$).

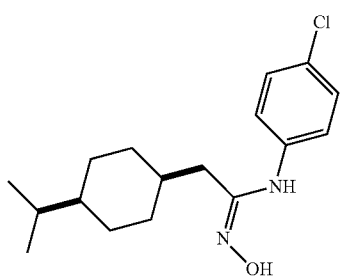 [SMILES: CC(C)[C@H]1CC[C@@H](C/C(=N/O)Nc2ccc(Cl)cc2)CC1]

(cis)-N-(4-Chlorophenyl)-N'-hydroxy-2-(4-isopropylcyclohexyl)acetimidamide

Prepared using General Procedures D, F, J, K, L, and M. 4-Isopropylcyclohexan-1-one was employed in General Procedure D. 4-Chloroaniline was used in General Procedure J. General Procedure M used methyl (cis)-N-(4-chlorophenyl)-2-(4-isopropylcyclohexyl)ethanimidothioate (81 mg), hydroxylamine solution (167 µL), and EtOH (2.0 mL). Purified using silica gel chromatography (0 to 10% EtOAc in hexanes) to afford the desired product as an oil. $^1$H-NMR (400 MHz; CDCl$_3$): δ 7.29-7.26 (m, 2H), 7.09 (br s, 1H), 7.01-6.97 (m, 2H), 2.32 (d, J=7.5 Hz, 2H), 1.67-1.61 (m, 1H), 1.43 (dt, J=13.6, 6.8 Hz, 1H), 1.38-1.30 (m, 6H), 1.26-1.18 (m, 2H), 1.02-0.94 (m, 1H), 0.80 (d, J=6.7 Hz, 6H) ppm. m/z 309.2 (M+H$^+$).

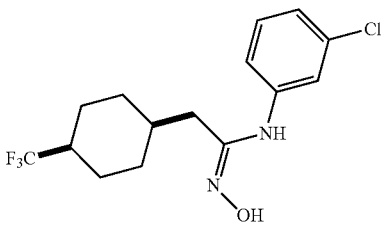 [SMILES: O/N=C(/C[C@H]1CC[C@@H](C(F)(F)F)CC1)Nc1cccc(Cl)c1]

(cis)-N-(3-Chlorophenyl)-N'-hydroxy-2-((1s,4s)-4-(trifluoromethyl)cyclohexyl)-acetimidamide Prepared using General Procedures D, F, J, K, L, and M. 4-Trifluoromethylcyclohexan-1-one was used in General Procedure D. 3-Chloroaniline was used in General Procedure J. General Procedure M used methyl (cis)-N-(3-chlorophenyl)-2-(4-(trifluoromethyl)cyclohexyl)ethanimidothioate (105 mg), hydroxylamine solution (200 µL) and EtOH (3.0 mL). Purified using silica gel chromatography (0 to 20% EtOAc in hexanes) to afford the desired product as an oil. $^1$H-NMR (400 MHz; CDCl$_3$): δ 7.25 (t, J=8.0 Hz, 1H), 7.15 (s, 1H), 7.13-7.11 (m, 1H), 7.06 (t, J=2.1 Hz, 1H), 6.96-6.93 (m, 1H), 2.41 (d, J=7.6 Hz, 2H), 2.03-1.94 (m, 1H), 1.77-1.69 (m, 1H), 1.66-1.57 (m, 2H), 1.56-1.38 (m, 6H) ppm. m/z 335.1 (M+H$^+$).

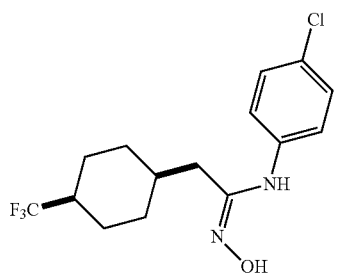 [SMILES: O/N=C(/C[C@H]1CC[C@@H](C(F)(F)F)CC1)Nc1ccc(Cl)cc1]

(cis)-N-(4-Chlorophenyl)-N'-hydroxy-2-(4-(trifluoromethyl)cyclohexyl)-acetimidamide Prepared using General Procedures D, F, J, K, L, and M. 4-Trifluoromethyl-cyclohexan-1-one was employed in General Procedure D. 4-Chloroaniline was used in General Procedure J. General Procedure M used methyl (cis)-N-(4-chlorophenyl)-2-(4-(trifluoromethyl)-cyclohexyl)ethanimidothioate (87 mg), hydroxylamine solution (167 μL), and EtOH (2.0 mL). Purified using silica gel chromatography (0 to 25% EtOAc in hexanes) to afford the desired product as an oil. $^1$H-NMR (400 MHz; CDCl$_3$): δ 7.30-7.26 (m, 2H), 7.01-6.98 (m, 2H), 2.37 (d, J=7.7 Hz, 2H), 2.02-1.93 (m, 1H), 1.71-1.64 (m, 1H), 1.63-1.35 (m, 9H) ppm. m/z 335.1 (M+H$^+$).

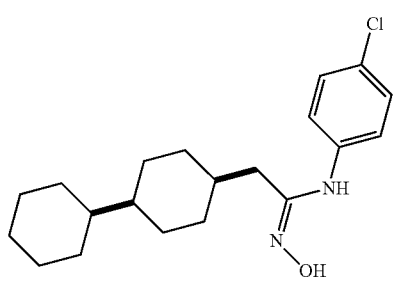

(cis)-2-((1,1'-Bi(cyclohexan))-4-yl)-N-(4-chlorophenyl)-N'-hydroxyacetimidamide

Prepared using General Procedures D, F, J, K, L, and M. (1,1'-Bi(cyclohexan))-4-one was used in General Procedure D. 4-Chloroaniline was employed in General Procedure J. General Procedure M used methyl (cis)-2-((1,1'-bi(cyclohexan))-4-yl)-N-(4-chlorophenyl)ethanimidothioate (84 mg), hydroxylamine solution (80 μL), and EtOH (2.0 mL). Purified using silica gel chromatography (0 to 25% EtOAc in hexanes) to afford the desired product as an oil. $^1$H-NMR (400 MHz; CDCl$_3$): δ 7.29-7.26 (m, 2H), 7.08 (br s, 1H), 7.01-6.98 (m, 2H), 2.31 (d, J=7.5 Hz, 2H), 1.69-1.58 (m, 6H), 1.36-1.01 (m, 13H), 0.87-0.77 (m, 2H) ppm. m/z 349.3 (M+H$^+$).

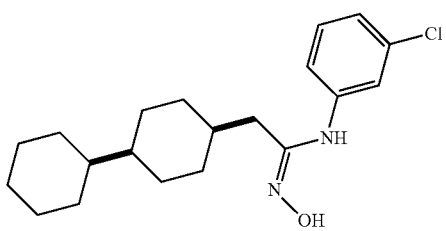

(cis)-2-((1,1'-Bi(cyclohexan))-4-yl)-N-(3-chlorophenyl)-N'-hydroxyacetimidamide

Prepared using General Procedures D, F, J, K, L, and M. (1,1'-Bi(cyclohexan))-4-one was employed in General Procedure D. General Procedure J employed 3-chloroaniline. General Procedure M used methyl (cis)-2-((1,1'-bi(cyclohexan))-4-yl)-N-(3-chlorophenyl)ethanimidothioate (91 mg), hydroxylamine solution (83 μL) and EtOH (2.0 mL). Purified using silica gel chromatography (0 to 25% EtOAc in hexanes) to afford the desired product as an oil. m/z 349.3 (M+H$^+$).

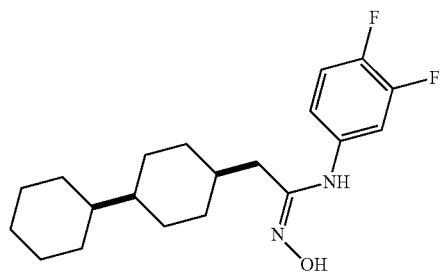

(cis)-2-((1,1'-Bi(cyclohexan))-4-yl)-N-(3,4-difluorophenyl)-N'-hydroxyacetimidamide Prepared using General Procedures D, F, J, K, L, and M. General Procedure D used (1,1'-bi(cyclohexan))-4-one. 3,4-Difluoroaniline was used in General Procedure J. General Procedure M used methyl (cis)-2-((1,1'-bi(cyclohexan))-4-yl)-N-(3,4-difluorophenyl)ethanimidothioate (69 mg), hydroxylamine solution (63 μL) and EtOH (2.0 mL). Purified using silica gel chromatography (0 to 25% EtOAc in hexanes) to afford the desired product as an oil. m/z 351.3 (M+H$^+$).

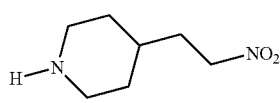

4-(2-Nitroethyl)piperidine

To a solution of tert-butyl 4-(2-nitroethyl)piperidine-1-carboxylate (129 mg, 0.5 mmol) in CH$_2$Cl$_2$ (2.0 mL) at 0° C. was added TFA (570 mg, 5.0 mmol). The mixture was warmed to rt, stirred at rt for 8 h, and concentrated under reduced pressure. The residue was used without further purification.

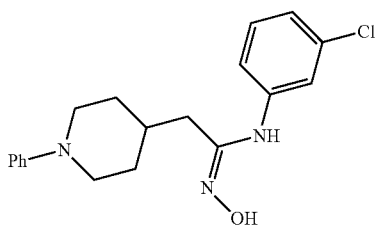 [SMILES: O/N=C(/CC1CCN(c2ccccc2)CC1)Nc1cccc(Cl)c1]

N-(3-Chlorophenyl)-N'-hydroxy-2-(1-phenylpiperidin-4-yl)acetimidamide

Prepared using General Procedure N employing 4-(2-nitroethyl)-1-phenylpiperidine (47 mg), 3-chloroaniline (102 mg), n-BuLi (0.8 mmol) and THF (3 mL). Purified using silica gel chromatography (0 to 5% MeOH in CH$_2$Cl$_2$) to afford the desired product as a yellow foam (50 mg, 73% yield). $^1$H-NMR (400 MHz; CDCl$_3$): δ 7.23 (t, J=8.0 Hz, 3H), 7.13 (ddd, J=8.0, 1.9, 0.9 Hz, 1H), 7.09 (d, J=2.0 Hz, 1H), 6.96 (ddd, J=8.0, 2.1, 0.9 Hz, 1H), 6.91-6.89 (m, 2H), 6.82 (t, J=7.3 Hz, 1H), 3.60 (d, J=12.4 Hz, 2H), 2.60 (td, J=12.1, 2.2 Hz, 2H), 2.37 (d, J=7.0 Hz, 2H), 1.78-1.75 (m, 2H), 1.59-1.52 (m, 1H), 1.36 (qd, J=12.1, 3.6 Hz, 2H) ppm. m/z 172.7 (M+2H).

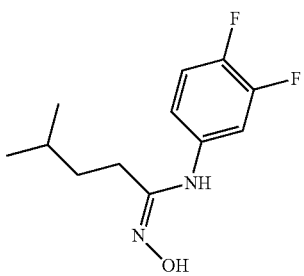 [SMILES: CC(C)CC/C(=N/O)Nc1ccc(F)c(F)c1]

N-(3,4-Difluorophenyl)-N'-hydroxy-4-methylpentanimidamide

Prepared using General Procedure N employing 4-methyl-1-nitropentane (131 mg), 3,4-difluoroaniline (516 mg), n-BuLi (4.0 mmol) and THF (4.0 mL). Purified using silica gel chromatography (0 to 25% EtOAc in hexanes) to afford the desired product as a red oil. $^1$H-NMR (400 MHz; CDCl$_3$): δ 7.11 (dt, J=10.0, 8.8 Hz, 1H), 7.01 (br s, 1H), 6.92 (ddd, J=11.2, 6.9, 2.7 Hz, 1H), 6.83-6.79 (m, 1H), 2.29-2.25 (m, 2H), 1.53-1.43 (m, 1H), 1.31-1.28 (m, 1H), 0.79 (d, J=6.6 Hz, 6H) ppm. m/z 243.2 (M+H$^+$).

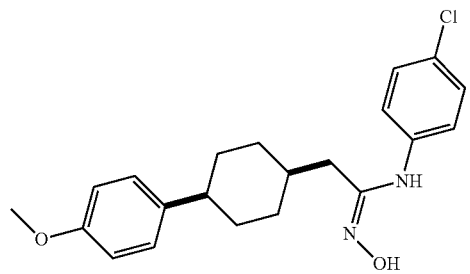

(cis)-N-(4-Chlorophenyl)-N'-hydroxy-2-(4-(4-methoxyphenyl)cyclohexyl)-acetimidamide Prepared from (cis)-methyl 2-((1,4)4-(4-methoxyphenyl) cyclohexyl)acetate by General Procedures G, I, K, L, and M. In General Procedure I, 4-chloroaniline was used. General Procedure M used methyl (cis)-N-(4-chlorophenyl)-2-(4-(4-methoxyphenyl)cyclohexyl)-ethanimidothioate (50 mg), hydroxylamine solution (43 μL) and EtOH (2.0 mL). Purified using silica gel chromatography (0 to 30% EtOAc in hexanes) to afford the desired product as an oil. $^1$H-NMR (400 MHz; CDCl$_3$): δ 7.32-7.28 (m, 2H), 7.07-7.04 (m, 2H), 7.03-7.00 (m, 2H), 6.83-6.80 (m, 2H), 3.77 (s, 3H), 2.44 (d, J=7.7 Hz, 2H), 1.62-1.48 (m, 9H) ppm. m/z 373.2 (M+H$^+$).

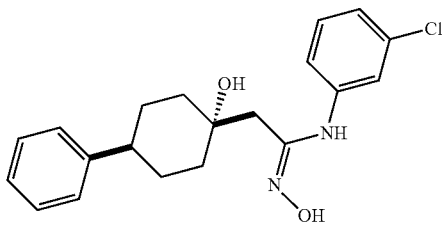

(cis)-N-(3-Chlorophenyl)-N'-hydroxy-2-(1-hydroxy-4-phenylcyclohexyl)-acetimidamide

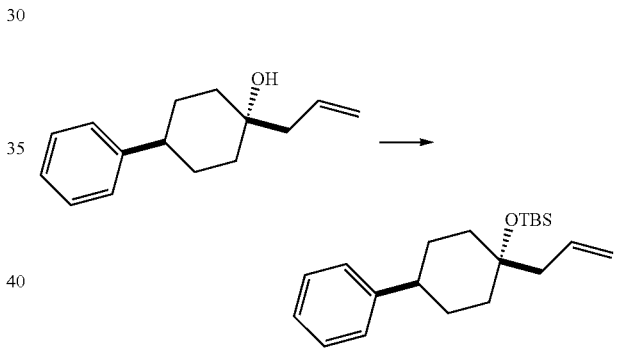

To a solution of cis-1-allyl-4-phenylcyclohexan-1-ol$^i$ (1.30 g, 6.0 mmol) in CH$_2$Cl$_2$ (12 mL) was added 2,6-lutidine (1.61 g, 15.0 mmol) the mixture was cooled to 0° C. and TBSOTf (2.38 g, 9.0 mmol) was added dropwise. The mixture was allowed to warm to rt and was stirred for 6 h. The mixture was cooled to 0° C. and NaHCO$_3$ solution (50 mL) was added. The biphasic mixture was stirred for 10 min, and EtOAc (100 mL) was added. The layers were separated, and the aqueous layer was extracted with EtOAc (3×50 mL). The combined organic layers were dried over anhydrous MgSO$_4$, filtered, and concentrated under reduced pressure. The residue was purified employing silica gel chromatography (0 to 25% EtOAc in hexanes) to afford (((cis)-1-allyl-4-phenylcyclohexyl)oxy)(tert-butyl)dimethylsilane as an oil (1.87 g, 94% yield).

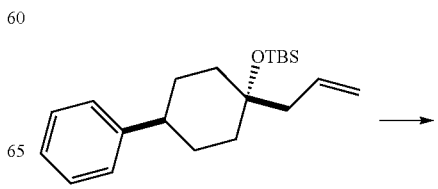

-continued

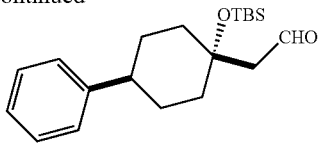

To a solution of (((cis)-1-allyl-4-phenylcyclohexyl)oxy)(tert-butyl)dimethylsilane (331 mg, 1.0 mmol) in dioxane/water (3:1, 5.0 mL) was added 2,6-lutidine (114 mg, 2.0 mmol), NaIO$_4$ (856 mg, 4.0 mmol) and OsO$_4$ solution (100 μL, 4 wt. % in water). The color of the mixture became dark and the mixture was stirred at rt for 16 h. Saturated Na$_2$S$_2$O$_3$ solution (20 mL) was added, and the resulting slurry was stirred at rt for 15 min. EtOAc (50 mL) was added. The layers were separated, and the aqueous layer was extracted with EtOAc (3×25 mL). The combined organic layers were dried over anhydrous MgSO$_4$, filtered, and concentrated under reduced pressure to give 2-((cis)-1-((tert-butyldimethylsilyl)oxy)-4-phenylcyclohexyl)acetaldehyde which was used without further purification.

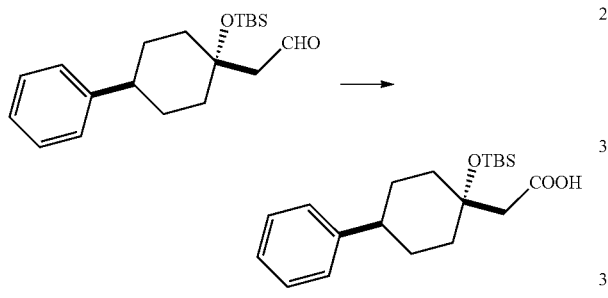

To a solution of 2-((cis)-1-((tert-butyldimethylsilyl)oxy)-4-phenylcyclohexyl)-acetaldehyde (331 mg, 1.0 mmol) in $^t$BuOH (10 mL) was added cyclohexene (1.64 g, 20 mmol), NaH$_2$PO$_4$ (840 mg, 7.0 mmol) and NaClO$_2$ (904 mg, 10 mmol). The mixture was warmed to rt, was stirred 30 min. Then saturated Na$_2$S$_2$O$_3$ solution (20 mL) was added. The resulting slurry was stirred for 15 min, and EtOAc (50 mL) was added. The layers were separated, and the aqueous layer was extracted with EtOAc (3×25 mL). The combined organic layers were dried over anhydrous MgSO$_4$, filtered, and concentrated under reduced pressure to give 2-((cis)-1-((tert-butyldimethylsilyl)oxy)-4-phenylcyclohexyl)acetic acid which was used without further purification.

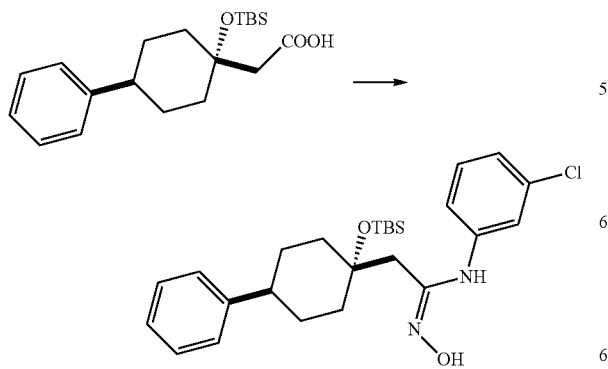

General Procedures I, K, L and M were used. 3-Chloroaniline and 2-((cis)-1-((tert-butyldimethylsilyl)oxy)-4-phenylcyclohexyl)acetic acid were employed in General Procedure I. General Procedure M used methyl (cis)-2-(1-((tert-butyldimethylsilyl)oxy)-4-phenylcyclohexyl)-N-(3-chlorophenyl)ethanimidothioate (161 mg), 220 μL hydroxylamine solution and EtOH (3.0 mL-. Purified using silica gel chromatography (5 to 20% EtOAc in hexanes) to afford 2-((cis)-1-((tert-butyldimethylsilyl)oxy)-4-phenylcyclohexyl)-N-(3-chlorophenyl)-N-hydroxyacetimidamide as a white foam.

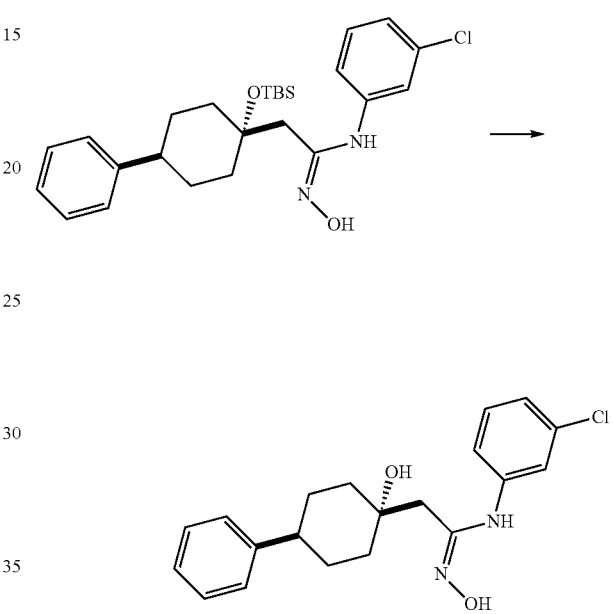

To a solution of 2-((cis)-1-((tert-butyldimethylsilyl)oxy)-4-phenylcyclohexyl)-N-(3-chlorophenyl)-N-hydroxyacetimidamide (72 mg, 0.15 mmol) in THF (1.0 mL) at 0° C. was added TBAF solution (1 M, 180 μL, 0.18 mmol). The mixture was warmed to rt and was stirred 16 h. The mixture was diluted with EtOAc (25 mL) and was filtered through silica (2×2 cm plug) washing with an additional 100 mL of EtOAc. The filtrated was concentrate under reduced pressure. The residue was purified using silica gel chromatography (10 to 50% EtOAc in hexanes) to afford the desired product as a white solid. (46 mg, 85%). $^1$H-NMR (400 MHz; CDCl$_3$): δ 7.30 (t, J=8.0 Hz, 2H), 7.24-7.20 (m, 4H), 7.17-7.13 (m, 2H), 6.97 (ddd, J=7.9, 2.1, 1.0 Hz, 1H), 6.89-6.87 (m, 2H), 2.70 (s, 2H), 2.44 (tt, J=12.1, 3.7 Hz, 1H), 1.88-1.84 (m, 2H), 1.72-1.58 (m, 5H), 1.10 (qd, J=12.9, 3.2 Hz, 2H) ppm. m/z 359.2 (M+H$^+$).

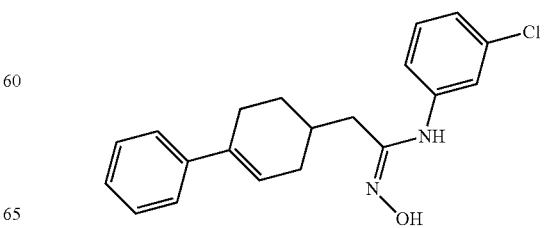

N-(3-Chlorophenyl)-N'-hydroxy-2-(2,3,4,5-tetrahydro-[1,1'-biphenyl]-4-yl)acetimidamide

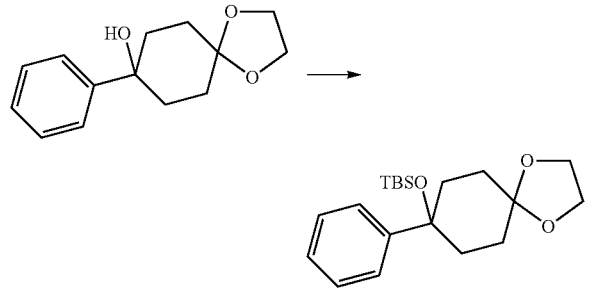

To a solution of 8-phenyl-1,4-dioxaspiro[4.5]decan-8-ol (1.74 g, 7.43 mmol) in CH₂Cl₂ (15 mL) at 0° C. was added 2,6-lutidine (1.19 g, 11.9 mmol) followed by dropwise addition of TBSOTf (2.93 g, 11.1 mmol). The resulting mixture was allowed to warm to rt and was stirred for 6 h. The mixture was cooled to 0° C. and NaHCO₃ solution (75 mL) was added. The biphasic mixture was stirred for 10 min, and EtOAc (100 mL) was added. The layers were separated, and the aqueous layer was extracted with EtOAc (3×50 mL). The combined organic layers were dried over anhydrous MgSO₄, filtered, and concentrated under reduced pressure. The crude mixture was purified employing silica gel chromatography (0 to 25% EtOAc in hexanes) to afford tert-butyldimethyl((8-phenyl-1,4-dioxaspiro[4.5]decan-8-yl)oxy)silane as an oil (1.69 g, 65% yield).

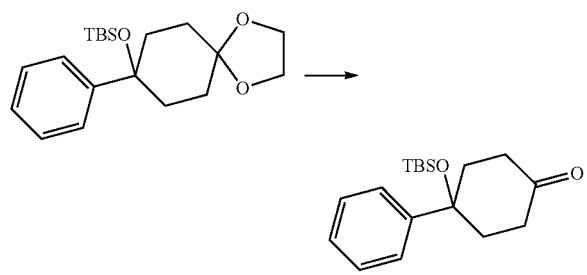

To a solution of tert-butyldimethyl((8-phenyl-1,4-dioxaspiro[4.5]decan-8-yl)oxy)silane (17.4 mg, 0.05 mmol) in acetone (0.5 mL) was added aqueous HCl solution (1M, 0.5 mL, 0.5 mmol). The mixture was stirred 16 h. EtOAc (10 mL) was added. The layers were separated, and the aqueous layer was extracted with EtOAc (3×10 mL). The combined organic layers were dried over anhydrous MgSO₄, filtered, and concentrated under reduced pressure. The residue was purified employing silica gel chromatography (0 to 50% EtOAc in hexanes) to afford 4-((tert-butyldimethylsilyl)oxy)-4-phenylcyclohexan-1-one as an oil.

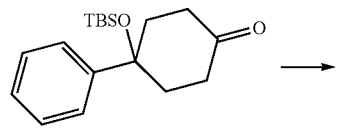

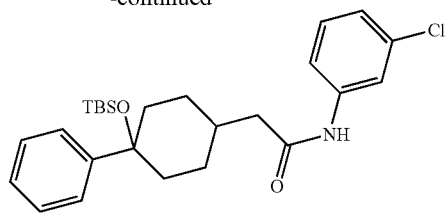

4-((tert-butyldimethylsilyl)oxy)-4-phenylcyclohexan-1-one was converted to 2-(4-((tert-butyldimethylsilyl)oxy)-4-phenylcyclohexyl)-N-(3-chlorophenyl)acetamide employing General Procedures D and F.

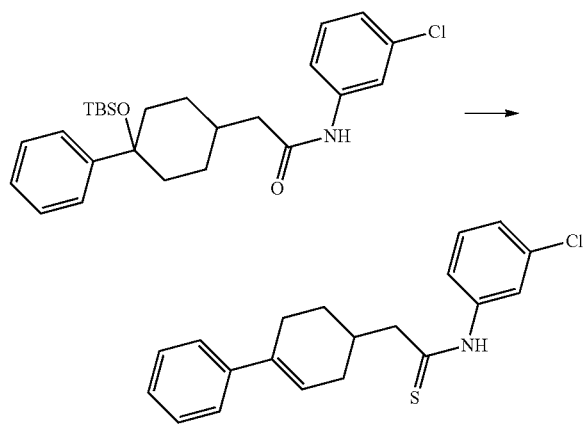

To 2-(4-((tert-butyldimethylsilyl)oxy)-4-phenylcyclohexyl)-N-(3-chlorophenyl)acetamide (105 mg, 0.23 mmol) in PhMe (1.2 mL) was added Lawesson's Reagent (51 mg, 0.13 mmol). The heterogeneous mixture was heated to 100° C. for 2 h. The mixture was concentrated under reduced pressure. The residue was purified employing silica gel chromatography (0 to 20% EtOAc in hexanes) to afford N-(3-chlorophenyl)-2-(2,3,4,5-tetrahydro-[1,1'-biphenyl]-4-yl)ethanethioamide as a solid (40 mg).

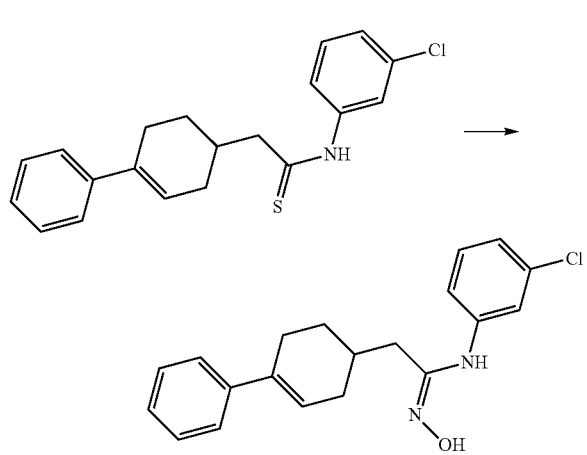

Prepared using General Procedures L and M. Purified using silica gel chromatography (5 to 15% EtOAc in hexanes) to afford the desired product as a white solid. m/z 341.2 (M+H⁺).

Biological Example
Particular compounds were evaluated in an IDO enzyme activity assay comparable to that described above. Results are provided in Table 1.
TABLE 1
| Activity of Specific Examples (Potency: IDO $IC_{50}$ A < 1 uM, B < 10 uM; C < 100 uM) | |
|---|---|
| | Potency |
| 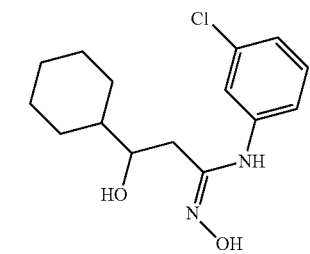 [SMILES: O/N=C(/CC(O)C1CCCCC1)Nc1cccc(Cl)c1] | B |
| 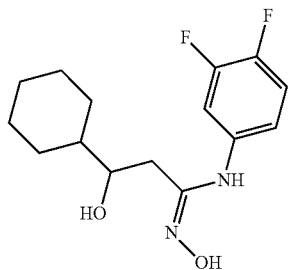 [SMILES: O/N=C(/CC(O)C1CCCCC1)Nc1ccc(F)c(F)c1] | C |
| 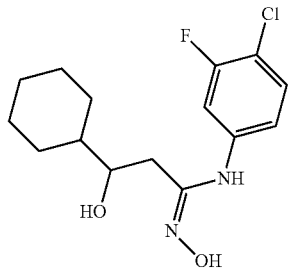 [SMILES: O/N=C(/CC(O)C1CCCCC1)Nc1ccc(Cl)c(F)c1] | C |
| 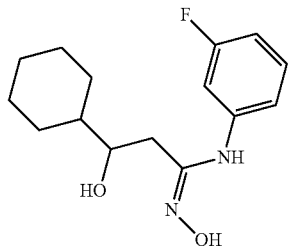 | C |
| 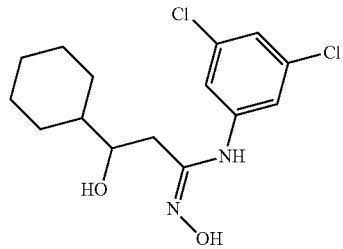 [SMILES: O/N=C(/CC(O)C1CCCCC1)Nc1cc(Cl)cc(Cl)c1] | B |
TABLE 1-continued
| Activity of Specific Examples (Potency: IDO $IC_{50}$ A < 1 uM, B < 10 uM; C < 100 uM) | |
|---|---|
| | Potency |
| 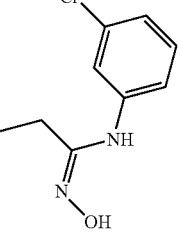 | B |
| 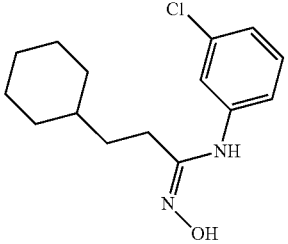 [SMILES: O/N=C(/CCC1CCCCC1)Nc1cccc(Cl)c1] | A |
| 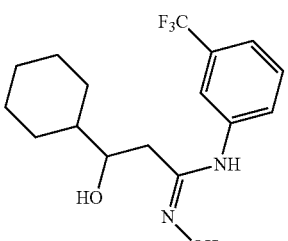 | C |
| 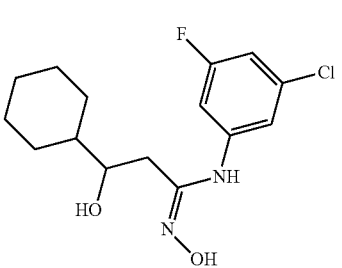 [SMILES: O/N=C(/CC(O)C1CCCCC1)Nc1cc(F)cc(Cl)c1] | C |
|  | B |
| 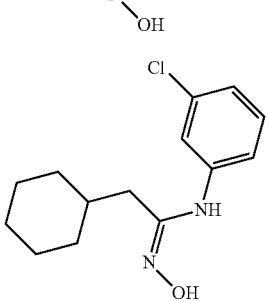 | A |

TABLE 1-continued
Activity of Specific Examples (Potency: IDO IC$_{50}$
A < 1 uM, B < 10 uM; C < 100 uM)
| Structure | Potency |
|---|---|
| 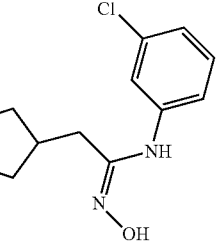 | A |
| 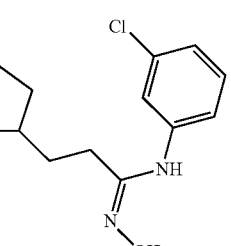 | A |
| 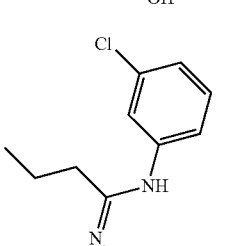 | A |
| 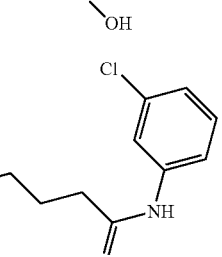 | A |
| 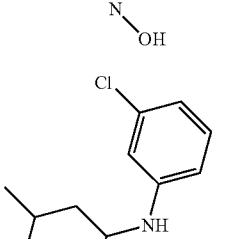 | A |
| 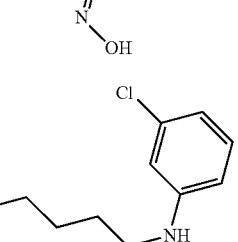 | A |
| 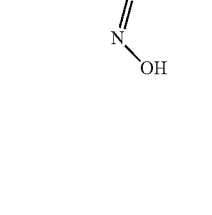 | B |
| 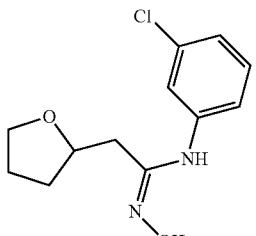 | A |
| 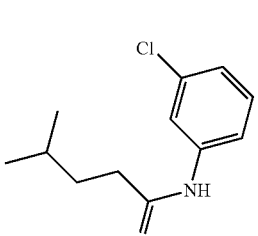 | B |
| 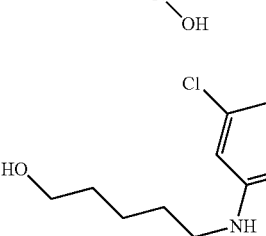 | B |
| 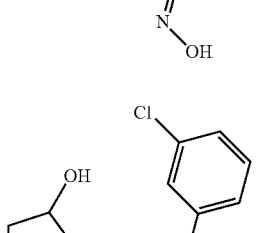 | C |

TABLE 1-continued

Activity of Specific Examples (Potency: IDO IC$_{50}$
A < 1 uM, B < 10 uM; C < 100 uM)

| | Potency |
|---|---|
| 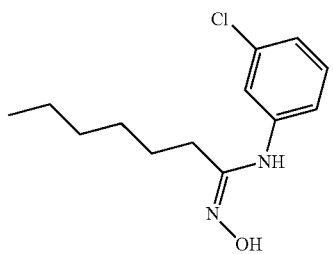 [SMILES: CCCCCC/C(=N/O)Nc1cccc(Cl)c1] | A |
| 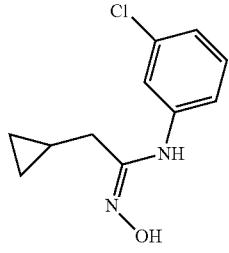 [SMILES: O/N=C(/CC1CC1)Nc1cccc(Cl)c1] | A |

Additional compounds and activity are provided in FIGS. 2A-2H.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:
1. A compound having the formula:

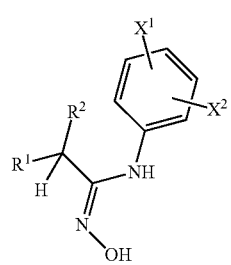

or a pharmaceutically acceptable salt, hydrate or solvate thereof, wherein, $X^1$ is selected from the group consisting of halogen, CN, SO$_2$NH$_2$, NHSO$_2$CH$_3$, NHSO$_2$CF$_3$, OCF$_3$, SO$_2$CH$_3$, SO$_2$CF$_3$, optionally substituted C$_1$-C$_4$ alkyl, optionally substituted C$_1$-C$_4$ alkoxy, C$_1$-C$_4$ haloalkyl, cyclopropyl, and CONH$_2$;

$X^2$ is selected from the group consisting of hydrogen, halogen, CN, SO$_2$NH$_2$, NHSO$_2$CH$_3$, NHSO$_2$CF$_3$, OCF$_3$, SO$_2$CH$_3$, SO$_2$CF$_3$, optionally substituted C$_1$-C$_4$ alkyl, optionally substituted C$_1$-C$_4$ alkoxy, C$_1$-C$_4$ haloalkyl, cyclopropyl, and CONH$_2$; and when $X^1$ and $X^2$ are on adjacent vertices of the phenyl ring they are optionally joined together to form an optionally substituted 5- or 6-member aromatic or aliphatic ring containing 0, 1, or 2 heteroatoms;

$R^1$ is selected from the group consisting of optionally substituted C$_3$-C$_8$ cycloalkyl, optionally substituted C$_3$-C$_8$ cycloalkyl-C$_1$-C$_4$ alkyl, and optionally substituted 3- to 7-membered cycloheteroalkyl; and $R^2$ is hydrogen;

or $R^1$ and $R^2$ are joined together to form an optionally substituted C$_3$-C$_8$ cycloalkyl;

with the proviso that $R^1$ and $R^2$ do not join together to form an unsubstituted cyclohexane ring.

2. The compound of claim 1, having the formula:

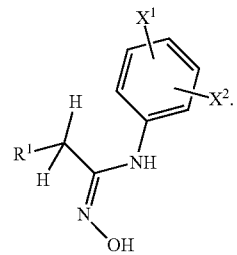

3. The compound of claim 1, wherein $X^2$ is hydrogen.

4. The compound of claim 1, wherein $R^1$ is selected from the group consisting of optionally substituted C$_3$-C$_6$ cycloalkyl and optionally substituted C$_3$-C$_6$ cycloalkyl-C$_1$-C$_4$ alkyl.

5. The compound of claim 1, wherein $R^1$ is optionally substituted 4- to 6-membered cycloheteroalkyl.

6. The compound of claim 1, wherein $R^1$ is selected from the group consisting of

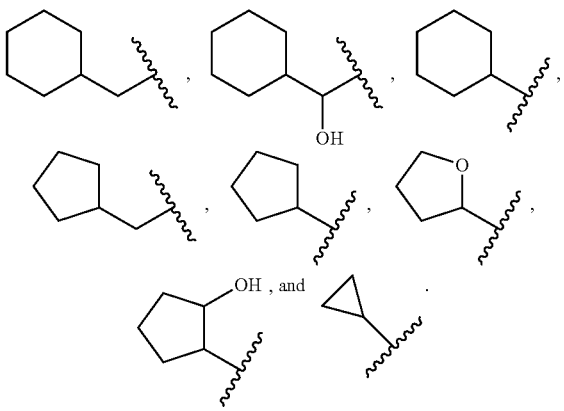

7. The compound of claim 1, wherein
$X^1$ is halogen or C$_1$-C$_4$ haloalkyl;
$X^2$ is hydrogen or halogen; and $R^1$ is selected from the group consisting of optionally substituted $C_3$-$C_8$ cycloalkyl, optionally substituted $C_3$-$C_8$ cycloalkyl-$C_1$-$C_4$ alkyl, and optionally substituted 3- to 7-membered cycloheteroalkyl;

or $R^1$ and $R^2$ are joined together to form an optionally substituted cyclobutyl, cyclopentyl or cycloheptyl.

8. The compound of claim 7, wherein $R^1$ is optionally substituted $C_3$-$C_6$ cycloalkyl or optionally substituted $C_3$-$C_6$ cycloalkyl-$C_1$-$C_4$ alkyl.

9. The compound of claim 7, wherein $R^1$ is optionally substituted 4- to 6-membered cycloheteroalkyl.

10. The compound of claim 7, wherein $R^1$ is selected from the group consisting of

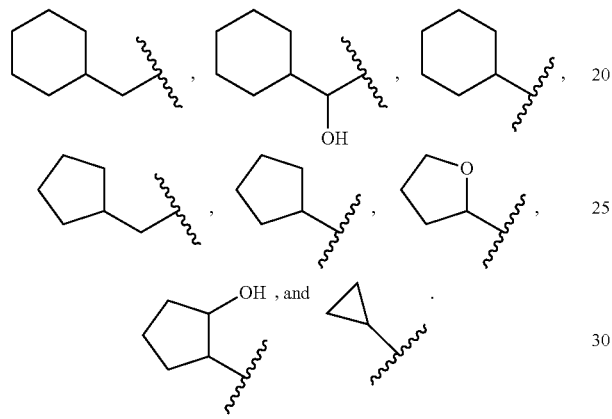

11. The compound of claim 1, that is

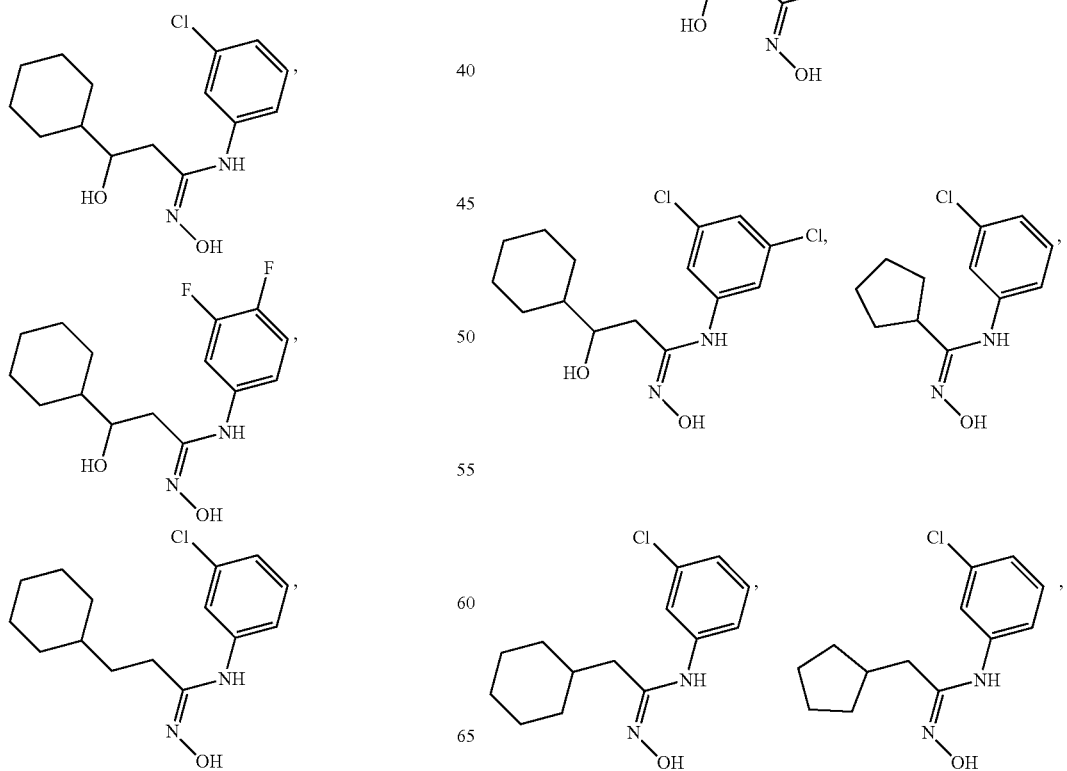

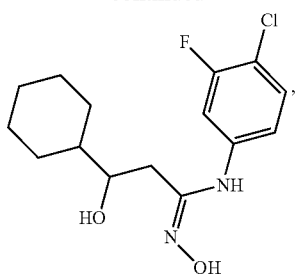

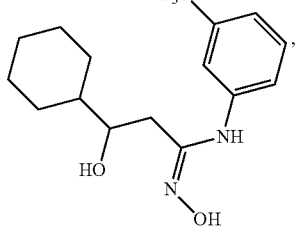

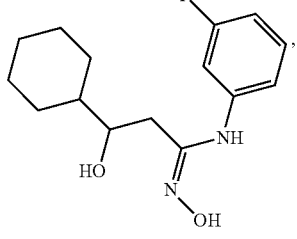

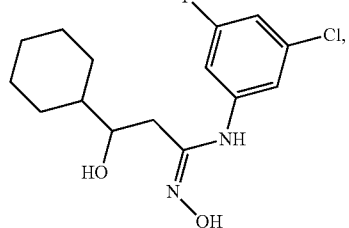

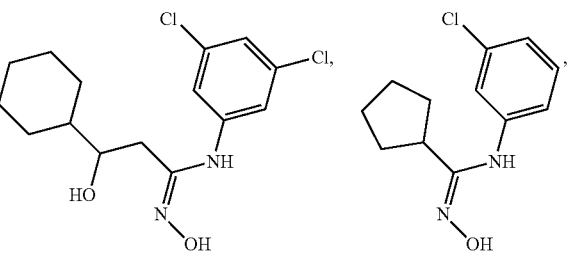

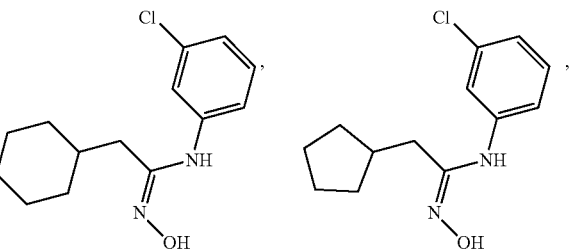

-continued

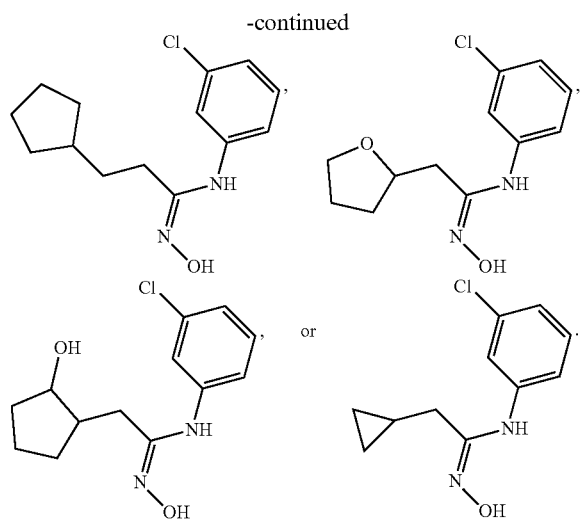

12. The compound of claim 1 having a potency level of less than 10 uM.

13. A pharmaceutical composition comprising a compound of claim 1 and a pharmaceutically acceptable excipient.

14. A combination comprising a compound of claim 1 and at least one additional therapeutic agent.

15. The combination of claim 14, wherein the at least one additional therapeutic agent is a chemotherapeutic agent, an immune- and/or inflammation-modulating agent, an anti-hypercholesterolemia agent, or an anti-infective agent.

16. The combination of claim 14, wherein the at least one additional therapeutic agent is an immune checkpoint inhibitor.

17. The compound of claim 1, wherein $X^1$ is halogen or $C_1$-$C_4$ haloalkyl and $X^2$ is hydrogen or halogen.

18. A combination comprising a compound of claim 2 and at least one additional therapeutic agent.

19. The combination of claim 18, wherein the at least one additional therapeutic agent is an immune checkpoint inhibitor.

20. A combination comprising a compound of claim 11 and at least one additional therapeutic agent.

21. The combination of claim 20, wherein the at least one additional therapeutic agent is an immune checkpoint inhibitor.

* * * * *

UNITED STATES PATENT AND TRADEMARK OFFICE
CERTIFICATE OF CORRECTION

PATENT NO. : 10,987,322 B2  
APPLICATION NO. : 15/315071  
DATED : April 27, 2021  
INVENTOR(S) : Jaen et al.

Page 1 of 1

It is certified that error appears in the above-identified patent and that said Letters Patent is hereby corrected as shown below:

In the Claims

Column 123, Line 22, delete "claim 1" and insert therefor -- claim 1, --

Signed and Sealed this  
Ninth Day of November, 2021

Drew Hirshfeld  
*Performing the Functions and Duties of the*  
*Under Secretary of Commerce for Intellectual Property and*  
*Director of the United States Patent and Trademark Office*